United States Patent [19]

Rodney et al.

[11] Patent Number: 5,356,894
[45] Date of Patent: Oct. 18, 1994

[54] MORPHOLINYL SUBSTITUTED [1,2,4]-TRIAZOLO[1,5-A]TRIAZINE AS ANTAGONIST

[76] Inventors: Peter W. Rodney, 32a Lime Grove, Macclesfield, Cheshire; Geraint Jones, 16 Packsaddle Park, Prestbury, Macclesfield, Cheshire; Michael G. Collis, 1 The Shrubbery; Valley Road, Barham, Canterbury, Kent; Simon M. Poucher, 3 Richmond Avenue, Handforth, Wilmslow, Cheshire, all of England

[21] Appl. No.: 94,572
[22] Filed: Jul. 21, 1993

Related U.S. Application Data

[63] Continuation-in-part of Ser. No. 708,265, May 28, 1991, Pat. No. 5,270,311.

[30] Foreign Application Priority Data

| May 29, 1990 | [GB] | United Kingdom | 9011913.2 |
| May 29, 1990 | [GB] | United Kingdom | 9011914.0 |
| Jan. 22, 1991 | [GB] | United Kingdom | 9101379.7 |
| Jan. 22, 1991 | [GB] | United Kingdom | 9101380.5 |
| Feb. 27, 1991 | [GB] | United Kingdom | 9104125.1 |
| Dec. 22, 1992 | [GB] | United Kingdom | 9226735.0 |

[51] Int. Cl.$^5$ ................. A61K 31/535; C07D 413/06
[52] U.S. Cl. ................. 514/233.2; 514/234.2; 514/234.5; 514/246; 544/113; 544/209; 544/212
[58] Field of Search ......... 544/113, 209, 212; 514/233.2, 234.2, 234.5, 246

[56] References Cited

U.S. PATENT DOCUMENTS

| 3,995,039 | 11/1976 | Rooney et al. | 544/212 |
| 4,133,674 | 1/1979 | Cartwright | 71/93 |

FOREIGN PATENT DOCUMENTS

| 459702 | 12/1991 | European Pat. Off. | |
| 515107 | 11/1992 | European Pat. Off. | |
| 515108 | 11/1992 | European Pat. Off. | |
| 0544443 | 6/1993 | European Pat. Off. | 544/209 |
| 544444 | 6/1993 | European Pat. Off. | |
| 544445 | 6/1993 | European Pat. Off. | |
| 743316 | 5/1974 | South Africa. | |
| 2134107 | 8/1984 | United Kingdom. | |

OTHER PUBLICATIONS

Ried et al., Tetrahedron, 44(23), 7155–62, 1988.
Ried, W. et al., "Synthesis of New Substituted Pyrazolo [1,5-a]-Pyrimidines and Pyrazolo [1,5-a]1,3,5-riazines", Tetrahedron vol. 44, No. 23, 1988, pp. 7155 to 7162.
Akerblom et al., "Nitrofuryltriazole Derivatives as Potential Urinary Tract Antibacterial Agents", J. Med. Chem. vol. 16, No. 4, pp. 312–319, 1973.

Primary Examiner—Mukund J. Shah
Assistant Examiner—Y. N. Gupta
Attorney, Agent, or Firm—Cushman, Darby & Cushman

[57] ABSTRACT

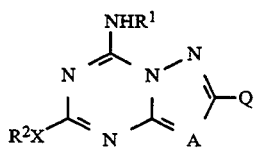

The invention concerns novel, pharmaceutically useful compounds of formula I in which Q is a 5-membered heteroaryl optionally bearing 1 or 2 substituents independently selected from (1–4C)alkyl and halogeno;

$R^1$ is hydrogen, (1–6C)alkyl, or (1–4C)alkanoyl;

$R^2$ (when not as hereinbelow defined together with X) is (1–6C)alkyl substituted by a group of formula $R^{10}Xb(CO)_m$ in which m is 0 or 1, provided that when m is 0, X and Xb are separated by at least two carbon atoms, Xb is an imino group of formula —NRb in which Rb together with $R^{10}$ and the adjacent nitrogen atom forms a morpholino, thiomorpholino, piperidino or azetidino ring;

and X is oxy, thio, sulphinyl, sulphonyl or an imino group of formula —NRa— in which Ra is hydrogen, (1–6C)alkyl or together with R2 and the adjacent nitrogen atom forms a morpholino, thiomorpholino, piperidino or azetidino ring; and A is N or CT in which T is hydrogen or (1–4C)alkyl;

or a pharmaceutically acceptable salt thereof; processes for the manufacture of the compounds and pharmaceutical compositions containing them. The compounds are useful as adenosine antagonists.

8 Claims, No Drawings

MORPHOLINYL SUBSTITUTED [1,2,4]-TRIAZOLO[1,5-A]TRIAZINE AS ANTAGONIST

This application is a continuation-in-part of U.S. Ser. No. 07/708,265 filed on May 28, 1991 which is now U.S. Pat. No. 5,270,311.

This invention concerns novel azole derivatives and, more particularly, certain 2-heteroaryl-triazolo[1,5-a][1,3,5]triazines and pyrazolo[2,3-a][1,3,5-]triazines which have useful pharmacological properties (and in particular antagonise the actions of adenosine such as vasodilation). The invention also includes pharmaceutical compositions containing the novel azole derivatives for use in treating certain diseases and disorders affecting mammalian cardiac, peripheral and/or cerebral vascular systems. Also included are processes for the manufacture and formulation of the novel azole derivatives.

The compound theophylline (1,3-dimethylxanthine) has been used clinically (usually as its ethylene diamine salt, which is also known as aminophylline) as a respiratory stimulant, a centrally acting stimulant, a bronchodilator, a cardiac stimulant and as a diuretic. This diversity of clinical uses is an indication of the range of pharmacological actions which have been attributed to theophylline. These include phosphodiesterase inhibition, adenosine receptor antagonism, mobilisation of intracellular calcium and the release of catecholamines. Recently theophylline has also been reported to be useful in treating myocardial ischaemia (Maseri et.al., *The Lancet*, 1989, 683–686), skeletal muscle ischaemia (Picano et al., *Angiology,* 1989, in press) and cerebral ischaemia (Skinhoj et al., *Acta. Neurol. Scand.*, 1970, 46, 129–140). The beneficial effects of theophylline in these ischaemic disorders are believed to be due to a reduction or prevention of the phenomenon known as "vascular steal" by virtue of the compound's ability to antagonise the actions of adenosine by blocking the adenosine receptors which mediate metabolism-linked vasodilatation.

The "vascular steal" phenomenon can occur when the major artery supplying a particular vascular bed is partially or totally occluded resulting in ischaemia. In this situation, the compromised vascular bed dilates and blood flow is maintained by either an increase in flow across the narrowed vessel or by an increase in flow through the collateral vessels. However, increased metabolic activity in adjacent vascular beds results in release of mediators such as adenosine, causing them to dilate, resulting in the limited blood flow to the compromised vascular bed being "stolen" by these adjacent areas. The loss of blood from compromised to normally perfused vascular beds by the phenomenon of "vascular steal" further diminishes the blood flow in the compromised vascular bed.

The diversity of pharmacological properties possessed by theophylline make it difficult to use in the regular treatment or prevention of occlusive diseases and conditions of the vasculature. Thus, its associated action as a phosphodiesterase inhibitor results in cardiac stimulation which is deleterious for patients with myocardial ischaemia. Furthermore, the relatively low potency of theophylline means that dose-levels which are therapeutically useful are close to those which can cause serious central side-effects.

Certain 2-heteroaryl-pyrazolo[2,3-a][1,3,5]triazines are known from W. Ried and S. Aboul-Fetouh, Tetrahedron, 44(23), 7155–7162, 1988. In addition, European patent application publication no. EP A2 383589, published on 22nd Aug., 1990, names certain other 2-heteroaryl-pyrazolo[2,3-a][1,3,5]triazines, although no details of their preparation are given. No therapeutic use is ascribed to any of these compounds.

Several triazolo[1,5-a][1,3,5]triazines and pyrazolo[2,3-a][1,3,5]triazines, which do not have a 2-heteroaryl substituent, have been ascribed therapeutic uses. Thus, certain triazolo[1,5-a][1,3,5]triazines have been disclosed as bronchodilators (see U.S. Pat. No. 4,734,413). Certain pyrazolo[2,3-a][1,3,5]triazines have been variously disclosed as inhibitors of gastric acid secretion (see British patent application publication no. 2134107 and European patent application publication no. EP A2 0172608); as antiinflammatory agents (see European patent applications publication nos. EP A2 0172608 and EP A2 207651); as bronchodilators (see British patent application publication no. GB 2016002, Belgian patent no. 815405 and U.S. Pat. No. 3,995,039), and as phosphodiesterase inhibitors (see U.S. Pat. No. 3,846,423).

We have now discovered (and this is a basis for our invention) that a group of novel 2-heteroaryl-triazolo[1,5-a][1,3,5]-triazines and pyrazolo[2,3-a][1,3,5]triazines of formula I defined below are effective antagonists of the actions of adenosine and in particular of its vasodilatory actions.

According to the invention there is provided a compound of the formula I set out hereinafter (together with the other formulae appearing in Roman numerals)-wherein:

Q is a 5-membered heteroaryl optionally bearing 1 or 2 substituents independently selected from (1–4C)alkyl and halogeno;

$R^1$ is hydrogen, (1–6C)alkyl, or (1–4C)alkanoyl;

$R^2$ is hydrogen, (3–12C)cycloalkyl, (3–6C)alkenyl, phenyl(3–6C)alkenyl, tetrafluorophenyl, pentafluorophenyl, 5- or 6-membered heteroaryl, optionally substituted (1–6C)alkyl or optionally substituted phenyl, said optionally substituted alkyl being unsubstituted or substituted by one of (3–6C)cycloalkyl, optionally substituted 5- or 6-membered heteroaryl, optionally substituted phenyl and a group of formula $R^{10}(CO)_nX-b(CO)_m$ in which $R^{10}$ is (1–6C)alkyl, (3–6C)cycloalkyl, optionally substituted phenyl or optionally substituted phenyl(1–4C)alkyl, n+m is 0 or 1, provided that when m is 0, X and Xb are separated by at least two carbon atoms, Xb is oxy, thio, sulphinyl, sulphonyl or an imino group of formula —NRb in which Rb is hydrogen, (1–6C)alkyl or together with $R^{10}$ and the adjacent nitrogen atom forms a 4 to 6-membered saturated heterocyclic ring, said optionally substituted 5- or 6-membered heteroaryl being unsubstituted or substituted by 1 or 2 of (1–4C)alkyl, (1–4C)alkoxy and halogeno, and any of said optionally substituted phenyl being unsubstituted or substituted by (1–4C)alkylenedioxy or by 1,2 or 3 of halogeno, cyano, trifluoromethyl, (1–4C)alkoxycarbonyl, hydroxy, (1–4C)alkanoyloxy, benzyloxy, halogenobenzyloxy, nitro, and (1–4C)alkyl or alkoxy optionally bearing a group of formula $R^{11}CO$ in which $R^{11}$ is (1–4C)alkoxy, (3–6C)alkylamino, (3–6C)cycloalkylamino or [N-(1–4C)alkyl] [N-(1–4C)dialkylamino(1–4C-

)alkyl]amino, and sulphamoyl of formula —SO$_2$.NR$^3$R$^4$ in which R$^3$ and R$^4$ are independently hydrogen or (1–4C)alkyl, or R$^3$ is hydrogen and R$^4$ is [(2–5C)alkoxycarbonyl]methyl, carbamoylmethyl or [N-(1–4C)alkylcarbamoyl]methyl; and X is oxy, thio, sulphinyl, sulphonyl or an imino group of formula —NRa— in which Ra is hydrogen, (1–6C)alkyl or together with R$_2$ and the adjacent nitrogen atom forms a 4 to 6-membered saturated heterocyclic ring; and A is N or CT in which T is hydrogen or (1–4C)alkyl; or a pharmaceutically acceptable salt thereof.

One group of compounds of general formula I consists of those wherein Q is a 5-membered heteroaryl (e.g. furyl or thienyl) optionally bearing 1 or 2 substituents independently selected from (1–4C)alkyl and halogeno; X is oxy, thio or an imino group of the formula —NRa— in which Ra is hydrogen or (1–6C)alkyl; R$^1$ is hydrogen, (1–6C)alkyl or (1–4C)alkanoyl; and R$^2$ is:

(a) phenyl, pyridyl, isoxazolyl, thiadiazolyl, tetrafluorophenyl, pentafluorophenyl, or phenyl bearing 1, 2 or 3 substituents independently selected from (1–4C)alkyl, (1–4C)alkoxy, halogeno, cyano, trifluoromethyl, nitro, benzyloxy, halogenobenzyloxy, hydroxy, and a sulphamoyl group of the formula —SO$_2$.NR$^3$R$^4$ in which R$^3$ and R$^4$ are independently hydrogen or (1–4C)alkyl, or R$^3$ is hydrogen and R$^4$ is [(2–5C)alkoxycarbonyl]methyl, carbamoylmethyl or [N-(1–4C)alkylcarbamoyl]methyl;

(b) (1–6C)alkyl, (3–12C)cycloalkyl, (3–6C)cycloalkyl(1–4C)alkyl, furyl, thienyl, phenyl(1–4C)alkyl, furyl(1–4C)alkyl, thienyl(1–4C)alkyl, a furyl, thienyl or phenyl moiety of which may itself optionally bear 1 or 2 substituents independently selected from (1–4C)alkyl, (1–4C)alkoxy and halogeno; or (c) a group of the formula R$^5$.Xa.CH$_2$.CH$_2$— in which R$^5$ is (1–6C)alkyl or phenyl which latter may optionally bear 1 or 2 substituents independently selected from (1–4C)alkyl, (1–4C)alkoxy and halogeno, and Xa is oxy, thio, sulphinyl, sulphonyl, imino or N-(1–6C)alkylimino, or in which the group R$^5$.Xa— is morpholino, thiomorpholino, pyrrolidino, piperidino or azetidino; and A is N or CT in which T is hydrogen or (1–4C)alkyl; or a pharmaceutically acceptable salt thereof.

It will be appreciated that depending on the nature of the substituents, in containing one or more chiral centres, the formula I compounds may exist in and be isolated in one or more different enantiomeric or racemic forms (or a mixture thereof). It is to be understood that the invention includes any of such forms which possesses the property of antagonising the actions of adenosine, it being well known how to prepare individual enantiomeric forms, for example, by synthesis from appropriate chiral starting materials or by resolution of a racemic form. Similarly, the adenosine antagonist properties of a particular form may be readily evaluated, for example by use of one or more of the standard in vitro or in vivo screening tests detailed hereinbelow.

A particular value for Q when it is a 5-membered heteroaryl is, for example, furyl, thienyl, oxazolyl, thiazolyl, isoxazolyl or isothiazolyl, which heteroaryl moieties may optionally bear 1 or 2 substituents independently selected from methyl, ethyl, fluoro, chloro and bromo. An example of a particularly preferred value for Q is furyl, optionally substituted as defined above. The 2-furyl group is preferred.

A particular value for R$^1$ when it is alkyl is, for example, methyl, ethyl, propyl or butyl, and when it is alkanoyl is, for example, formyl, acetyl or propionyl, of which formyl is preferred. Another preferred value for alkanoyl is acetyl. An example of a particularly preferred value for R$^1$ is hydrogen.

A particular value for T when it is alkyl is, for example, methyl, ethyl or propyl.

An example of a particularly preferred value for T is hydrogen.

A particular value for R$^2$ when it is alkyl is, for example, methyl, ethyl, isopropyl, propyl, butyl or sec-butyl. Another particular value is n-pentyl.

A particular value for Ra when it is alkyl is, for example, methyl or ethyl.

Particular values for optional substituents which may be present when R$^2$ or R$^5$ is phenyl (or on a phenyl, furyl or thienyl moiety attached to alkyl) include, for example:

for alkyl: methyl or ethyl;
for alkoxy: methoxy or ethoxy; and
for halogeno: fluoro, chloro or bromo.

A particular value for a halogenobenzyloxy substituent which may be present on R$^2$ when it is phenyl is, for example, 4-fluorobenzyloxy or 4-chlorobenzyloxy.

A particular value for R$^2$ when it is alkenyl is allyl.

A particular value for R$^2$ when it is phenylalkenyl is 3-phenyl-2-trans-propenyl.

Particular values for R$^2$ when it is 5- or 6-membered heteroaryl include, for example, pyridyl, isoxazolyl or thiadiazolyl.

A particular value for R$^3$ or R$^4$ when it is alkyl is, for example, methyl or ethyl.

A particular value for R$^4$ when it is (alkoxycarbonyl)methyl is, for example, (methoxycarbonyl)methyl or (ethoxycarbonyl)methyl, and when it is (N-alkylcarbamoyl)methyl is, for example, (N-methyl- or N-ethylcarbamoyl)methyl.

A particular value for R$^2$ when it is cycloalkyl is, for example, cyclopropyl, cyclobutyl, cyclopentyl, cyclohexyl or norbornyl, and when it is cycloalkylalkyl is, for example, one of the latter cycloalkyl moieties attached to methyl, ethyl (at position 1 or 2 thereof) or propyl (at position 1, 2 or 3 thereof).

A particular value for R$^2$ when it is phenylalkyl, furylalkyl or thienylalkyl is, for example, benzyl, 1-phenylethyl, 2-phenylethyl, 2-furylmethyl, 3-furylmethyl, 2-thienylmethyl, 3-thienylmethyl or 2-(2-thienyl)ethyl.

Particular values for optional substituents on alkyl when R$^2$ is optionally substituted alkyl (such as methyl or ethyl) include, for example:

for cycloalkyl: cyclopropyl;
for optionally substituted 5- or 6-membered heteroaryl: furyl, pyridyl or thienyl; for a group of formula R$^{10}$(CO)$_n$Xb(CO)$_m$:
for R$^{10}$: methyl, ethyl, n-propyl, cyclohexyl, phenyl or 4-hydroxybenzyl,
for Xb: oxy, thio, sulphinyl, imino, methylimino or, together with R$^{10}$, piperidino.

Particular values for optional substituents on phenyl when R$^2$ is optionally substituted phenyl or optionally substituted phenylalkyl (such as 2-phenylethyl) include, for example:

for alkylenedioxy: methylenedioxy;
for halogeno: fluoro, chloro or bromo;

cyano;
trifluoromethyl;
for alkoxycarbonyl: methoxycarbonyl;
hydroxy;
for alkanoyloxy: pivaloyloxy;
benzyloxy;
for halogenobenzyloxy: 4-fluorobenzyloxy or 4-chlorobenzyloxy;
nitro;
for alkyl or alkoxy optionally substituted by a group of formula $R^{11}CO$: methyl, methoxy, ethyl, ethoxy, 2-(t-butoxycarbonyl)ethyl, methoxycarbonylmethyl, methoxycarbonylmethoxy, 2-(methoxycarbonyl)ethyl, n-propylaminocarbonylmethyl, n-propylaminocarbonylmethoxy, cyclopentylaminocarbonylethyl, cyclohexylaminocarbonylmethyl, [N-methyl, N,N-dimethylaminoethyl]aminocarbonylmethyl or [N-methyl, N,N-dimethylaminoethyl]aminocarbonylmethoxy; and
for sulphamoyl: —$SO_2NH_2$ or —$SO_2N(CH_3)_2$.

A particular value for $R^5$ when it is alkyl is, for example, methyl, ethyl, isopropyl, propyl or butyl.

Particular values for X include, for example, oxy, thio, imino, methylimino or, together with $R^2$ morpholino thiomorpholino pyrrolidino, piperidino or azetidino.

A particular value for Xa when it is N-alkylimino is, for example, methylimino, ethylimino or propylimino.

A group of compounds which is of particular interest comprises those compounds of the formula II set out hereinafter wherein X is oxy, thio or an imino group of the formula —NRa— in which Ra is hydrogen or (1–6C)alkyl; Y is hydrogen, halogeno or (1–4C)alkyl; and $R^6$ is:

(a) phenyl, pentafluorophenyl, pyridyl, thiadiazolyl, or phenyl bearing 1 or 2 substituents independently selected from (1–4C)alkyl, (1–4C)alkoxy, halogeno, cyano, trifluoromethyl, benzyloxy, halogenobenzyloxy and hydroxy;

(b) (1–6C)alkyl, (3–6C)cycloalkyl, norbornyl, (3–6C)cycloalkyl(1–4C)alkyl, furyl, thienyl, phenyl(1–4C)alkyl, furyl(1–4C)alkyl, thienyl(1–4C)alkyl, a furyl, thienyl or phenyl moiety of which may itself optionally bear 1 or 2 substituents independently selected from (1–4C)alkyl, (1–4C)alkoxy and halogeno; or (c) a group of the formula $R^5.Xa.CH_2.CH_2$— in which $R^5$ is (1–6C)alkyl or phenyl which latter may optionally bear 1 or 2 substituents independently selected from (1–4C)alkyl, (1–4C)alkoxy and halogeno, and Xa is oxy, thio, sulphinyl, sulphonyl, imino or N-(1–6C)alkylimino, or in which the group $R_5.Xa$— is morpholino, pyrrolidino or piperidino; and $A^1$ is N or $CT^1$ in which $T^1$ is hydrogen or methyl; together with the pharmaceutically acceptable salts and N-(1–6C)alkanoyl derivative thereof.

Specific values for the generic radicals embodied within $R^6$ include, for example, the appropriate values for $R^2$ defined above.

Specific values for the group $R^2.X$— or $R^6.X$— include, for example, the following:

phenoxy, ethoxy, 4-chlorophenoxy, benzyloxy, 4-benzyloxyphenoxy, 4-(4-chlorobenzyloxy)phenoxy, 4-hydroxyphenoxy, 4-methoxyphenoxy, 3-fluorophenoxy, 2-phenylethoxy, 2-phenoxyethoxy, 2-methoxyethoxy, 4-cyanophenoxy, butoxy, 3-methoxyphenoxy, 2-methoxyphenoxy, 2-fluorophenoxy, allyloxy, 2-(phenylthio)ethoxy, 4-fluorophenoxy, 2-cyanophenoxy, [1,2]isoxazol-3-yloxy, pyrid-3-yloxy, [1,2,5]thiadiazol-3-yloxy, thiophenoxy, cyclopentylthio, (2-furylmethyl)thio, methylthio, 2-methoxyphenylthio, benzylthio, cyclohexylamino, propylamino, anilino, allylamino, pyrrolidino, morpholino, benzylamino, methylamino, ethylamino, isopropylamino, butylamino, (2-phenylethyl)amino, [S]-(1-phenylethyl)amino and (2-dimethylaminoethyl)amino.

A particularly preferred group of compounds of general formula I consists of those compounds wherein:

Q is furyl;

$R^1$ is hydrogen or acetyl;

$R^2$ is cyclopentyl, cyclohexyl, tetrafluorophenyl, pentafluorophenyl, pyridyl, thiadiazolyl, (4–6C)alkyl, optionally substituted phenyl(1–2C)alkyl, optionally substituted phenyl, furylmethyl or pyridylmethyl, any of said optionally substituted phenyl being unsubstituted or substituted by methylenedioxy, or by one of fluoro, chloro, cyano, trifluoromethyl, methoxycarbonyl, hydroxy, pivaloyloxy, nitro, methyl, methoxy, t-butoxycarbonylethyl and sulphamoyl;

X is oxy or imino; A is N or CT in which T is hydrogen; and pharmaceutically acceptable salts thereof.

Of this particularly preferred group of compounds, those wherein $R^2$ is cyclohexyl, tetrafluorophenyl, 2-methylpropyl, phenyl, 2-fluorophenyl, 3-fluorophenyl, 2-chlorophenyl, 3-chlorophenyl, 2-cyanophenyl, 3-cyanophenyl, 2-nitrophenyl, 2-methoxycarbonylphenyl, 2-methoxyphenyl, 3-methoxyphenyl, 2-methylphenyl, 3-methylphenyl, 3-trifluoromethylphenyl, benzyl, 2-fluorobenzyl, 3-methoxybenzyl, 2-furylmethyl, 2-phenylethyl, 2-(4-chlorophenyl)ethyl, 2-(2-methylphenyl)ethyl, 2-(4-t-butoxycarbonylphenyl)ethyl, 2-(4-hydroxyphenyl)ethyl, 2-(4-sulphamoylphenyl)ethyl and 2-(4-pivaloyloxyphenyl)ethyl are especially preferred.

Particular pharmaceutically acceptable salts include, for example, salts with acids affording physiologically acceptable anions, for example, salts with strong acids, such as hydrochloric, hydrobromic, sulphuric, phosphoric, methanesulphonic and trifluoroacetic acids. In addition, for those compounds of formula I which are sufficiently basic, suitable salts include, for example, salts with organic acids affording a physiologically acceptable anion such as salts with oxalic, citric or maleic acid. Certain compounds of formula I, for example those in which $R^2$ comprises a phenol group, may form base salts with bases affording physiologically acceptable cations, such as alkali metal and alkaline earth metal salts.

Specific compounds of the formula I which are of interest are described hereinafter in the accompanying examples. Of these, compounds of particular interest include, for example, the compounds described in Examples 1, 3, 4, 12, 17, 18, 19, 24, 27, 32, 38, 44, 72, 75, 81, 82, 83, 84, 102, 118, 129, 136, 142 and 180 or the pharmaceutically acceptable acid-addition salts thereof, and these are provided as a further feature of the invention.

The compound of Example 180 has been found to be a selective antagonist of adenosine at the adenosine A2a receptor, the receptor which mediates the vasodilatory actions of adenosine. It has also been found to possess particularly good aqueous solubility and to be surprisingly effective in vivo on oral and parenteral administration.

The compounds of formula I may be manufactured using procedures analogous to those well known in the arts of heterocyclic and organic chemistry for the production of structurally analogous compounds. Such procedures are included as a further feature of the invention and include the following preferred procedures for the manufacture of a compound of the formula I in which $R^1$, $R^2$, X, A and Q have any of the meanings defined above:

(a) The reaction of a compound of the formula III in which Z is a suitable leaving group, for example hydrocarbylsulphonyl such as (1–6C)alkylsulphonyl (such as methylsulphonyl or ethylsulphonyl), aryloxy such as phenoxy or halogeno (such as chloro or bromo), with a compound of the formula $R^2.XH$.

The process is generally carried out under basic conditions. These may be conveniently provided by the inherent basicity of the compound of formula $R^2.XH$ itself for example when X is imino or when $R^2$ contains an amino group. Alternatively, the basic conditions may be provided by adding a suitable base to the reaction mixture. Suitable bases include, for example, tertiary amines such as trimethylamine, triethylamine, pyridine, 2,6-dimethylpyridine and 1,8-diazabicyclo[5.4.0]undec-7-ene. It will be appreciated that the basic conditions may also be provided by using the compound of the formula $R^2.XH$ in the form of a salt such as an alkali metal salt, for example, a lithium, sodium or potassium salt. Such a salt may be prepared separately, or formed in situ immediately prior to the above process (a), by any conventional method, for example by reacting the compound of the formula $R^2.XH$ with an alkali metal (1–4C)alkoxide, hydroxide or hydride in a suitable solvent or diluent such as acetonitrile, 1,2,-dimethoxyethane, t-butyl methyl ether, tetrahydrofuran, ethanol or N,N-dimethylformamide.

The process (a) will generally be performed at a temperature in the range, for example, 10° to 120° C. and conveniently in the range 30° to 80° C. and in a suitable solvent or diluent such as acetonitrile, ethanol, tetrahydrofuran, 1,2-dimethoxyethane, t-butyl methyl ether or N,N-dimethylformamide.

The starting materials of formula III (certain of which are also compounds of the invention) may be obtained by standard procedures well known in the art. Thus, for example, those compounds of formula III in which Z is alkylsulphonyl may be made by oxidation of the corresponding alkylthio derivative of formula IV in which $R^7$ is (1–6C)alkylthio, using a conventional oxidant such as a peracid, for example, peracetic, perbenzoic or chloroperbenzoic acid, conveniently at a temperature in the range, for example, 0° to 40° C., and in a suitable solvent or diluent such as dichloromethane or chloroform. Similarly, those compounds of the formula III in which Z is chloro or bromo may be obtained, for example, by reacting an alkylthio derivative of formula IV (especially in which $R^7$ is methylthio or ethylthio) with chlorine or bromine in the presence of hydrogen chloride or hydrogen bromide, respectively, at a temperature in the general range, for example, −20° to 15° C. and in a generally inert polar solvent such as ethanol or 2-propanol. The compounds of formula III in which Z is phenoxy may conveniently be prepared by one of processes (b) to (e) described hereinafter.

The starting alkylthio starting materials of formula IV (certain of which are also compounds of the invention) may themselves be obtained, for example, by reaction of a compound of the formula V with the appropriate dialkyl N-cyanodithioiminocarbonate of formula VI, in which $R^7$ has any of the meanings defined above, at elevated temperature in the range, for example, 60° to 200° C., conveniently as a melt in the absence of solvent or diluent, to give the compound of formula IV in which $R^1$ is hydrogen. When a compound of formula I in which $R^1$ is alkyl is required, the compound of formula IV in which $R^1$ is hydrogen may be alkylated or acylated in conventional manner.

It will be understood that in some circumstances, when A is N, some of the isomeric 7-alkylthio-5-amino compound of formula IVa may also be obtained during the reaction of the formula V and VI compounds and that this material may be separated by conventional procedures, for example by chromatography.

The starting compounds of formula V wherein A is N may themselves be obtained, for example by reacting the appropriate iminoether of the formula Q.C(OR)=NH in which R is (1–4C)alkyl such as methyl or ethyl (formed from the corresponding nitrile of the formula Q.CN and alcohol of the formula R.OH in the presence of an anhydrous acid such as hydrogen chloride) with an aminoguanidine salt (especially the nitrate) in the presence of a suitable base, such as pyridine or 2,6-lutidine, which may also be used as the reaction solvent, at a temperature in the range, for example, 60°–120 ° C.

The starting compounds of formula V wherein A is CT may themselves be obtained, for example by reacting the appropriate ester of the formula $Q.CO_2R$ (in which R is lower alkyl such as methyl or ethyl) under basic conditions with an alkali metal salt of the formula T.CHM.CN (in which M is an alkali metal such as sodium or lithium), conveniently produced in situ by adding a nitrile of the formula $T.CH_2.CN$ to a solution of the alkali metal in liquid ammonia, to give the corresponding cyanoalkylketone of the formula Q.CO.CH(T).CN. The latter compound is then cyclised with hydrazine, for example by heating in a suitable solvent or diluent such as ethanol or propanol to give the required pyrazole of formula V.

(b) For those compounds of formula I in which X is thio or oxy, a compound of the formula V is reacted at elevated temperature with a compound of formula VII in which X is thio or oxy.

The process is generally performed at a temperature in the general range, for example, 60° to 200 ° C. and may be performed in the absence of any solvent or diluent especially when $R^2$ is alkyl or phenyl. Otherwise any conventional solvent or diluent may conveniently be used which is generally inert and of adequate boiling point. It will be appreciated that, under certain circumstances for example when the reaction is performed at temperatures only slightly above room temperature, it is possible to produce significant quantities of the thermodynamically less stable, isomeric [1,2,4]triazolo[4,3-a][1,3,5]triazine derivative of the formula VIII, and this isomeric material may be separated by conventional procedures such as chromatography.

(c) The invention accordingly provides a further process for preparing a compound of formula I in which A is N, in which a [1,2,4]triazolo[4,3-a][1,3,5]triazine derivative of the formula VIII is rearranged.

The rearrangement is generally carried out by heating the compound of formula VIII in a suitable solvent or diluent, for example, a (1–6C)alkanol, such as ethanol, 2-propanol or butanol, at a temperature in the general range, for example, 60° to 140 ° C. The rearrangement may optionally be carried out in the presence of an acid or base catalyst, for example an alkali metal alkoxide or hydroxide such as sodium hydroxide.

The starting materials of formula VIII may be obtained, for example, as described in connection with (b) above as illustrated in Example 4 hereinafter or by conventional techniques of heterocyclic chemistry.

(d) For those compounds of formula I in which $R^2$ is hydroxyphenyl, a corresponding derivative of formula I in which the hydroxy group is protected, for example with a benzyl group, is deprotected.

The protecting group and deprotection conditions are those well known in the art for use with hydroxy groups and which are compatible with the presence of other reactive groups in the formula I compound. Thus, for example, a benzyl group may be removed by hydrogenation in the presence of a suitable catalyst such as palladium-on-carbon at or about atmospheric pressure of hydrogen in a suitable inert diluent or solvent such as methanol, ethanol or t-butyl methyl ether and at or about ambient temperature.

The protected derivatives of formula I may in general be made using analogous procedures to processes (a)–(c) above but starting from the appropriately protected starting materials.

(e) For those compounds of formula I in which A is N and $R^1$ is hydrogen or (1–6C)alkyl, a compound of formula X in which Za is a suitable leaving group, for example aryloxy (such as phenoxy), alkylthio (such as methylthio) or halogeno (such as chloro or bromo) is reacted with a compound of formula $R^1NH_2$.

The process is conveniently effected at a temperature in the range of, for example, from 0° to 100° C. Suitable solvents for the process include alcohols such as ethanol and ethers such as tetrahydrofuran. When $R^1$ is hydrogen, it is particularly convenient to employ a solution of ammonia in an alcohol, such as ethanol, at ambient temperature.

The starting materials of formula X may be obtained by dehydrating a compound of formula XI. Suitable dehydration agents include, for example, polyphosphoric acid silyl esters such as polyphosphoric acid trimethylsilyl ester, phosphorus pentoxide or a sulphonyl chloride such as p-toluenesulphonylchloride. The dehydration is conveniently effected at a temperature in the range of from 60°–180° C. When phosphorus pentoxide is used, convenient solvents include the aromatic hydrocarbons such as xylene or toluene. When a sulphonyl chloride is used, convenient solvents include tertiary amines such as pyridine.

It will be appreciated that the compounds of formula X in which Za represents alkylthio correspond with the compounds of formula IVa whose preparation is described hereinbefore.

The compounds of formula XI may be obtained by reacting a compound of formula XII with a compound of formula QCOHal in which Hal is a halogen atom such as a chlorine atom. The reaction is conveniently effected at a temperature in the range of from −10° to 40° C. Suitable solvents for the reaction include halogenated hydrocarbons such as dichloromethane.

The compounds of formula XII may be obtained by reacting a compound of formula XIII in which Zb is a leaving group as defined for Za with hydrazine.

Alternatively, the compounds of formula XI may be obtained by reacting a compound of formula XIII with a compound of formula $QCONHNH_2$.

Process (e) is particularly suitable for preparing compounds of formula I in which $R^2X$ is phenoxy, starting from the compound of formula XIII in which $R^2X$ and Za are phenoxy.

It will be appreciated that those compounds in which $R^1$ is other than hydrogen may also be obtained by carrying out a conventional alkylation or acylation of the corresponding formula I compound in which $R^1$ is hydrogen obtained by one of processes (a)–(d) above.

It will also be appreciated that those compounds of formula I in which $R^2$ contains an acyloxy group, for example where $R^2$ is (1–4C)alkanoyloxyphenyl or (1–4C)alkanoyloxyphenyl(1–6C)alkyl, may be prepared by acylating the corresponding compounds of formula I in which $R^2$ comprises a hydroxy group, as for example where $R^2$ is hydroxyphenyl or hydroxyphenyl(1–4C)alkyl. The acylation may be conducted by reaction with any conventional acylating agent, for example a (1–4C)alkanoyl halide or (1–4C)alkanoic acid anhydride.

Compounds of formula I wherein X, Xa or Xb is sulphinyl or sulphonyl may conveniently be prepared by oxidising the corresponding compounds of formula I wherein X, Xa or Xb is thio or sulphinyl. Suitable oxidising agents include for example, peracids such as peracetic, perbenzoic or chloroperbenzoic acid. The oxidation is conveniently effected at a temperature in the range of from 0° to 40° C. Suitable solvents include halogenated hydrocarbons such as dichloromethane or chloroform.

Whereafter, when a pharmaceutically acceptable salt is required, it may be obtained, for example, by reacting a compound of formula I with the appropriate acid or base affording a physiologically acceptable ion or another conventional procedure.

Similarly, when an optically active form of a chiral compound of formula I is required, either one of processes (a)–(e) above may be carried out using the appropriate optically active starting material or else a racemic form may be resolved by a conventional procedure, for example, using an optically active form of a suitable acid.

Certain of the starting materials used in the processes according to the invention are novel, and these are provided as further aspects of the invention. For example, the invention provides compounds of formula V in which A is N and Q is as defined hereinabove, and acid addition salts thereof (e.g., hydrochloride salts). The invention also provides compounds of formula VIII in which Q, $R^1$, $R^2$ and X are as defined hereinabove. The invention also provides compounds of formula X in which Q, $R^2$, X and Za are as defined hereinabove.

As stated above, the compounds of the invention possess the property of antagonising one or more of the physiological actions of adenosine and are valuable in the treatment of diseases and medical conditions affecting the mammalian cardiac, peripheral and/or cerebral vascular systems, such as ischaemic heart disease, peripheral vascular disease (claudication) and cerebral ischaemia. The compounds may also be useful in the treatment of migraine.

The effects of compounds of formula I as adenosine receptor antagonists may be demonstrated in one or more of the following standard in vitro and/or in vivo tests.

(a) $A_{2a}$ Adenosine Receptor Affinity Test

This test involves the ability of a test adenosine antagonist to displace the known adenosine mimetic agent [$^3$H]-N-ethylcarboxamidoadenosine (NECA) from binding sites on membrane preparations derived from the rat phaeochromocytoma cell line PC 12 (available from the Beatson Institute, Glasgow). The basic procedure has been described by Williams et al. (*J. Neurochemistry*, 1987, 48(2), 498–502).

The membrane preparation is obtained as follows: Frozen pellets of PC12 cells are washed twice with ice cold, buffered, physiological saline and the cells recovered by centrifugation (1500G) at 3° C. The separated cells are then suspended in hypotonic solution (distilled water), allowed to stand on ice for 30 minutes and are then carefully homogenized using a standard high-speed homogeniser with periodic ice-cooling to obtain a fine suspension. The homogenate is centrifuged (48000G) and the pellet is resuspended in 50 mM tris-HCl buffer, pH 7.4 containing adenosine deaminase (5 units/ml, Type VII from calf intestinal mucosa, available from Sigma Chemical Corporation, under reference no. A1280). The mixture is then incubated at 37° C. After 20 minutes, the reaction is terminated by dilution with ice-cold buffer and transfer onto ice. The material obtained containing the cell membranes is recovered by centrifugation and washed by resuspension in buffer and recentrifugation. The pellet produced is then resuspended in ice-cold buffer using a hand-driven homogenizer. The resultant membrane suspension is frozen and stored under liquid nitrogen until required.

Binding studies are carried out in microtitre plates, the assay mixtures being buffered in 50 mM tris-HCl, pH 7.4 at room temperature. The test compound is dissolved in dimethyl sulphoxide (DMSO) and then diluted with assay buffer to give the test solutions. [The final concentration of DMSO is not allowed to exceed 1% by volume, at which level it does not affect radioligand binding to the membrane receptor.] Incubations are performed at 30° C. for 90 minutes in a total volume of 150 μl comprising the test solution or buffer (50 μl), tritiated NECA (50 μl) and membrane suspension (50 μl). After incubation, the samples are rapidly filtered over glass-fibre mats and the filter mats are washed to remove non-receptor-bound radioligand. Receptor-bound radioligand entrapped on the filter mats is then determined by liquid scintillation counting. Filtration and washing are carried out using a conventional vacuum filtration cell harvester. The specific binding (defined as the difference between the total binding and the non-specific binding) in the presence of the particular test compound is determined and compared with the control value. Results are conveniently expressed as the negative logarithm of the concentration required to cause a 50% displacement of control specific binding (pIC$_{50}$).

In general, compounds of the formula I showing antagonist activity in this assay typically show a pIC$_{50}$ in the above test (a) of 6 or more. Thus for example, the compound of Example 1 herein shows a pIC$_{50}$ of about 8, and the compound of Example 119 herein shows a pIC$_{50}$ of about 8.5. The compound of Example 180 shows a PIC$_{50}$ of 7.6. Using the same test procedure, the known compound 1,3-dimethylxanthine typically shows a pIC$_{50}$ of about 5.

(b) Guinea-pig Aortic Constriction Test

This test has been described by Collis et al. (*British J. Pharmacology*, 1989, 97, 1274–1278) and involves the assessment of the ability of a test compound to antagonise the attenuatory effect of adenosine on phenylephrine induced constriction of a guinea-pig aortic ring preparation, an effect mediated via the adenosine receptor known as A$_2$.

The aortic ring preparation is obtained as follows: Sections (3–5 mm) of guinea pig thoracic aorta (from Dunkin Hartley strain, 250–400 g males) are mounted in organ baths containing oxygenated Krebs solution (95% $O_2$: 5% $CO_2$) at 37° C. [The nucleoside transport inhibitor, dipyridamole (10 μM) is present in the Krebs solution]. The isometric tension development is recorded and the tissue placed under a resting tension of 1 g and allowed to equilibrate for 1 hour. The aortic ring preparation is then sensitised to $10^{-5}$M phenylephrine. Erythro-9-(2-hydroxy-3-nonyl)adenine (EHNA) (10 μM) is added to the preparation and after 10 minutes the tissue is constricted to approximately 50% maximum by adding $3 \times 10^{-6}$M phenylephrine. Adenosine is next added cumulatively ($10^{-7}$M to $10^{-3}$M) and the evoked relaxation is measured. After washout for 20 minutes, a $10^{-5}$M solution of the test compound in DMSO (maximum 1% by volume) diluted with Krebs solution is added and left to equilibrate for 30 minutes. Twenty minutes into the equilibration period further EHNA (10 μM) is added to the preparation and 10 minutes later phenylephrine ($3 \times 10^{-6}$M) is introduced to produce constrictive tone again. A repeat dose response curve to adenosine is then carried out followed by washout.

Test compounds are assessed by plotting the percentage relaxation observed against the logarithm of the adenosine concentration, competitive adenosine antagonism producing a parallel shift in the standard adenosine concentration/relaxation (dose response) curve. The dose ratio (DR) is calculated from the ratio of the concentration of adenosine to produce a 50% relaxation (ED$_{50}$) in the presence of the test antagonist divided by the ED$_{50}$ concentration of adenosine in the absence of the test antagonist for each aortic ring. Significant antagonist activity in this assay is indicated by a DR of >2. The pA2 value, which is an estimate of the concentration of antagonist to give a dose ratio of 2, may also be calculated using a standard computation technique. In general, compounds of formula I showing antagonist activity in this assay have a pA2 of 6 or more. Thus, the compound of Example 1 herein has a pA2 of 7.4; and the compound of Example 119 herein has a pA$_2$ of 7.3. Using the same test procedure the known compound, 1,3-dimethylxanthine, has a pA2 of about 5.

(c) Guinea-pig Atrial Bradycardic Test

This test has also been described by Collis et al. (*British J. Pharmacology*, 1989, 97, 1274–1278) and involves the ability of a test compound to antagonise the bradycardic effect of the adenosine mimetic, 2-chloroadenosine, in a beating guinea-pig atrial preparation, an effect mediated via the adenosine receptor known as A$_1$.

The atrial pair preparation may be obtained as follows: Atrial pairs are obtained from guinea-pigs (Dunkin Hartley strain, 250–400 g males) and mounted in organ baths containing oxygenated Krebs buffer solution (95% $O_2$; 5% $CO_2$) at 37° C. The spontaneously beating atria are then placed under a resting tension of 1 g and allowed to equilibrate for 50 minutes with continuous overflow. Overflow is then stopped and adenosine deaminase (1Unitml) added to prevent the accumulation of endogenously produced adenosine. After equilibration for 15 minutes, a cumulative dose response curve to the adenosine mimetic, 2-chloroadenosine ($10^{-8}$M to $10^{-4}$M) is administered to produce a maximal slowing of atrial rate. After washout during 30 minutes, adenosine deaminase is readministered to the bath which is allowed to equilibrate for 15 minutes. A $10^{-5}$M solution of the test compound in DMSO is then added to the bath which is left to incubate for 30 minutes. Any effect on the beating rate due to the test compound is noted before the dose response curve to 2-chloroadenosine is repeated. Compounds which are adenosine antagonists attenuate the 2-chloroadenosine response.

Test compounds are assessed by comparing dose response curves to 2-chloroadenosine alone with those obtained in the presence of the compound. Competitive adenosine antagonists produce a parallel shift in the 2-chloroadenosine dose response curve. The dose ratio (DR) is calculated from the ratio of the concentration of 2-chloroadenosine to produce a 50% reduction in atrial rate ($ED_{50}$) in the presence of the test compound divided by the $ED_{50}$ concentration of 2-chloroadenosine in the absence of the test compound for each atrial pair. The pA2 is then obtained in an analogous manner to that referred to in (b) above. In general, compounds of formula I showing antagonist activity in this assay have a pA2 of about 6. Thus the compound of Example 1 herein has a pA2 of 6.2 and the compound of Example 119 herein has a pA2 of 6.0. The compound of Example 180 has a pA2 of 5.5. Similarly, the known compound, 1,3-dimethylxanthine, typically shows a pA2 of about 5.

(d) Anaesthetised Cat Blood Pressure Test

This test assesses the ability of a test compound to antagonise the fall in diastolic blood pressure produced by administration of the adenosine mimetic, 2-chloroadenosine.

Male cats (2–3 kg) are anaesthetised with sodium pentobarbitone (45 mg/kg, ip). The following blood vessels are catheterised: right jugular vein (for infusion of the anaesthetic at approximately 7 mg/kg per hour as a 3 mg/ml solution in isotonic saline), the left jugular vein (for administration of test agents) and the right common carotid artery (for monitoring blood pressure and pulse rate). The blood gas status and pH are determined, and are maintained within physiological limits, before administration of 2-chloroadenosine. A control dose response curve (DRC) to 2-chloroadenosine (0.3 to 30 µg/kg) against the fall in diastolic blood pressure is determined. A solution of the test compound in a mixture of 50% v/v polyethylene glycol (PEG) 400 and 0.1M sodium hydroxide is then administered i.v. and after 15 minutes the DRC to 2-chloroadenosine is determined. This procedure is repeated twice with blood gases and pH being monitored and maintained within physiological limits between each DRC. The concentration of 2-chloroadenosine required to cause a 30 nun Hg fall in diastolic blood pressure is then calculated for each dose of test compound and a Schild plot constructed for those which produce a dose ratio (DR) of >2. From this plot a $K_B$ value is determined. In general compounds of formula I showing activity in this test possess a $K_B$ of 1 mg/kg (or much less). For example the compound of Example 1 has a $K_B$ of 30 µg/kg and the compound of Example 119 has a $K_B$ of 0.7 mg/kg.

The above Test (d) may conveniently be modified to allow evaluation of orally administered test compounds by administering the test compound to conscious cats with indwelling arterial and venous catheters and measuring the effect in preventing an adenosine induced decrease in blood pressure. Those compounds of formula I which show oral activity, for example the compound of Example 1, show significant adenosine antagonist activity at a dose of 1–3 mg/kg or less without any sign of overt toxicity at several times the minimum effective dose.

(e) Anaesthetised Dog Test

This test involves the assessment of the effects of a test compound on antagonising the actions of adenosine in lowering heart rate and increasing vasodilation (as measured by a fall in hind-limb perfusion pressure).

Beagles (12–18 kg) are anaesthetised with sodium pentobarbitone (50 mg/kg, iv). The following blood vessels are catheterised: right jugular vein (for infusion of the anaesthetic at approximately 112 mg per hour as a 3 mg/ml solution in isotonic saline), right brachial vein (for administration of drugs and test agents), right brachial artery (for measurement of systemic blood pressure and pulse rate) and the left carotid artery (for administration of adenosine into the left ventricle). Both vagi, the right femoral and sciatic nerves are ligated and severed. A bolus injection of 1250 U heparin is administered before perfusing the right hindlimb at constant blood flow with blood from the iliac artery. The right leg is tied just below the ankle. Xamoterol (1 mg/kg) is then administered to the animal to stabilise heart rate at a high level and nitrobenzylthioinosine (NBTI, 0.5 mg/kg) to inhibit the uptake of adenosine. The animal is sensitised to adenosine during the equilibration time following NBTI by carrying out a dose response curve (DRC). During this time any blood gas or pH imbalance is corrected. A control DRC is performed followed by up to three DRC's after cumulative administration of the test compound (as described in (d) above). Each DRC is carried out 15 minutes after administration of test compound and after the measured parameters of heart rate and hindlimb perfusion pressure have returned to a stable state. Similarly, blood gases and pH are maintained within physiological limits throughout the evaluation.

The amount of adenosine required to cause a 50% fall in measured parameter ($ED_{50}$) i.e. heart rate and hindlimb perfusion pressure is calculated for each does of test compound and a Schild plot constructed. From this plot a $K_B$ value is determined for antagonism of heart rate response and vasodilator response to adenosine. In general, compounds of formula I showing activity in this test possess a $K_B$ of 1 mg/kg (or much less) for antagonism of vasodilator response to adenosine with no indication of toxic or other untoward properties at doses several times greater than the minimum effective dose. For example the compound of Example 1 has a $K_B$ of 30 µg/kg and the compound of Example 119 has a $K_B$ of 1.1 mg/kg. The compound of Example 180 has been found to give a $K_B$ in the range of from 0.01–0.24 mg/kg.

f) Anaesthetised Cat Exercise Hyperaemia Test

This test involves assessment of the effect of a test compound to antagonise the vasodilatation response which occurs during twitch contraction of skeletal muscle. The vasodilation is mediated partly by the release of endogenous adenosine from the contracting skeletal muscle.

Cats (2.4–3.6 kg) are anaesthetised with sodium pentobarbitone (50 mg.kg$^{-1}$ ip). The following blood vessels are catheterized: left jugular vein (for infusion of anaesthetic, at approximately 0.12 mg$^{-1}$min$^{-1}$ as a 6 mg.ml$^{-1}$ solution in isotonic saline), right external jugular vein (for administration of drugs and test compounds), right common carotid artery (for measurement of systemic arterial blood pressure and pulse rate) and right brachial artery (for withdrawal of blood).

Blood flow to the left hind limb is measured with an electromagnetic flow probe around the left external iliac artery. The whole of the left hind limb is made to contract at 3 Hz for 20 minutes duration by stimulating the sciatic and femoral nerves. Active tension produced by the extensor digitorum longus and peroneous longus muscles is measured isometrically with a force transducer. Exercise is repeated twice within the same animal, in either the absence or presence of the test compound. Test compounds are assessed for their ability to reduce the vasodilatation during skeletal muscle contraction.

In general, compounds of formula I, for example the compound of Example 1, produce significant inhibition of vasodilatation during exercise over the range, 0.1-1 mg.kg$^{-1}$. The known compound, 1,3-dimethylxanthine, produces significant inhibition at 10 mg.kg$^{-1}$.

In general, the majority of compounds of formula I show activity as adenosine antagonists which is predominantly selective for adenosine $A_2$ receptors.

The compounds of the invention are generally best administered to warm-blooded animals for therapeutic or prophylactic purposes in the treatment or prevention of cardiovascular diseases and adverse conditions in the form of a pharmaceutical composition comprising said compound of formula I or a pharmaceutically acceptable salt thereof, in admixture or together with a pharmaceutically acceptable diluent or carrier. Such compositions are provided as a further feature of the invention.

In general, it is envisaged that a compound of formula I will be administered orally, intravenously or by some other medically acceptable route (such as by inhalation, insufflation, sub-lingual or transdermal means) so that a dose in the general range, for example, 0.001 mg to 10 (and more particularly in the range, for example, 0.05 to 5 mg/kg) mg/kg body weight is received. However, it will be understood that the precise dose administered will necessarily vary according to the nature and severity of the disease or condition being treated and on the age and sex of the patient.

A composition according to the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose from containing, for example, 5-200 mg of the compound of formula I or an equivalent amount of a pharmaceutically acceptable salt thereof.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise the contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example: a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at room temperature, that is in the range 18°-26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet; q,quartet; and (vi) all end-products were characterised by microanalysis, NMR and/or mass spectroscopy.

EXAMPLE 1

Phenol (6.4 g) and 1,8-diazabicyclo[5.4.0]undec-7-ene (DBU, 3.8 ml) were added to a suspension of 7-amino-2-(2-furyl)-5-methylsulphonyl-[1,2,4]triazolo[1,5-a][1,3,5]triazine (6.4 g) in dimethoxyethane (150 ml) and the resulting mixture was heated under reflux for 1 hour, after which time thin layer chromatographic (TLC) analysis on silica plates (eluant: 5-10% v/v ethyl acetate in dichloromethane) indicated that no methylsulphonyl starting material remained. The solvent was evaporated and the residue was purified by column chromatography on silica (250 g) eluting with an increasing amount of ethyl acetate in dichloromethane (5-10% v/v). The colourless amorphous solid (5.4 g) thereby obtained was crystallised from ethanol to give 7-amino-2-(2-furyl)-5-phenoxy-[1,2,4]triazolo[1,5-a][1,3,5]triazine (3.4 g) as colourless fluffy crystals, m.p. 250°-252° C.; microanalysis, found: C,56.7; H,4.1; N,26.2%; $C_{14}H_{10}N_6O_2$. 0.5$C_2H_5OH$ requires: C,56.8; H,4.1; N,26.5%; NMR: 1.05 (t, 1.5H, $CH_3CH_2OH$), 3.45(q, 1H, $CH_3CH_2OH$), 4.3(br s, 0.5H, $\overline{CH_3CH_2O}H$), 6.7 (dd, 1H, furyl-4$\underline{H}$), 7.1(d, 1H, furyl-3$\underline{H}$), 7.3(m, 3$\underline{H}$, phenoxy), 7.4(m, 2$\underline{H}$, phenoxy), 7.9(d, 1$\underline{H}$, furyl-5$\underline{H}$), 8.8-9.1(d, 2H, N$\underline{H}_2$); m/e 294 (M$^+$).

The necessary starting material was prepared as follows:

(1) Hydrogen chloride gas (20.0g) was bubbled into an ice-cooled mixture of 2-furonitrile (46.5 g) and absolute ethanol (23.0 g). After addition of the gas, solid crystallised from the mixture. The crystalline solid was collected by filtration and heated in pyridine (300 ml) with aminoguanidine nitrate (56.0 g) under reflux for 4 hours. The mixture was cooled, solid material removed by filtration and the filtrate evaporated to give crude 3-amino-5-(2-furyl)-1,2,4-triazole. This material was purified by treatment with nitric acid (400 ml of 50% v/v). The crystalline salt which formed was collected by filtration, washed sequentially with water (100 ml) and ethanol (50 ml) and air dried to give 3-amino-5-(2-furyl)-1,2,4-triazole nitrate (45.0 g), m.p. 130°-133° C. (decomp.). Several batches (184.0 g) of this salt (184 g) were suspended in hot water (400 ml) and sodium carbonate (46.0 g) was added in portions. The basic solution obtained was allowed to cool to give 3-amino-5-(2-furyl)-1,2,4-triazole (82.0 g) as colourless prisms, m.p. 204–206° C.; NMR 6.05(s, 2H, $NH_2$), 6.6(s, 1H, furyl-4$\underline{H}$), 6.7(s, 1H, furyl-3$\underline{H}$), 7.7(s,1$\underline{H}$, furyl-5$\underline{H}$), 12.05(br s,1H N$\underline{H}$).

(2) An intimate mixture of 3-amino-5-(2-furyl)-1,2,4-triazole (33.0 g) and dimethyl N-cyanodithioiminocarbonate (33.0 g) was heated at 170° C. for 1 hour, under a slow stream of argon. After cooling, the resulting solid was purified by column chromatography on silica (600 g) eluting with an increasing amount of ethyl acetate in dichloromethane (5–10% v/v) to give 7-amino-2-(2-furyl)-5-methylthio-[1,2,4]triazolo[1,5-a][1,3,5]triazine as a colourless solid (11.1 g), essentially pure by TLC, which was used without further purification. [A small amount of the above solid was recrystallised from ethanol to give, crystals, m.p. 238°–240° C.; microanalysis, found: C,44.0; H,3.3; N,33.7; $C_9H_8N_6SO$. $0.05C_2H_5OH$ requires C,43.6; H,3.3; N,33.6; NMR 1.05 and 3.4 (t+q, ethanol of crystallisation), 2.5 (s, 3H, $CH_3S$—), 6.7(dd, 1H, furyl-4$\underline{H}$), 7.2(d, 1H, furyl-3$\underline{H}$), 7.7(d, 1H, furyl-5$\underline{H}$) 8.7–9.0(br d, 2H, $N\underline{H}_2$); m/e 248 ($M^+$).

(3) A solution of 3-chloroperoxybenzoic acid (50% strength, 45.0 g) in dichloromethane (300 ml) was added to a stirred,ice-cooled suspension of 7-amino-2-(2-furyl)-5-methylthio-[1,2,4]triazolo[1,5-a][1,3,5]triazine (8.0 g) in dichloromethane (300 ml). The residual aqueous layer was discarded. The resulting suspension was allowed to warm to ambient temperature and stirred for 16 hours. The solvent was evaporated and ethanol (150 ml) was added to the residue. The suspension obtained was left to stand for 30 minutes with occasional swirling. The solid was then collected by fitration, washed with ethanol and dried to give 7-amino-2-(2-furyl)-5-methylsulphonyl-[1,2,4]triazolo[1,5-a][1,3,5]triazine (6.6 g) as colourless solid, NMR: 3.3(s, 3H), $CH_3.SO_2$), 6.7(q, 1H, furyl-4$\underline{H}$), 7.3(q, 1H, furyl-3$\underline{H}$), 7.9(q, 1H, furyl-5$\underline{H}$ ), 9.4–9.8(d, 2H, $N\underline{H}_2$), which was used without further purification.

EXAMPLE 2

Thiophenol (0.4 ml) and DBU (0.7 ml) were added to a suspension of 7-amino-2-(2-furyl)-5-methylsulphonyl-[1,2,4]triazolo [1,5-a][1,3,5]triazine (1.0 g) in acetonitrile (50 ml) and the resulting suspension was heated under reflux for 16 hours. The solvent was evaporated and the residue was purified by column chromatography on silica (75 g) eluting sequentially with dichloromethane and then ethyl acetate in dichloromethane (1:9 v/v) to give the product as an amorphous solid (0.4 g). This was crystallised from ethanol to give 7-amino-2-(2-furyl)-5-thiophenoxy-[1,2,4]triazolo[1,5-a][1,3,5]triazine as colourless prisms (0.25 g), m.p. 301°–302° C.; microanalysis, found: C,54.4; H,3.1; N,27.3%; $C_{14}H_{10}N_6SO$ requires: C,54.2; H,3.2; N,27.1%; NMR: 6.7(dd, 1H, furyl-4$\underline{H}$), 7.1(d, 1H, furyl-3$\underline{H}$), 7.5(m, 3H, thiophenoxy), 7.65(m, 2H, thiophenoxy), 7.9(d, 1H, furyl-5$\underline{H}$), 8.8–9.0(d, 2H, $N\underline{H}_2$); m/e 310 ($M^+$).

EXAMPLE 3

Propylamine (6.0 ml) was added to a stirred suspension of 7-amino-2-(2-furyl)-5-methylsulphonyl-[1,2,4]triazolo[1,5-a][1,3,5]triazine (2.0 g) in acetonitrile (30 ml) and stirring was continued for 4 hours. The solvent was evaporated and the residue was purified by chromatography on silica (100 g) eluting with dichloromethane containing methanol (2.5% v/v). The solid (0.85 g) obtained was crystallised from t-butyl acetate to give 7-amino-2-(2-furyl)5-(propylamino)-[1,2,4]triazolo[1,5-a][1,3,5]triazine as a crystalline solid (0.5 g), m.p. 197°–198° C.; microanalysis, found: C,53.2; H,6.1; N,31.1%; $C_{11}H_{13}N_7O$. $0.5C_6H_{12}O_2$ requires: C,53.0; H,6.0; N,30.9%; NMR: 0.9(t,3H, $C\underline{H}_3CH_2CH_2$), 1.4(s, 4.5H, t-butyl acetate), 1.5–1.7(m, 2$\overline{H}$, $CH_3C\underline{H}_2$—), 1.9(s, 1.5H, t-butyl acetate), 3.25(t, 2H, $CH_3CH_2C\underline{H}_2$—), 6.7(dd, 1H, furyl-4$\underline{H}$), 7.0(d, 1H, furyl-3$\underline{H}$), 7.4(br t, 1H, —N$\underline{H}$—), 7.8(q, 1H, furyl-5$\underline{H}$), 7.9–8.3(br d, 2H, $N\underline{H}_2$); m/e 260 $(M+H)^+$.

EXAMPLE 4

A solution of 4-amino-3-(2-furyl)-6-phenoxy-[1,2,4]triazolo[4,3-a][1,3,5]triazine (0.65 g) in absolute ethanol (40 ml) was heated under reflux for 1 hour. The resulting solution was concentrated to half-volume in vacuo and allowed to crystallise to give 7-amino-2-(2-furyl)-5-phenoxy-[1,2,4]triazolo[1,5-a][1,3,5]triazine (0.35 g) as fluffy crystals, m.p. 253°–255° C.; microanalysis, found: C,56.7; H,4.3; N,25.6%; $C_{14}H_{10}N_6O_2$. $0.75C_2H_5OH$ requires: C,56.6; H,4.4; N,25.6%; NMR: 1.0(t, ca. 2H, $CH_3C\underline{H}_2OH$); 3.4(q, ca. 1.5H, $C\underline{H}_3CH_2OH$), 4.3(br s, ca. 0.75H, $CH_3CH_2O\underline{H}$), 6.7(dd, 1H, furyl-4$\underline{H}$), 7.1(d, 1H, 3-furyl H), 7.2–7.4(m, 3H, Ar$\underline{H}$), 7.5(m, 2H, Ar$\underline{H}$), 7.9(d, 1H, furyl-5$\underline{H}$), 8.8–9.1(br d, 2$\overline{H}$, $N\underline{H}_2$); m/e 294 ($M^+$).

The starting material was prepared as follows:

Diphenyl cyanocarbonimidate (13.6 g) was added to a stirred suspension of 3-amino-5-(2-furyl)-1,2,4-triazole (75.0 g) in acetonitrile (250 ml). The resulting suspension was stirred for 72 hours and then heated under reflux for 1 hour. The solvent was evaporated and the residue was purified by chromatography on silica (600 g), eluting first with ethyl acetate in dichloromethane (1:9 v/v) and then with methanol in dichloromethane (1:19 v/v) to give 4-amino-3-(2-furyl)-6-phenoxy-[1,2,4]triazolo[4,3-a][1,3,5]triazine as a colourless solid. This solid was recrystallised from acetonitrile to give material with m.p. 195°–197° C., (followed by resolidification and remelting at 250°–255° C.); microanalysis, found: C,57.3; H,3.0; N,28.3%; $C_{14}H_{10}N_6O_2$ requires: C,57.1; H,3.4; N,28.6%; NMR: 6.7(dd, 1H, furyl-4$\underline{H}$), 7.1(d, 1H, furyl-3$\underline{H}$), 7.2–7.4(m, 3H, Ar$\underline{H}$), 7.4–7.6(m, 2H, Ar$\underline{H}$), 8.0 (d, 1H, furyl-5$\underline{H}$), 6.8–9.7 (br, $N\underline{H}^2$); m/e 294 ($M^+$).

EXAMPLE 5

Using an analgous procedure to that described in Example 2, but starting from 7-amino-2-(5-methyl-2-furyl)-5-methylsulphonyl-[1,2,4]triazolo[1,5-a][1,3,5]triazine obatined from the corresponding 5-methylthio compound described in Example 47 below, there was obtained 7-amino-2-[2-(5-methylfuryl)]-5-phenylthio-[1,2,4]triazolo[1,5-a][1,3,5]triazine, as a solid, m.p. 311°–313° C., microanalysis, found: C, 55.6; H, 3.6; N, 26.3%; $C_{15}H_{12}N_6OS$ requires: C, 55.5; H, 3.7; N, 25.9%; NMR: 2.37(s, 3H, C$\underline{H}_3$), 6.30(d, 1H, furyl-4$\underline{H}$), 7.0(d, 1H, furyl-3$\underline{H}$), 7.5(m, 3H, phenyl o+p-$\underline{H}$), 7.63(m, 2H, phenyl m-$\underline{H}$) and 8.88(br s, 2H, N$\underline{H}_2$); m/e 325 (M+H)+.

EXAMPLE 6

A solution of 7-amino-2-(2-furyl)-5-methylsulphonyl[1,2,4]triazolo[1,5-a][1,3,5]triazine (1.6 g) in ethanol (40 ml) containing DBU (1.0 ml) was heated under reflux until no starting material remained by TLC analysis. The solvent was removed by evaporation and the residue purified by chromatography on silica using 5–10% v/v ethyl acetate in dichloromethane as eluant, followed by crystallisation from ethanol to give 7-amino-5-ethoxy-2-(2-furyl)[1,2,4]triazolo[1,5-a][1,3,5]triazine as hygroscopic crystals, m.p. 211°–213° C.; microanalysis, found: C, 48.7; H, 4.5; N, 31.4; $H_2O$, 1.2%; $C_{10}H_{10}N_6O_2$. $0.33C_2H_5OH$. $0.165H_2O$ requires: C, 48.4; H, 4.7; N, 31.8; $H_2O$, 1.1%; NMR: 1.05(t, 1H, CH$_3$C$\underline{H}_2$OH), 1.35(t, 3H, C$\underline{H}_3$ CH$_2$), 3.4(q, C$\underline{H}_3$CH$_2$OH), 4.3(q, 2H, CH$_3$C$\underline{H}_2$O—), 6.7(dd, 1H, furyl-4$\underline{H}$), 7.1(d, 1H, furyl-3$\underline{H}$), 7.9(d, 1H, furyl-5$\underline{H}$), 8.5–9.0(d, 2H, N$\underline{H}_2$); m/e 246 (M+).

EXAMPLES 7-9

Using a similar procedure to that described in Example 1, but using the appropriate substituted phenol or benzyl alcohol instead of phenol, the following compounds were prepared:

EXAMPLE 7

7-amino-5-(4-chlorophenoxy)-2-(2-furyl)-[1,2,4]triazolo[1,5-a][1,3,5]triazine, as colourless prisms (crystallised from 2-propanol), m.p.294°–295° C.; microanalysis, found: C, 52.0; H, 3.8; N, 22.2; Cl, 9.7%; $C_{14}H_9N_6ClO_2$. $0.66C_3H_7OH$ requires: C, 52.1; H, 3.9; N, 22.8; Cl, 9.6%; NMR: 1.05(d, 4H, CH$_3$), 3.8(m, ⅔H, C$\underline{H}$OH), 4.3(d, 2/3H, O$\underline{H}$), 6.7(dd, 1H, furyl-4$\underline{H}$), 7.1(d, 1$\underline{H}$, furyl-3$\underline{H}$), 7.3(m, 2H, phenoxy), 7.5(m, 2$\underline{H}$, phenoxy), 7.9(d, 1H, furyl-5$\underline{H}$), 8.8–9.2(d, 2H, N$\underline{H}_2$); m/e 328, 330 (M+).

EXAMPLE 8

7-amino-5-benzyloxy-2-(2-furyl)-[1,2,4]triazolo[1,5-a][1,3,5]triazine as colourless prisms (crystallised from ethanol), m.p. 256°–258° C.; microanalysis, found: C, 58.1; H, 4.0; N, 27.2%; $C_{15}H_{12}N_6O_2$ requires: C, 58.4; H, 3.9; N, 27.3%; NMR: 5.4 (s, 2H, C$\underline{H}_2$), 6.7(dd, 1H, furyl-4$\underline{H}$), 7.1(d, 1H, furyl-3$\underline{H}$), 7.3–7.5(m, 5H, phenyl), 7.9(d, 1$\underline{H}$, furyl-5$\underline{H}$), 8.6–9.0(d, 2H, N$\underline{H}_2$); m/e 308 (M+); and

EXAMPLE 9

7-amino-5-(4-benzyloxyphenoxy)-2-(2-furyl)-[1,2,4]triazolo[1,5-a][1,3,5]triazine as colourless crystals (crystallised from ethanol), m.p. 260°–262° C.; microanalysis, found: C, 62.1; H, 4.7; N, 19.7%; $C_{21}H_{16}N_6O_3$. $0.66C_2H_5OH$ requires: C, 62.5; H, 4.2; N, 19.6%; NMR: 1.05(t, 2H, C$\underline{H}_3$), 3.4(q, CH$_3$C$\underline{H}_2$), 4.3(t, CH$_3$CH$_2$O$\underline{H}$), 5.1(s, 2H, phenyl.C$\underline{H}_2$), 6.7(dd, 1H, furyl-4$\underline{H}$), 7.0–7.2(m, 5H, phenyl), 7.3–7.5(m, 5H, phenyl), 7.9(d, 1H, furyl-5$\underline{H}$), 8.7–9.1(d, 2H, N$\underline{H}_2$); m/e 400 (M+).

EXAMPLE 10

A solution of 7-amino-5-(4-benzyloxyphenoxy)-2-(2-furyl)[1,2,4]triazolo[1,5-a][1,3,5]triazine (1.0 g) in methanol (400 ml) containing palladium-on-carbon catalyst (10% w/w, 200 mg) and acetic acid (20 ml) was treated with hydrogen gas at atmospheric pressure. The reaction was monitored by tlc analysis (system as Example 1) and once no further starting material was detected, the catalyst was removed by filtration. Solvent was evaporated from the filtrate. The solid residue obtained was crystallised from ethanol to give 7-amino-2-(2-furyl)-5-(4-hydroxyphenoxy)-[1,2,4]triazolo[1,5-a][1,3,5]triazine as colourless hygroscopic crystals, m.p. 292°–294° C.; microanalysis, found: C, 53.5; H, 3.6; N, 26.4; $H_2O$, 2.1%; $C_{14}H_{10}N_6O_3$ $0.33H_2O$ requires: C, 53.2; H, 3.4; N, 26.6; H, 3.6; N, 26.4; $H_2O$, 2.1%; NMR: 6.7(dd, 1H, furyl-4$\underline{H}$), 6.8(d, 2H, phenyl), 7.0(d, 2H, phenyl), 7.1(d, 1$\underline{H}$, furyl-3$\underline{H}$), 7.9(d, 1H, furyl-5$\underline{H}$), 8.7–9.1(d, 2H, N$\underline{H}_2$), 9.4(br s, 1H, O$\underline{H}$; m/e 310 (M+).

EXAMPLE 11-17

Using a procedure similar to that described in Example 1, but using the appropriate substituted phenol or alcohol instaed of phenol, the following compounds were obtained:

EXAMPLE 11

7-amino-2-(2-furyl)-5-(4-methoxyphenoxy)-[1,2,4]triazolo[1,5-a][1,3,5]triazine as colourless fluffy crystals (crystallised from ethanol), m.p. 264°–265° C.; microanalysis, found: C, 55.7; H, 3.6; N, 25.6%; $C_{15}H_{12}N_6O_3$ requires: C, 55.5; H, 3.7; N, 25.9%; NMR: 3.8(s, 3H, —OC$\underline{H}_3$), 6.7(dd, 1H, furyl-4$\underline{H}$), 7.0(m, 2H, phenyl), 7.2(m, 3$\underline{H}$, phenyl+furyl-3$\underline{H}$), 7.9(d, 1H, furyl-5$\underline{H}$), 8.8–9.1(d, 2H, N$\underline{H}_2$): m/e 324 (M+);

EXAMPLE 12

7-amino-5-(3-fluorophenoxy)-2-(2-furyl)-[1,2,4]triazolo[1,5-a][1,3,5]triazine as colourless crystals (crystallised from ethanol), m.p. 271°–273° C.; microanalysis, found: C, 54.1; H, 2.8; N, 26.6; $C_{14}H_9N_6FO_2$ requires: C, 53.8; H, 2.9; N, 26.9%; NMR 6.7(dd, 1H, furyl-4$\underline{H}$), 7.1–7.3(m, 4H, phenoxy+furyl-3$\underline{H}$), 7.4–7.6(m, 1H, phenoxy), 7.9(d, 1H, furyl-5$\underline{H}$), 8.8–9.2(d, 2H, N$\underline{H}_2$); m/e 312 (M+);

EXAMPLE 13

7-amino-2-(2-furyl)-5-(2-phenylethoxy)-[1,2,4]triazolo[1,5-a][1,3,5]triazine as colourless crystals (crystallised from ethanol), m.p. 198°–200° C.; microanalysis, found: C, 59.5; H, 4.2; N, 26.0%; $C_{16}H_{14}N_6O_2$ requires: C, 59.6; H, 4.3; N, 26.1%; NMR: 3.1 (t, 2H, phenyl.C$\underline{H}_2$), 4.5(t, 2H, C$\underline{H}_2$O), 6.7(dd, 1H, furyl-4$\underline{H}$), 7.1(d, 1$\underline{H}$, furyl-3$\underline{H}$), 7.2–7.4(m, 5H, phenyl), 7.9(d, 1$\underline{H}$, furyl-5$\underline{H}$), 8.6–9.0(d, 2H, N$\underline{H}_2$); m/e 323 (M+H)+;

EXAMPLE 14

7-amino-2-(2-furyl)-5-(2-phenoxyethoxy)-[1,2,4]triazolo[1,5-a][1,3,5]triazine as colourless crystals (crystallised from ethanol), m.p. 255°–257° C.; microanalysis, found: C, 57.1; H, 4.3, N, 24.4%; $C_{16}H_{14}N_6O_3$ requires: C, 56.8; H, 4.1; N, 24.8%; NMR: 4.3(m, 2H, phenoxy.CH$_2$C$\underline{H}_2$), 4.6(m, 2H, phenoxy. OC$\underline{H}_2$), 6.7(dd, 1H, furyl-4$\underline{H}$), 7.0(m, 3H, phenoxy), 7.1(d, 1H, furyl-3$\underline{H}$), 7.3(m, 2$\underline{H}$, phenoxy), 7.9(d, 1H, furyl-5$\underline{H}$), 8.7–9.0(d, 2H, N$\underline{H}_2$); m/e 339 (M+H)$^+$;

EXAMPLE 15

7-amino-2-(2-furyl)-5-(2-methoxyethoxy)-[1,2,4]triazolo[1,5-a][1,3,5]triazine as colourless crystals, m.p. 232°–234° C.; microanalysis, found: C, 48.2; H, 4.5; N, 30.4%; $C_{11}H_{12}N_6O_3$ requires: C, 47.8; H, 4.3; N, 30.5%; NMR: 3.7(m, 2H, CH$_3$OC$\underline{H}_2$), 4.4(m, 2H, CH$_3$OCH$_2$C$\underline{H}_2$), 6.7(dd, 1H, furyl-4$\underline{H}$), 7.1(d, 1H, furyl-3$\underline{H}$), 7.9(d, 1$\underline{H}$, furyl-5$\underline{H}$), 8.6–9 0(d, 2$\underline{H}$, N$\underline{H}_2$), m/e 277 (M+H)$^+$;

EXAMPLE 16

7-amino-5-(4-cyanophenoxy)-2-(2-furyl)-[1,2,4]triazolo[1,5-a][1,3,5]triazine, as colourless crystals (crystallised from ethanol), m.p. >285° C.; microanalysis, found: C, 56.6; H, 2.8; N, 30.9%; $C_{15}H_9N_7O_2$ requires: C, 56.4; H, 2.8; N, 30.7%; NMR: 6.7(dd, 1H, furyl-4$\underline{H}$), 7.1(d, 1H, furyl-3$\underline{H}$), 7.5(d, 2H, phenoxy-$\underline{H}$), 7.8–8.0(q+d, 3H, phenoxy+furyl-5$\underline{H}$), 8.8–9.2(d, 2$\underline{H}$, N$\underline{H}_2$); m/e 319 (M$^+$); and

EXAMPLE 17

7-amino-5-butoxy-2-(2-furyl)-[1,2,4]triazolo[1,5-a][1,3,5]triazine as colourless crystals (crystallised from ethanol), m.p. 177°–178° C.; microanalysis, found: C, 52.6; H, 4.8; N, 30.4%; $C_{12}H_{14}N_6O_2$ requires: C, 52.5; H, 5.i; N, 30.6%; NMR: 1.0(t, 3H, C$\underline{H}_3$), 1.4(m, 2H, CH$_3$C$\underline{H}_2$), 1.7(m, 2H, C$\underline{H}_2$CH$_2$O), 4.3(t, 2H, C$\underline{H}_2$O), 6.7(dd, 1H, furyl-4$\underline{H}$), 7.1(d, 1H, furyl-3$\underline{H}$), 7.9(d, 1H, furyl-5$\underline{H}$), 8.5–8.9(d, 2H, N$\underline{H}_2$); m/e 274 (M$^+$).

EXAMPLES 18–19

Using a similar procedure to that described in Example 6, but using 3-methoxyphenol or allyl alcohol instead of ethanol, there were obtained:

EXAMPLE 18

7-amino-2-(2-furyl)-5-(3-methoxyphenoxy)-[1,2,4]triazolo[1,5-a][1,3,5]triazine was obtained as colourless crystals (crystallised from ethanol), m.p. 226°–227° C.; microanalysis, found: C, 55.6; H, 3.6; N, 25.5%; $C_{15}H_{12}N_6O_3$ requires: C, 55.5; H, 3.7; N, 25.9%; NMR: 3.8(s, 3H, C$\underline{H}_3$), 6.7(dd, 1H, furyl-4$\underline{H}$), 6.8(m, 3H, phenoxy), 7.1(d, 1H, furyl-3$\underline{H}$), 7.35(m, 1H, phenoxy), 7.9(d, 1H, furyl-5$\underline{H}$) 8.8–9.1(d, 2H, N$\underline{H}_2$); m/e 324 (M$^+$); and

EXAMPLE 19

5-allyloxy-7-amino-2-(2-furyl)-[1,2,4]triazolo[1,5-a][1,3,5]triazine as colourless crystals (crystallised from ethanol), m.p. 169°–171° C., microanalysis, found: C, 51.5; H, 3.8; N, 32.5%; $C_{11}H_{10}N_6O_2$ requires: C, 51.4; H, 3.5; N, 32.7%; NMR 4.8 (m, 2H, C$\underline{H}_2$O), 5.2–5.5(m, 2H, CH$_2$=CH.C$\underline{H}_2$O), 6.0–6.2(m, 1$\underline{H}$, CH$_2$=C$\underline{H}$.CH$_2$O), 6.7(dd, 1H, furyl-4$\underline{H}$), 7.1(d, 1H, furyl-3$\underline{H}$), 7.9(d, 1H, furyl-5$\underline{H}$), 8.6–9.0(d, 2H, N$\underline{H}_2$); m/e 258 (M$^+$).

EXAMPLES 20–25

Using a similar procedure to that described in Example 1, but starting from the appropriate hydroxy compound instead of phenol, there were obtained the following compounds:

EXAMPLE 20

7-amino-2-(2-furyl)-5-(2-methoxyphenoxy)-[1,2,4]triazolo[1,5-a][1,3,5]triazine as colourless crystals (crystallised from ethanol), m.p. 221°–222° C., microanalysis, found: C, 55.2; H, 3.7; N, 25.0; H$_2$O, 0.7%; $C_{15}H_{12}N_6O_3$. 0.1$C_2H_5OH$. 0.125$H_2O$ requires: C, 55.2; H, 3.7; N, 25.0; H$_2$O, 0.7%; NMR: 3.8(s, 3H, C$\underline{H}_3$), 6.7(dd, 1H, furyl-4$\underline{H}$), 6.9–7.4(m, 5H, phenoxy+furyl-3$\underline{H}$), 7.9(d, 1H, furyl-5$\underline{H}$), 8.7–9.2(d, 2H, N$\underline{H}_2$); NMR spectrum also contains C$_2$H$_5$OH (0.1 mole); m/e 324 (M$^+$);

EXAMPLE 21

7-amino-5-(2-fluorophenoxy)-2-(2-furyl)-[1,2,4]triazolo[1,5-a][1,3,5]triazine as colourless crystals (crystallised from ethanol), m.p. 252°–253° C.; microanalysis, found: C, 53.4; H, 3.3; H, 25.8; H$_2$O, 1.2%; $C_{14}H_9N_6FO_2$. 0.125$C_2H_5OH$. 0.2$H_2O$ requires: C, 53.2; H, 3.2; N, 26.1; H$_2$O, 1.1%; NMR: 6.7(dd, 1H, furyl-4$\underline{H}$), 7.1(d, 1H, furyl-3$\underline{H}$), 7.2–7.5(m, 4H, phenoxy), 7.9(d, 1H, furyl-5$\underline{H}$), 8.8–9.3(d, 2H, N$\underline{H}2$); m/e 312 (M$^+$);

EXAMPLE 22

7-amino-2-[2-furyl]-5-(2-phenylthioethoxy)-[1,2,4]triazolo[1,5-a][1,3,5]triazine as colourless crystals (crystallised from ethanol), m p. 216°–218° C.; microanalysis, found: C, 54.4; H, 3.8; N, 23.3%; $C_{16}H_{14}N_6SO_2$ requires: C, 54.2; H, 4.0; N, 23.7%; NMR: 3.4(t, 2H, SC$\underline{H}_2$), 4.4(t, 3H, OC$\underline{H}_2$), 6.7(dd, 1H, furyl-4$\underline{H}$), 7.1(d, 1H, furyl-3$\underline{H}$), 7.2–7.5(m, 5H, phenyl), 7.9(d, 1H, furyl-5$\underline{H}$), 8.6–9.0(d, 2H, N$\underline{H}_2$); m/e 355 (M+H$^+$);

EXAMPLE 23

7-amino-5-(4-fluorophenoxy)-2-(2-furyl)-[1,2,4]triazolo[1,5-a][1,3,5]triazine as colourless crystals (crystallised from ethanol) m.p. 277°–278° C.; microanalysis, found: C, 53.2; H, 3.2; N, 24.7; H$_2$O, 1.2%; $C_{14}H_9N_6FO_2$. 0.4$C_2H_5OH$. 0.25 $H_2O$ requires: C, 53.0; H, 3.6; N, 25.1; H$_2$O, 1.3%; NMR: 1.05(t, CH$_3$CH$_2$OH), 3.45(q+d, CH$_3$C$\underline{H}_2$OH), 4.3(t, CH$_3$CH$_2$O$\underline{H}$), 6.7(dd, 1H, furyl-4$\underline{H}$), 7.1(d, 1H, furyl-3$\underline{H}$), 7.3(d, 4H, phenoxy), 7.7(d, 1H, furyl-5$\underline{H}$), 9.0(br s, 1H, N$\underline{H}_2$); m/e 313, (M+H)$_+$;

EXAMPLE 24

7-amino-5-(2-cyanophenoxy)-2-(2-furyl)-[1,2,4]triazolo[1,5-a][1,3,5]triazine as colourless crystals (crystallised form methanol), m.p. >290° C.; microanalysis, found: C, 56.7; H, 2.5; N, 30.9%; $C_{15}H_9N_7O_2$ requires: C, 56.4; H, 2.8; N, 30.7%; NMR: 6.7(dd, 1H, furyl-4$\underline{H}$), 7.1(d, 1H, furyl-3$\underline{H}$), 7.5(m, 2H, phenoxy), 7.8–8.1(m, 3H, furyl-5$\underline{H}$+phenoxy), 9.2(br s, 2H, N$\underline{H}_2$); m/e 320 (M+H)$^+$; and

EXAMPLE 25

7-amino-2-(2-furyl)-5-(3-isoxazolyloxy)-[1,2,4]triazolo[1,5-a][1,3,5]triazine as colourless crystals (crystallised from 2-propanol), m.p. 274°–275° C.; microanalysis, found: C, 46.4; H, 2.4; N, 34.1%; $C_{11}H_7N_7O_3$ requires: C, 46.3; H, 2.5; N, 34.4%; NMR 6.7(dd, 1H, furyl-4$\underline{H}$), 6.75(d, 1H, isoxazole-4$\underline{H}$), 7.2(d, 1H, furyl-3$\underline{H}$), 7.9(d, 1H, furyl-5$\underline{H}$), 8.9(d, 1H, isoxazole-5$\underline{H}$), 9.0–9.4(br s, 2H, N$\underline{H}_2$); m/e 286 (M+H)$^+$.

EXAMPLES 26–40

Using a procedure similar to that described in Example 3, but using the appropriate amine instead of propylamine, the following compounds of formula I were obtained:

EXAMPLE 26

7-amino-5-cyclohexylamino-2-(2-furyl)-[1,2,4]triazolo[1,5-a][1,3,5]triazine as pale cream prisms, (crystallised from 2-propanol), m.p. 278°–280° C. (decomposition); microanalysis, found: C, 56.5; H, 5.7; N, 31.8%; $C_{14}H_{17}N_7O$. $0.125 C_3H_7OH$ requires: C, 56.3; H, 5.9; N, 32.0%; NMR: 1.05(d, $CH_3$), 3.8(m, CHOH), 4.3(d, $CHOH$), 1.1–1.4(complex, 5H, $CH_2$), 1.5–1.9-(complex, 5H, $CH_2$), 3.75(m, 1H, $NHCH$), 6.68(q, 1H, furyl-4H), 7.05(q, 1H, furyl-5H), 7.25(1H, d, $NH$), 7.88(d, 1H, furyl-3H), 7.95–8.3(complex, 2H, $NH_2$); m/e 299 ($M^+$);

EXAMPLE 27

7-amino-2-(2-furyl)-5-phenylamino-[1,2,4]triazolo[1,5-a][1,3,5]triazine as pale yellow plates (crystallised from ethanol), m.p. 280° C.; microanalysis, found: C, 57.3; H, 3.5; N, 33.1%; $C_{14}H_{11}N_7O$ requires: C, 57.3; H, 3.8; N, 33.4%; NMR: 6.7(q, 1H, furyl-4H), 7.0(t, 1H, p-phenyl-$H$), 7.1(q, 1H, furyl-3H), 7.3(t, 2H, m-phenyl-$H$), 7.8(d, 2H, o-phenyl-$H$), 7.88(d, 1H, furyl-5H), 8.4(br, 2H, $NH_2$) and 9.63(s, 1H, $NH$); m/e 294 $(M+H)^+$;

EXAMPLE 28

5-allylamino-7-amino-2-(2-furyl)-[1,2,4]triazolo[1,5-a][1,3,5]triazine as pale yellow crystals (crystallised from ethyl acetate), m.p. 182°–184° C.; microanalysis, found: C, 51.5; H, 4.3; N, 37.9%; $C_{11}H_{11}N_7O$ requires: C, 51.4; H, 4.3; N, 38.1%; NMR: 3.95(complex, 2H, $CH_2N$), 5.07(dd, 1H, =CH), 5.17(dd, 1H, =CH), 5.91(m, 1H, =$CH.CH_2$), 6.68(dd, 1H, furyl-4H), 7.05(d, 1H, furyl-3H), 7.56(br, 1H, $NH$), 7.86(d, 1H, furyl-5H) and 8.0–8.4(complex, 2H, $NH_2$); m/e 242, 257 ($M^+$);

EXAMPLE 29

7-amino-2-(2-furyl)-5-pyrrolidino-[1,2,4]triazolo[1,5-a][1,3,5]triazine as a solid (crystallised from ethanol), m.p. >300° C. (decomposition); microanalysis found: C, 53.4; H, 4.8; N, 35.9%; $C_{12}H_{13}N_7O$ requires: C, 53.1; H, 4.8; N, 36.2%; NMR: 1.91(complex, 4H, $CH_2CH_2$), 3.50(br, 4H, $CH_2NCH_2$), 6.65(dd, 1H, furyl-4H), 7.03(d, 1H, furyl-3H), 7.83(m, 1H, furyl-5H) and 8.19(br, 2H, $NH_2$); m/e 271 ($M^+$);

EXAMPLE 30

7-amino-2-(2-furyl)-5-morpholino-[1,2,4]triazolo[1,5-a][1,3,5]triazine as a solid (crystallised from ethanol), m.p. >300° C.; microanalysis, found: C, 50.6; H, 4.3; N, 34.4%; $C_{12}H_{13}N_7O_2$ requires: C, 50.2; H, 4.6; N, 34.1%; NMR: 3.64–3.75(complex, 4H, $CH_2$), 6.67(dd, H, furyl-4H), 7.05(d, 1H, furyl-3H), 7.86(m, 1H, furyl-5H) and 8.32(br s, 2H, $NH_2$); m/e 288 $(M+H)^+$;

EXAMPLE 31

7-amino-5-benzylamino-2-(2-furyl)-[1,2,4]triazolo[1,5-a][1,3,5]triazine as pale yellow plates (crystallised from ethanol), m.p. 222°–224° C.; microanalysis, found: C, 58.8; H, 4.1; N, 1.9%; $C_{15}H_{13}N_7O$ requires: C, 58.6; N, 4.3; N, 31.9%; NMR: 4.52(d, 2H, $CH_2N$), 6.65(dd, 1H, furyl-4H), 7.04(d, 1H, furyl-3H), 7.15–7.4(complex, 5H, phenyl), 7.85(d, 1H, furyl-5H), 7.93(t, 1H, $NH$) and 8.16(br, 2H, $NH_2$); m/e 307 ($M^+$);

EXAMPLE 32

7-amino-5-butylamino-2-(2-furyl)-[1,2,4]triazolo[1,5-a][1,3,5]triazine as a solid (crystallised from 2-propanol), m.p. 220°–221° C.; microanalysis, found: C, 52.9; H, 5.6; N, 35.5%; $C_{12}H_{15}N_7O$ requires: C, 52.7; H, 5.5; N, 35.9%; NMR: 0.90(t, 3H, $CH_3$), 1.32(q, 2H, $CH_2CH_3$), 1.50(m, 2H, $CH_2CH_2CH_3$), 3.32(m, $CH_2N$), 6.66(d, 1H, furyl-4H), 7.04(s, 1H, furyl-3H), 7.38(br s, 1H, $NH$), 7.84(s, 1H, furyl-5H) and 8.05(br s, 2H, $NH_2$); m/e 274$(M+H)^+$;

EXAMPLE 33

7-amino-5-ethylamino-2-(2-furyl)-[1,2,4]triazolo[1,5-a][1,3,5]triazine as colourless prisms (crystallised from ethanol), m.p. 230°–232° C.; microanalysis, found: C, 49.4; H, 4.2; N, 40.0%; $C_{10}H_{11}N_7O$ requires: C, 49.0; H, 4.5; N, 40.0%; NMR 1.12(t, 3H, $CH_3$), 3.32(m, $CH_2$), 6.67(dd, 1H, furyl-4H), 7.03(d, 1H, furyl-3H), 7.38(t, 1H, $NH$), 7.86(d, 1H, furyl-5H) and 8.07(br, 2H, $NH_2$); m/e 245 ($M^+$);

EXAMPLE 34

7-amino-2-(2-furyl)-5-isopropylamino-[1,2,4]triazolo[1,5-a][1,3,5]triazine as colourless prisms (crystallised from ethanol), m.p 226°–8° C.; microanalysis, found: C, 51.4; H, 5.0; N, 37.5%; $C_{11}H_{13}N_7O$ requires: C, 51.0; H, 5.1; N, 37.8%; NMR 1.15(d, 6H, $CH_3$), 4.08(m, 1H, $CH.N$), 6.66(dd, 1H, furyl-4H), 7.03(d, 1H, furyl-3H), 7.26(br, 1H, $NH$), 7.84(d, 1H, furyl-5H) and 8.03(br, 1H, $NH_2$); m/e 259$(M^+)$;

EXAMPLE 35

7-amino-2-(2-furyl)-5-(2-phenylethyl)amino-[1,2,4]triazolo[1,5-a][1,3,5]triazine as pale cream crystals (crystallised from ethanol), m.p. 258°–260° C.; microanalysis, found: C, 60.1; H, 4.8; N, 30.5%; $C_{16}H_{15}N_7O$ requires: C, 59.8; H, 4.7; N, 30.5%; NMR: 2.86(t, 2H, $CH_2Ph$), 3.50(q, 2H, $CH_2NH$), 6.68(dd, 1H, furyl-4H), 7.66(d, 1H, furyl-3H), 7.1–7.4(complex, 5H, $ArH$), 7.45(br t, 1H, $NH$), 7.87(d, 1H, furyl-5H) and 8.12(br, 2H, $NH_2$); m/e 321 ($M^+$);

EXAMPLE 36

7-amino-2-(2-furyl)-5-(2-furyl)methylamino-[1,2,4]triazolo[1,5-a][1,3,5]triazine as pale cream crystals (crystallised from ethanol), m.p. 196°–198° C.; microanalysis, found: C, 52.8, H, 4.6, N, 30.3%; $C_{13}H_{11}N_7O_2$. $0.66 C_2H_5OH$ requires: C, 52.5; H, 4.6; N, 29.9%; NMR: 1.06(t, $CH_3$), 3.45(m, $CH_2$), 4.31(t, $OH$), 4.49(d, 2H, $CH_2N$), 6.28(s, 1H, furylmethyl-3H), 6.37(dd, 1H, furylmethyl-4H), 6.66(dd, 1H, furyl-4H), 7.05(d, 1H, furyl-3H), 7.54(s, 1H, furylmethyl-5H), 7.85(br s, 2H, furyl-5H+$NH$) and 8.18(br, 2H, $NH_2$); m/e 297 ($M^+$);

EXAMPLE 37

(S)-7-amino-5-[α-methylbenzylamino]-2-(2-furyl)-[1,2,4]triazolo[1,5-a][1,3,5]triazine as a solid (crystallised from toluene), m.p. 136°–140° C.; microanalysis, found: C, 62.1; H, 5.1; N, 28.3%; $C_{16}H_{15}N_7O$. $0.3 C_7H_8$ requires: C, 62.3; H, 5.0; N, 28.1%; NMR 1.44(d, 3H, $CH_3$), 2.29(s, Ph.$CH_3$), 5.18(t, 1H, $CHN$), 6.65(dd, 1H, furyl-4H), 7.03(d, 1H, furyl-3H), 7.1–7.5(complex, 5H, phenyl), 7.83(s, 1H, furyl-5H), 7.94(d, 1H, $NH$) and 8.09(s, 2H, $NH_2$); m/e 322 $(M+H)^+$;

EXAMPLE 38

7-amino-5-isobutylamino-2-(2-furyl)-[1,2,4]triazolo[1,5-a][1,3,5]triazine as a solid (crystallised from ethyl acetate), m.p. 244°–245 °C.; microanalysis, found: C, 52.9; H, 5.5; N, 36.1%; $C_{12}H_{15}N_7O$ requires: C, 52.7; H, 5.5; N, 35.9%; NMR: 0.89(d, 6H, $CH_3$), 1.88[m, 1H, $CH(CH_3)_2$], 3.09(t, 2H, $CH_2N$), 6.65(dd, 1H, furyl-4$\underline{H}$), 7.03(d, 1H, furyl-3$\underline{H}$), 7.43(t, 1H, N$\underline{H}$), 7.84(d, 1H, furyl-5$\underline{H}$) and 8.03(br s, 2H, N$\underline{H}_2$); m/e 274 (M+H)$^+$;

EXAMPLE 39

7-amino-5-dimethylamino-2-(2-furyl)-[1,2,4]triazolo[1,5-a][1,3,5]triazine as a solid (crystallised from 2-propanol), m.p. >298° C.; microanalysis, found: C, 49.4; H, 4.1; N, 39.9%; $C_{10}H_{11}N_7O$ requires: C, 49.0; H, 4.5; N, 40.0%; NMR: 3.13(s, 6H, $CH_3$), 6.65(dd, 1H, furyl-4$\underline{H}$), 7.03(d, 1H, furyl-3$\underline{H}$), 7.8(s, 1H, furyl-5$\underline{H}$) and 8.22(br s, 2H, N$\underline{H}_2$); m/e 246(M+H)$^+$; and

EXAMPLE 40

7-amino-5-(2-dimethylaminoethyl)amino-2-(2-furyl)[1,2,4]triazolo[1,5-a][1,3,5]triazine as colourless prisms, m.p. 233°–235 °C.; microanalysis, found: C, 50.3; H, 5.8; N, 38.7%; $C_{12}H_{16}N_8O$ requires: C, 50.0; H, 5.6; N, 38.9%; NMR: 2.20[s, 6H, $N(CH_3)_2$], 3.48(m, $CH_2CH_2NH$); 6.66(dd, 1H, furyl-4$\underline{H}$), 7.04(d, 1H, furyl-3$\underline{H}$), 7.20(br, 1H, NH), 7.85(s, 1H, furyl-5$\underline{H}$) and 8.09(br, 2H, N$\underline{H}_2$).

EXAMPLES 41–44

Using a procedure similar to that described in Example 2, the following compounds of formula I were obtained starting with the appropriate thiol:

EXAMPLE 41

7-amino-5-cyclopentylthio-2-(2-furyl)-[1,2,4]triazolo[1,5-a][1,3,5]triazine as a solid (crystallised from methanol), m.p. 213°–214° C.; microanalysis, found: C, 51.9; H, 4.4; N, 28.1.%; $C_{13}H_{14}N_6SO$ requires: C, 51.7; H, 4.6; N, 27.8%; NMR: 1.63(m, 6H, $CH.CH_2CH_2.CH$), 2.21(m, 2H, CH), 3.98(m, 1H, C$\underline{H}$-S), 6.70(dd, 1H, furyl-4$\underline{H}$), 7.16(dd, 1H, furyl-3$\underline{H}$), 7.90(m, 1H, furyl-5$\underline{H}$) and 8.80(br d, 2H, N$\underline{H}_2$); m/e 302 (M$^+$);

EXAMPLE 42 methyl 5-(7-amino-2-(2-furyl)-[1,2,4]triazolo[1,5-a][1,3,5]triazine)thioacetate as a solid (crystallised from methanol), m.p. 265°–267° C. (decomposition); microanalysis, found: C, 43.2; H, 3.3; N, 27.5%; $C_{11}H_{10}N_6SO_3$ requires: C, 43.1; H, 3.3; N, 27.4%; NMR: 3.69(s, 3H, $CH_3$), 4.06(s, 2H, $CH_2S$), 6.71(dd, 1H, furyl-4$\underline{H}$), 7.18(d, 1H, furyl-3$\underline{H}$), 7.92(m, 1H, furyl-5$\underline{H}$) and 8.92(br s, 2H, N$\underline{H}_2$); m/e 302 (M$^+$);

EXAMPLE 43

7-amino-2-(2-furyl)-5-(2-furyl)methylthio-[1,2,4]triazolo[1,5-a][1,3,5]triazine as a solid (crystallised from methanol), m.p. 246°–247° C.; microanalysis, found: C, 49.9; H, 3.1; N, 26.3%; $C_{13}H_{10}N_6O_2S$ requires: C, 49.7; H, 3.2; N, 26.7%; NMR: 4.46(s, 2H, $CH_2$.S), 6.39(m, 2H, furylmethyl 3$\underline{H}$+4$\underline{H}$), 6.70(dd, 1H, furyl-4$\underline{H}$), 7.17(d, 1H, furyl-3$\underline{H}$), 7.56(s, 1H, furylmethyl 5-$\underline{H}$), 7.90(s, 1H, furyl-5$\underline{H}$) and 8.90(br d, 2H, N$\underline{H}_2$); m/e 314 (M$^+$); and

EXAMPLE 44

7-amino-5-benzylthio-2-(2-furyl)-[1,2,4]triazolo[1,5-a][1,3,5]triazine as a solid, (crystallised from ethanol), m.p. 273°–275° C.; microanalysis, found: C, 55.8; H, 3.6; N, 25.9%; $C_{15}H_{12}N_6OS$ requires: C, 55.5; H, 3.7; N, 25.9%; NMR: 4.41(s, 2H, $CH_2S$), 6.70(dd, 1H, furyl-4$\underline{H}$), 7.18(d, 1H, furyl-3$\underline{H}$), 7.2–7.6(complex, 5H, phenyl-$\underline{H}$), 7.91(m, 1H, furyl-5$\underline{H}$) and 8.81(br d, 2H, N$\underline{H}_2$), m/e 291, 324 (M$^+$);

EXAMPLES 45–47

Using a similar procedure to that described in part 2 of Example 1 the following compounds were obtained:

EXAMPLE 45

7-amino-2-(3-furyl)-5-methylthio-[1,2,4]triazolo[1,5-a][1,3,5]triazine as a solid (crystallised from methanol), m.p. 279°–281° C.; microanalysis, found: C, 43.1; H, 3.3; N, 33.7%; $C_9H_8N_6OS$ requires: C, 43.5; H, 3.2; N, 33.9%; NMR: 2.50(s, $SCH_3$), 6.93(d, 1H, furyl-4$\underline{H}$), 7.83(t, 1H, furyl-5$\underline{H}$), 8.30(d, 1H, 2-furyl $\underline{H}$) and 8.74(br d, 2H, N$\underline{H}_2$);

EXAMPLE 46

7-amino-2-(5-chloro-2-furyl)-5-methylthio-[1,2,4]triazolo[1,5-a][1,3,5]triazine as a solid (crystallised from ethanol), m.p. 273°–275° C.; NMR: 2.50,(s, 3H, $SCH_3$), 6.73(d, 1H, furyl-4$\underline{H}$), 7.23(d, 1H, furyl-3$\underline{H}$), 8.86 (br d, 2H, N$\underline{H}_2$); and

EXAMPLE 47

7-amino-2-(5-methyl-2-furyl)-5-methylthio-[1,2,4]triazolo[1,5-a][1,3,5]triazine as a solid (crystallised from ethanol), m.p. 266°–268° C.; microanalysis, found: C, 46.2; H, 3.6; N, 32.1%; $C_{10}H_{10}N_6OS$ requires: C, 45.8; H, 3.8; N, 32.1%; NMR 2.38(s, 3H, $CH_3$), 2.50(s, $SCH_3$), 6.31(d, 1H, furyl-4$\underline{H}$), 7.04(d, 1H, furyl-3$\underline{H}$) and 8.80(d, 2H, N$\underline{H}_2$); m/e 263 (M+H)$^+$.

EXAMPLES 48–51

Using a similar procedure to that described in Example 1 but starting from the appropriate methylthio derivative and phenol, there were obtained the following compounds of formula I:

EXAMPLE 48

7-amino-2-(3-furyl)-5-phenoxy-[1,2,4]triazolo[1,5-a][1,3,5]triazine as a solid (crystallised from methanol), m.p. 286°–287° C. (decomposition); microanalysis, found: C, 57.5; H, 3.3; N, 28.6%; $C_{14}H_{10}N_6O_2$ requires: C, 57.1; H, 3.4; N, 28.6%; NMR: 6.91(m, H, furyl-4$\underline{H}$), 7.25(m, 3H, phenyl o-+p-$\underline{H}$), 7.83(t, 1H, furyl-5$\underline{H}$), 8.27(s, 1H, furyl-2$\underline{H}$) and 8.86(d, 2H, N$\underline{H}_2$); m/e 294 (M)$_+$;

EXAMPLE 49

7-amino-2-(5-chloro-2-furyl)-5-(2-fluorophenoxy)-[1,2,4]triazolo[1,5-a][1,3,5]triazine as a solid (crystallised from ethanol), m.p. 286°–288° C.; microanalysis, found: C, 48.5; H, 2 2; N, 24.1%; $C_{14}H_8ClFN_6O_2$ requires: C, 48.5; H, 2.3; N, 24.2%; NMR: 6.72(d, 1H, furyl-4$\underline{H}$), 7.18(d, 1H, furyl-3$\underline{H}$), 7.2–7.5(complex, 4H, phenyl) and 9.08(br s, 2H, N$\underline{H}_2$); m/e 346, (M)$^+$;

EXAMPLE 50

7-amino-2-(5-methyl-2-furyl)-5-phenoxy-[1,2,4]triazolo[1,5-a][1,3,5]triazine as a solid (crystallised from ethanol), m.p. 227°–228° C.; microanalysis, found: C, 57.8; H, 4.3; N, 25.3%; $C_{15}H_{12}N_6O_2$ 0.5 $C_2H_5OH$ requires: C, 58.0; H, 4.5; N, 25.4%; NMR 2.38(s, 3H, $CH_3$), 6.31(d, 1H, furyl-4$\underline{H}$), 7.00(d, 1H, furyl-3$\underline{H}$), 7.25(complex, 3H, phenyl $\underline{o}$-+$\underline{p}$-$\underline{H}$), 7.45(t, 2H, phenyl $\underline{m}$-$\underline{H}$) and 8.94(br d,2H, N$\underline{H}_2$);

EXAMPLE 51

7-amino-5-(2-methoxyethoxy)-2-(5-methyl-2-furyl)-[1,2,4]triazolo[1,5-a][1,3,5]triazine as a solid (crystallised form ethanol), m.p. 220°–222° C.; microanalysis, found: C, 50.0; H, 4.6; N, 29.0%; $C_{12}H_{14}N_6O_3$ requires C, 49.6; H, 4.8; N, 29.0%; NMR 2.37 (s, 3H, $CH_3$), 3.30(s, $CH_3$), 3.65(t, 2H, $CH_2OCH_3$), 4.41(t, 2H, $CH_2CH_2O$), 6.30(m, 1H, furyl-4$\underline{H}$), 7.01(d, 1H, furyl-3$\underline{H}$) and 8.75(br d, 2H, N$\underline{H}_2$); m/e 291 (M+H)+.

EXAMPLES 52–54

Using a similar procedure to that described in Example 3 but starting from the appropriate methylthio derivative and amine, there were obtained the following compounds of formula I:

EXAMPLE 52

7-amino-5-cyclohexylamino-2-(3-furyl)-[1,2,4]triazolo[1,5-a][1,3,5]triazine as a solid (crystallised from methanol), m.p. 254°–256° C. (decomposition); microanalysis, found: C, 56.4; H, 5.7; N, 32.8%; $C_{14}H_{17}N_7O$ requires C, 56.2; H, 5.7; N, 32.8%; NMR: 1.0–1.4(complex, 5H, $CH_2$), 1.5–2.0(complex, 5$\underline{H}$, $CH_2$), 3.74(br s, 1H, CHN), 6.88(m, 1H, furyl-4$\underline{H}$), 7.2–7.4- (complex t and d rotamers, 1H, CHN$\underline{H}$), 7.81(t, 1H, furyl-5$\underline{H}$), 7.95(br s, 2H, N$\underline{H}_2$) and 8.22(s, 1H, furyl-2$\underline{H}$); m/e 299 (M)+;

EXAMPLE 53

7-amino-2-(5-chloro-2-furyl)-5-cyclohexylamino-[1,2,4]triazolo[1,5-a][1,3,5]triazine as a solid (crystallised from ethanol), m.p >300° C. microanalysis, found: C, 50.8; H, 4.6; N, 28.4%; $C_{14}H_{16}ClN_7O$. $0.2C_2H_5OH$ requires: C, 50.5; H, 4.9; N, 28.6%; NMR: 1.1–1.9(complex, 10H, $CH_2$), 3.74(br s, 1H, C$\underline{H}$N), 6.68(d, 1H, furyl-4$\underline{H}$), 7.09(d, 1H, furyl-3$\underline{H}$), 7.32(complex, 1H, N$\underline{H}$) and 8.06(s, 2H, N$\underline{H}_2$); m/e 333, (M)+; and

EXAMPLE 54

7-amino-2-(5-methyl-2-furyl)-5-propylamino-[1,2,4]triazolo[1,5-a][1,3,5]triazine as a solid (crystallised from ethanol), m.p. 230°–231° C.; microanalysis, found: C, 53.1; H, 5.5; N, 35.8%; $C_{12}H_{15}N_7O$ requires: C, 52.7; H, 5.5; N, 35.9; NMR: 0.89(t, 3H, $CH_3$), 1.52(m, 2H, $CH_2$), 2.36(s, 3H, $CH_3$), 3.20(m, 2$\underline{H}$, $CH_2N$), 6.26(m, 1H, furyl-4$\underline{H}$), 6.91(d, 1H, furyl-3$\underline{H}$), 7.35(br s, 1H, N$\underline{H}$) and 8.01(br s, 2H, N$\underline{H}_2$).

EXAMPLES 55–58

Using a similar procedure to that described in Example 2 but starting with the appropriate methylthio derivative and thiophenol, the following compounds of formula I were obtained:

EXAMPLE 55

7-amino-2-(3-furyl)-5-phenylthio-[1,2,4]triazolo[1,5-a][1,3,5]triazine as a solid (crystallised from methanol), m.p. 297°–298° C. (decomposition); microanalysis, found: C, 54.2; H, 3.1; N, 26.6%; $C_{14}H_{10}N_6OS$, $0.05CH_3OH$ requires: C, 54.1; H, 3.3; N, 26.95%; NMR: 6.91(d, 1H, furyl-4$\underline{H}$), 7.47–7.66(complex, 5H, phenyl), 7.83(t, H, furyl-5$\underline{H}$), 8.27(s, 1H, furyl-2$\underline{H}$) and 8.83(br d, 2H, N$\underline{H}_2$); m/e 311 (M+H)+;

EXAMPLE 56

7-amino-5-(4-fluorophenylthio)-2-(3-furyl)-[1,2,4]triazolo[1,5-a][1,3,5]triazine as a solid (crystallised from ethanol), m.p. 314°–315° C. (decomposition); microanalysis, found: C, 51.5; H, 2.8; N, 25.4%; $C_{14}H_{19}FN_6OS$ requires: C, 51.2; H, 2.7; N, 25.6%; NMR: 6.90(d, 1H, furyl-4$\underline{H}$), 7.32(t, 2H, phenyl), 6.67(m, 2H, phenyl), 7.81(t, 1H, furyl-5$\underline{H}$), 8.26(s, 1H, furyl-2$\underline{H}$) and 8.83(br d, 2H, N$\underline{H}_2$); m/e 328 (M)+;

EXAMPLE 57

7-amino-5-cyclopentylthio-2-(3-furyl)-[1,2,4]triazolo[1,5-a][1,3,5]triazine as a solid (crystallised from methanol), m.p. 260°–261° C.; microanalysis, found: C, 52.0; H, 4.8; N, 28.2%; $C_{13}H_{14}N_6OS$ requires C, 51.7; H, 4.6; N, 27.8%; NMR: 1.5–1.80(complex, 6H, $CH_2$), 2.21(m, 2H, $CH_2SCH_2$), 3.98(m, 1H, CHS), 6.96(d, 1H, furyl-4$\underline{H}$), 7.35(t, 1H, furyl-5$\underline{H}$), 8.32(s, 1H, furyl-2$\underline{H}$) and 8.72(br d, 2H, N$\underline{H}_2$); m/e 303 (M+H)+; and

EXAMPLE 58

7-amino-2-(5-chloro-2-furyl)-5-phenylthio-[1,2,4]triazolo[1,5-a][1,3,5]triazine as a solid (crystallised from ethanol), m.p. >300° C.; microanalysis, found: C, 48.6; H, 2.4; N, 24.2%; $C_{14}H_9ClN_6O_5$ requires: C, 48.7; H, 2.6; N, 24.4%; NMR 6.72(d, 1H, furyl-4$\underline{H}$), 7.18(d, 1H, furyl-3$\underline{H}$), 7.51(complex, 3H, phenyl $\underline{o}$+$\underline{p}$-$\underline{H}$), 7.64(complex, 2H, phenyl $\underline{m}$-$\underline{H}$) and 9.04(br d, 2$\underline{H}$, N$\underline{H}_2$); m/e 345 (M+H)+.

EXAMPLE 59

Using a similar procedure to that described in part 2 of Example 1, 7-amino-5-methylthio-2-(2-thienyl)-[1,2,4]triazolo[1,5-a][1,3,5]triazine was obtained as a solid (crystallised from methanol), m.p. 263°–265° C. (decomposition); microanalysis, found: C, 40.7; H, 3.7; N, 29.5%; $C_9H_8N_6S_2$. $0.6CH_3OH$ requires: C, 40.8; H, 3.7; N, 29.8%; NMR: 2.51(s, $SCH_3$), 3.18(s, $CH_3OH$), 7.23(dd, 1H, thienyl-4$\underline{H}$), 7.77(complex, 2H, thienyl-3$\underline{H}$+5$\underline{H}$) and 8.77(br d, 2H, N$\underline{H}_2$); m/e 264(M+).

EXAMPLES 60–61

Using a similar procedure to that described in Example 1, but using the appropriate methylthio derivative and phenol, there were obtained the following compounds of formula I:

EXAMPLE 60

7-amino-5-phenoxy-2-(2-thienyl)-[1,2,4]triazolo[1,5-a][1,3,5]triazine as a solid, m.p. 285°–287° C., after recrystallisation from ethanol; microanalysis, found: C, 54.4; H, 3.2; N, 26.5%; $C_{14}H_{10}N_6OS$ requires: C, 54.2; H, 3.2; N, 26.8%; NMR: 7.25(complex, 4H, phenyl+-thienyl-4$\underline{H}$), 7.45(t, 2H, phenyl), 7.77(complex, 2H, thienyl-3$\underline{H}$+5$\underline{H}$) and 8.9(br d, 2H, N$\underline{H}_2$); m/e 310 (M+); and

EXAMPLE 61

7-amino-5-(2-methoxyphenoxy)-2-(2-thienyl)-[1,2,4]triazolo[1,5-a][1,3,5]triazine as a solid, m.p. 257°–259° C., after recrystallisation from ethanol; microanalysis, found: C, 52.9; H, 3.3; N, 24.6%; $C_{15}H_{12}N_6O_2S$ requires: C, 53.0; H, 3.5; N, 24.7%; NMR 3.74(s, 3H, $CH_3O$), 6.99(m, 1H, thienyl-4$\underline{H}$), 7.1–7.3-

(complex, 4H, phenyl), 7.74(m, 2H, thienyl-3H+5H) and 8.81(br d, 2H, NH$_2$); m/e 341 (M+H)$^+$.

EXAMPLE 62–63

Using a similar procedure to that described in Example 3, but using the appropriate methylthio derivative and amino compound, there were obtained the following compounds of formula I:

EXAMPLE 62

7-amino-5-cyclohexylamino-2-(2-thienyl)-[1,2,4]triazolo[1,5-a][1,3,5]triazine as a solid, m.p. 2892°–91° C.; microanalysis, found: C, 52.5; H, 5.3; N, 30.4%; C$_{14}$H$_{17}$N$_7$S 0.25 H$_2$O requires: C, 52.5; H, 5.5; N, 30.6%; NMR 1.0–2.0(complex, 10H, CH$_2$), 3.73(br s, 1H, CHN), 7.21(dd, 1H, thienyl-4H), 7.26(m, 1H, NH), 7.72(m, 2H, thienyl-3H,5H) and 7.99(br s, 2H, NH$_2$); m/e 316 (M+H$^+$); and

EXAMPLE 63

7-amino-5-propylamino-2-(2-thienyl)-[1,2,4]triazolo[1,5-a][1,3,5]triazine as a solid, m.p. 225°–6° C., after recrystallisation from ethanol; microanalysis, found: C, 48.5; H, 4.7; N, 35.5%; CH$_{11}$H$_{13}$N$_7$S (0.1 C$_2$H$_5$OH) requires: C, 48.1; H, 4.9; N, 35.1%; NMR 0.89(t, 3H, CH$_3$), 1.54(m, 2H, CH$_2$), 3.24(m, 2H, CH$_2$N), 7.18(dd, 1H, thienyl-4H), 7.40(t, 1H, NH), 7.70(m, 2H, thienyl-3H,5H) and 7.99(br s, 2H, NH$_2$); m/e 276 (M+H)$^+$.

EXAMPLE 64

Using a similar procedure to that described in Example 2 but starting from 7-amino-5-methylthio-2-(2-thienyl)-[1,2,4]triazolo[1,5-a][1,3,5]triazine and using thiophenol, there was obtained 7-amino-5-phenylthio-2-(2-thienyl)-[1,2,4]triazolo[1,5-a][1,3,5]triazine as a solid, m.p. >300° C. (decomposition); microanalysis, found: C, 51.9; H, 3.1; N, 25.6%; C$_{14}$H$_{10}$N$_6$S$_2$ requires: C, 51.5; H, 3.1; N, 25.8%; NMR 7.20(dd, 1H, thienyl-4H), 7.4–7.8(complex, 1H, phenyl-H, thienyl-3H,5H) and 8.83(d, 2H, NH$_2$).

EXAMPLES 65–80

Using a procedure similar to that described in Example 3, but using the appropriate amine instead of propylamine, the following compounds of formula I were obtained:

EXAMPLE 65

7-amino-2-(2-furyl)-5-(3-pyridylmethyl)amino[1,2,4]-triazolo[1,5-a][1,3,5-]triazine as colourless prisms (crystallised from methanol), m.p. 261°–262° C.; microanalysis, found: C,54.7; H,3.8; N,36.3%; C$_{14}$H$_{12}$N$_8$O requires: C,54.5; H,3.9; N,36.4%; NMR: 4.5(d,2H, CH$_2$), 6.5(q,1H, furyl-4H), 7.0(s,1H, furyl-3H), 7.3(complex, 1H, pyridyl-5H), 7.75(d,1H, pyridyl-4H), 7.85(s,1H, furyl-5H), 8.0(broad s,1H), NH), 8.2(broad d,2H, NH$_2$), 8.45(d,1H, pyridyl-6H), 8.55(s,1H, pyridyl-2H) m/e 309 (M+H)$^+$.

EXAMPLE 66

7-amino-2-(2-furyl)-5-n-pentylamino-[1,2,4]triazolo[1,5-a][1,3,5]triazine as colourless prisms (crystallised from ethanol), m.p. 219°–220° C.; microanalysis, found: C,54.6; H,6.1; N,33.9%; C$_{13}$H$_{17}$N$_7$O requires: C,54.3; H, 6.01N,34.1%; NMR: 0.9(t,3H, CH$_3$),1.2–1.4(complex, 4H, CH$_2$CH$_2$), 1.55(complex, 2H CH$_2$CH$_2$N), 3.2(t,2H, CH$_2$N), 6.65(q,1H, furyl-4H), 7.05(d,1H, furyl-3H), 7.3–7.5(complex, 1H, NH), 7.85(q,1H, furyl-5H), 7.9–8.4(broad d, 2H, NH$_2$); m/e 287 (M+).

EXAMPLE 67

7-amino-5-cyclopropylmethylamino-2-(2-furyl)-[1,2,4]triazolo[1,5-a][1,3,5]triazine as colourless prisms (crystallised from toluene/ethyl acetate mixture), m.p. 188°–191° C.; microanalysis, found: C,53.5; H,5.0; N,36.51; C$_{12}$H$_{13}$N$_7$O requires: C,53.11 H,4.8; N,36.2%; NMR: 0.1–0.5 (complex, 4H, cyclopropyl-CH$_2$), 1.1(complex, 1H, CH), 3.15(t,3H, CH$_2$N), 6.65(q,1H, furyl-4H), 7.05(d, 1H, furyl-3H), 7.4–7.6(complex, 1H, NH), 7.85(d,1H, furyl-5H), 8.0–8.5(broad d,2H, NH$_2$); m/e 272 (M+H)$^+$.

EXAMPLE 68

(R)-7-amino-2-(2-furyl-7-[α-methylbenzylamino][1,2,4]triazolo[1,3,5]triazine as a colourless microcrystalline powder (crystallised from toluene) m.p. range; microanalysis, found: C,62.5; H,5.3; N,28.3%; C$_{16}$H$_{15}$N$_7$O+0.33 C$_7$H$_8$ requires: C,62.5; H,5.1; N,27.9%; NMR: 1.5(d,3H, CH$_3$), 2.3(s,1H equivalent, toluene CH$_3$), 5.0–5.3 (complex, 1H, CH), 6.65(q,1H, furyl-4H), 7.05(d,1H, furyl-3H), 7.1–7.5 (complex, 5H, phenyl-H+toluene), 7.85(d,1H, furyl-5H), 7.9–8.4 (complex, 3H, NH+NH$_2$); m/e 322 (M+H)$^+$.

EXAMPLE 69

7-amino-5-[2-(4-chlorophenyl)ethylamino]-2-(2-furyl)-[1,2,4]triazolo[1,5-a] [1,3,5]triazine as pale yellow prisms (crystallised from ethanol), m.p. 259°–261° C.; microanalysis, found: C,54.3; H,3.8; N,27.5%; C$_{16}$H$_{14}$N$_7$ClO requires: C,54.0; H,3.9; N,27.6%; NMR: 2.85(t,2H, CH$_2$Ar), 3.5(m,2H, CH$_2$N), 6.65(q,1H, furyl-4H), 7.05(q,1H, furyl-3H), 7.2–7.4 (complex, 4H, phenyl-H), 7.4–7.6 (complex, 1H, NH), 7.85(d,1H, furyl-5H), 8.0–8.5(broad d,2H, NH$_2$); m/e 356 (M+H)$^+$.

EXAMPLE 70

7-amino-2-(2-furyl)-5-(exo-2-norbornyl)amino-[1,2,4]triazolo[1,5-a] [1,3,5]triazine as colourless prisms (crystallised from 2-propanol) m.p. 290°–293° C.; microanalysis, found: C,58.5; H,6.9; N,26.6%; C$_{15}$H$_{17}$N$_7$O.C$_3$H$_7$OH requires: C,58.3; H,6.7; N,26.4%; NMR: 1.05(d,6H, (CH$_3$)$_2$), 1.1–1.7 (complex, 8H, norbornyl-CH$_2$), 2.2 (broad s,1H, norbornyl-CH), 3.6–4.4(broad d, 1H, NH), 3.8(m, 1H, CHOH), 6.65(q,1H, furyl-4H), 7.05(d,1H, furyl-3H), 7.2–7.5 (complex, 1H, NH), 7.85(d, 1H, furyl-5H), 7.9–8.4(broad d,2H, NH$_2$); m/e 312 (M+H)$^+$.

EXAMPLE 71

7-amino-2-(2-furyl)-5-[2-(2-methoxyphenyl)ethylamino]-[1,2,4]triazolo[1,5-a] [1,3,5]triazine as colourless prisms (crystallised from ethanol), m.p. 189°–190° C.; microanalysis, found: C,58.3; H,5.0; N,28.3%; C$_{17}$H$_{17}$N$_7$O$_2$ requires: C,58.1; N,4.9; N,27.9%; NMR: 2.8(t,2H, ArCH$_2$), 3.45(t,2H, CH$_2$N), 3.8(s,3H, CH$_3$O), 6.7(q,1H, furyl-4H), 6.8–7.0 (complex, 2H, ArH), 7.05(q,1H, furyl-3H), 7.1–7.3 (complex, 2H, ArH), 7.3–7.5 (broad t,1H, NH), 7.85(d,1H, furyl-5H), 8.0–8.4(broad d,2H, NH$_2$); m/e 352 (M+H)$^+$.

EXAMPLE 72

7-amino-5-(2-fluorobenzyl)amino-2-(2-furyl)[1,2,4-]triazolo[1,5-a] [1,3,5]triazine as pale yellow prisms (crystallised from ethanol), m.p.244°-246° C.; microanalysis, found: C,55.5; H,3.6; N,30.1%; $C_{15}H_{12}FN_7O$ requires: C,55.4; H,3.7; N,30.1%; NMR: 4.5(d,2H, C$\underline{H}_2$). 6.65(q,1H, furyl-4$\underline{H}$), 7.0–7.5 (complex, 5H, Ar$\underline{H}$ +furyl-3$\underline{H}$), 7.85(d, 1$\underline{H}$, furyl-5$\underline{H}$), 7.9(broad t, 1$\underline{H}$, N$\underline{H}$), 8.0–8.4(broad s,1H, N$\underline{H}_2$); m/e 326 (M+H)$^+$.

EXAMPLE 73

7-amino-2-(2-furyl)-5-(3-methoxybenzyl)amino-[1,2,4]-triazolo[1,5-a] [1,3,5]triazine as a pale yellow prisms (crystallised from ethyl acetate), m.p. 194°–196° C.; microanalysis, found: C,57.3; H,4.3; N,29.2%; $C_{16}H_{15}N_7O_2$ requires: C,57.0; H,4.4; N,29.1%; NMR: 3.75(s,3H, C$\underline{H}_3$), 4.5(d,2H, C$\underline{H}_2$), 6.65(q,1H, furyl-4$\underline{H}$), 6.8 (complex, 1H, phenyl-4$\underline{H}$), 6.9 (complex, 2H, phenyl-2$\underline{H}$ and 6$\underline{H}$), 7.05(d, 1H, furyl-3$\underline{H}$), 7.2(t,1H, phenyl-5$\underline{H}$), 7.85(d, 1H, furyl-5$\underline{H}$), 7.85–8.05 (complex, 1$\underline{H}$,N$\underline{H}$), 8.0–8.5(broad d,2$\underline{H}$, N$\underline{H}_2$); m/e 338 (M+H)$^+$.

EXAMPLE 74

7-amino-2-(2-furyl)-5-(3,4-methylenedioxybenzyl)amino-[1,2,4]-triazolo[1,5-a] [1,3,5]triazine, pale yellow prisms (crystallised from ethanol), m.p. 217°–219° C. (decomposed); microanalysis, found: C,55.0; H,3.5; H,28.0; $C_{16}H_{13}N_7O_3$ requires: C,54.7; H,3.7; N,27.9%. NMR: 4.4(d,2H, C$\underline{H}_2$), 5.95(s,2H, OC$\underline{H}_2$O), 6.65(q,1H, furyl-4$\underline{H}$), 6.7–6.9 (complex, 3H, phenyl-$\underline{H}$), 7.05(d, 1H, furyl-3$\underline{H}$), 7.85(d, 1H, furyl-5$\underline{H}$), 7.85–8.05 (complex, 1H, N$\underline{H}$), 8.05–8.5(broad d,2H, N$\underline{H}_2$); m/e 352 (M+H)$^+$.

EXAMPLE 75

7-amino-5-[2-[4-(2-t-butoxycarbonylethyl)phenyl]ethylamino]-2-(2-furyl)-[1,2,4]triazolo-[1,5-a][1,3,5]triazine, as colourless prisms (crystallised from 2-propanol), m.p.: 197°–199° C.; microanalysis, found: C,61.4; H,6.2; N,21.8%; $C_{23}H_{27}N_7O_3$ requires: C,61.5; H,6.1; N,21.8%; NMR: 1.35(s,9H, (C$\underline{H}_3$)$_3$), 2.5(t,2H, C$\underline{H}_2$CO), 2.7–2.9 (complex, 4H, C$\underline{H}_2$-Ar-C$\underline{H}_2$), 3.5(q,2H, C$\underline{H}_2$N), 6.65(q,1H, furyl-4$\underline{H}$), 7.05(q,1H, furyl-3$\underline{H}$), 7.15(q,4H, phenyl-$\underline{H}$), 7.4–7.6 (complex, 1H, N$\underline{H}$), 7.85(d, 1H, furyl-5$\underline{H}$), 8.0–8.4(broad d,2H, N$\underline{H}_2$); m/e 450 (M+H)$^+$.

The required 2-[4-(2-t-butoxycarbonylethyl)phenyl]ethylamine was prepared as described in Journal of Medicinal Chemistry, 1990, 33, 1919–1924.

EXAMPLE 76

7-amino-2-(2-furyl)-5-[2-(4-hydroxyphenylacetamido)ethyl]amino[1,2,4]-triazolo[1,5-a] [1,3,5]triazine as colourless prisms (crystallised from ethanol), m.p. 242°–245° C. (decomposed); microanalysis, found: C,54.7; H,4.9; N,28.8%; $C_{18}H_{18}N_8O_3$ requires: C,54.8; H,4.6; N,28.4%; NMR: 3.1–3.5 (complex, 6H, 3C$\underline{H}_2$), 6.65 (complex, 3H, phenyl-$\underline{H}$+furyl-4$\underline{H}$), 7.05 (complex, 3H, phenyl $\underline{H}$+furyl-3$\underline{H}$), 7.3–7.5(broad t,1H, N$\underline{H}$), 7.85(q,1H, furyl-5$\underline{H}$), 7.95(broad t,1H, N$\underline{H}$), 8.0–8.5(broad d,2H, N$\underline{H}_2$), 9.15(broad s,1H, O$\underline{H}$); m/e 395 (M+H)$^+$.

The starting amine was prepared as follows:

A solution of ethyl 4-hydroxyphenylacetate (18 g) in 1,2-diaminoethane (50 ml) was heated under reflux overnight. The solvent was removed in vacuo and the residue triturated with acetonitrile to yield a solid (12.4 g). This was crystallised from an acetonitrile/ethanol mixture (1:1 v/v) to give 2-aminoethyl-(4-hydroxyphenyl)acetamide as colourless crystals, m.p. 168°–170° C., which was essentially pure by TLC and was used without further characterisation.

EXAMPLE 77

7-amino-2-(2-furyl)-5-(3-phenyl-2-trans-propenyl)amino-[1,2,4]triazolo[1,5-a] [1,3,5]triazine as pale yellow prisms, (crystallised from 2-propanol), m.p. 184°–187° C., resolidified, then m.p. 218°–220° C.; microanalysis, found: C,61.2; 61.11 H,4.2; 4.3; N,29.3, 29.3; $C_{17}H_{15}N_7O$ requires: C,61.2; H,4.5; N,29.4%; NMR: 4.3(broad s,2H, C$\underline{H}_2$), 6.2–6.4(d of t, 1H, C$\underline{H}$CH$_2$), 6.5(d,1H, C$\underline{H}$ Ar), 6.65(q,1H, furyl-4$\underline{H}$), 7.05(d, 1H, furyl-3$\underline{H}$), 7.2–7.5 (complex, 5H, phenyl $\underline{H}$), 7.6–7.8 (complex, 1H, N$\underline{H}$), 7.85(q,1H, furyl-5$\underline{H}$), 8.0–8.6(broad d,2H, N$\underline{H}_2$); m/e 334 (M+H)$^+$.

EXAMPLE 78

7-amino-2-(2-furyl)-5-(2-methoxyethyl)amino-[1,2,4]triazolo-[1,5-a] [1,3,5]triazine as pale yellow prisms (crystallised from ethanol), m.p.: 198°–200° C. microanalysis, found: C,48.4; H,4.9; N,35.2%; $C_{11}H_{13}N_7O_2$ requires: C48.0; H,4.8; N,35.6%; NMR: 3.25(s,3H, C$\underline{H}_3$O), 3.45(s, 4H, C$\underline{H}_2$C$\underline{H}_2$), 6.65(q,1H, furyl-4$\underline{H}$), 7.05(d, 1H, furyl-3$\underline{H}$), 7.3–7.5(broad d,1H, N$\underline{H}$), 7.8(q,1H, furyl-5$\underline{H}$), 8.0–8.4(broad d,2H, N$\underline{H}_2$); m/e 276 (M+H)$^+$.

EXAMPLE 79

7-amino-5-cyclopentylamino-2-(2-furyl)-[1,2,4]-triazolo-[1,5-a][1,3,5]triazine as colourless prisms (crystallised from ethanol), m.p.: 151°–154° C.; microanalysis, found: C, 55.1; H, 5.4; N, 34.1%; $C_{13}H_{15}N_7O$ requires: C, 54.7; H, 5.3; N, 34.4%; NMR: 1.4–2.0 (complex, 8H, cyclopentyl-C$\underline{H}_2$), 4.1–4.3(complex, 1H, C$\underline{H}$N), 6.65(q, 1H, furyl-4$\underline{H}$), 7.05(d, 1H, furyl-3$\underline{H}$), 7.3–7.5(complex, 1H, N$\underline{H}$), 7.85(d, 1H, furyl-5$\underline{H}$), 7.9–8.4(broad d, 2H, N$\underline{H}_2$); m/e 286 (M+H)$^+$.

EXAMPLE 80

7-amino-5-[2-(4-t-butoxycarbonylmethoxy)phenylethyl]amino-2-(2-furyl-[1,2,4]-triazolo[1,5-a][1,3,5]triazine as colourless fluffy crystals (crystallised from ethanol), m.p.: 199°–200° C.; microanalysis, found: C, 58.4; H, 5.5; N, 21.7%; $C_{22}H_{25}N_7O_4$ requires C, 58.5; H, 5.6; N, 21.7%; NMR: 1.4(s, 9H, t-butyl-$\underline{H}$), 2.8(t, 2H, ArC$\underline{H}_2$), 3.45(complex, 2H, C$\underline{H}_2$N), 4.6(s, 2H, C$\underline{H}_2$O) 6.65(q, 1H, furyl-4$\underline{H}$), 6.8(d, 2H, phenyl-$\underline{H}$), 7.05(d, 1H, furyl-3$\underline{H}$), 7.15(d, 2H, phenyl-$\underline{H}$), 7.3–7.5(complex, 1H, N$\underline{H}$), 7.85(d, 1H, furyl-5$\underline{H}$), 8.0–8.4(broad d, 2H, N$\underline{H}_2$); m/e 452 (M+H)$^+$.

The required 2-[4-(2-t-butoxycarbonylmethoxy)-phenyl]ethylamine may be prepared as described in Journal of Medicinal Chemistry, 1990, 33, 1919–1924.

EXAMPLE 81

4-(2-Aminoethyl)phenol (2.74 g) was added to a stirred suspension of 7-amino-2-(2-furyl)-5-methylsulphonyl-[1,2,4]triazolo[1,5-a][1,3,5]triazine (1.4 g) in acetonitrile (150 ml) and stirring was continued overnight. The solvent was evaporated and the residue was purified by chromatography on silica (100 g) eluting with dichloromethane containing methanol (50% v/v). The solid (1.23 g) obtained was crystallised from ethyl acetate to give 7-amino-2-(2-furyl)-5-[2-(4-hydroxyphenyl)ethyl]amino-[1,2,4]triazolo[1,5-a][1,3,5]triazine, m.p. 225°–227° C.; microanalysis, found: C, 56.7; H, 4.6; N, 29.4%; $C_{16}H_{15}N_7O_2$ requires C, 57.0; H, 4.5; N, 29.1%, NMR: 2.73(t, 2H, C$\underline{H}_2$Ar), 3.41(t, 2H, NHC$\underline{H}_2$), 6.66(complex, 3H, 2phenyl-$\underline{H}$ and furyl-4$\underline{H}$), 7.02(complex, 3H, 2phenyl-$\underline{H}$ and furyl-3$\underline{H}$), 7.40(br t, 1H,

EXAMPLE 82

7-Amino-2-(2-furyl)-5-[2-(4-hydroxyphenyl)ethyl]amino[1,2,4]-triazolo[1,5-a][1,3,5]triazine (1 g, prepared as described in Example 81) was suspended in dichloromethane (20 ml) and trifluoroacetic acid (20 ml) was added with stirring. Pivaloyl chloride (0.4 ml) was added dropwise at ambient temperature. The mixture was stirred for 2 hours and then the dichloromethane and trifluoroacetic acid was removed in vacuo. The residue was purified by chromatography on silica (100 g) eluting with dichloromethane containing methanol (5.0% v/v). The solid obtained (1.2 g) was crystallised from toluene and finally from isopropanol (25 ml) to give 7-amino-2-(2-furyl)-5-[2-(4-pivaloyloxyphenyl)ethyl]amino[1,2,4]-triazolo[1,5-a][1,3,5]triazine as a solid; m.p. 208°–210° C.; microanalysis, found: C, 59.6; H, 6.1; N, 21.7%; $C_{21}H_{24}N_7O_3$ 0.5 $C_3H_7OH$ requires C, 59.9; H, 6.0; N, 21.7%; NMR 1.06(d, ca 3H, $(CH_3)_2CHOH$), 1.3(s, 9H, $CH_3C$), 2.9(t, 2H, $CH_2$ Ar), 3.55 (t, 2H, $CH_2N$), 3.80(heptet, ca 0.5 H, $(CH_3)_2CHOH$), 6.68(dd, 1H, furyl-4H), 7.01 and 7.30 ($A_2B_2$ pattern, 4H, phenyl-H), 7.08 (d, 1H, furyl-3H) and 7.82(d, 1H, furyl-5H); m/e 422 (M+H)+.

EXAMPLES 83–109

Using a procedure similar to that described in Example 1, but using the appropriate alcohol instead of phenol, the following compounds of formula I were obtained:

EXAMPLE 83

7-amino-2-(2-furyl)-5-(3-methylphenoxy)[1,2,4]-triazolo[1,5-a][1,3,5]triazine as a white solid from isopropanol, m.p. 221°–223° C.; microanalysis, found: C, 58 5; H, 3.9; N, 27.4%; $C_{15}H_{12}N_6O_2$ requires: C, 58.4; H, 3.9; N, 27.3%; NMR 2.35(s, 3H, ArCH_3), 6.68(dd, 1H, furyl-4H), 7.0–7.4(complex, 5H, 4phenyl-H and furyl-3H), 7.89(s, 1H, furyl-5H) and 8.94(d, 2H, NH_2); m/e 309 (M+H)+.

EXAMPLE 84

7-amino-2-(2-furyl)-5-(2-methylpropyloxy)[1,2,4]-triazolo[1,5-a][1,3,5]triazine as a white solid from toluene, m.p. 184°–185° C. microanalysis, found: C, 52.9; H, 5.2; N, 30.3; $C_{12}H_{14}N_6O_2$ requires: C, 52.5; H, 5.1; N, 30.6%; NMR 0.99(d, 6H, CH_3), 2.05(m, 1H, CH(CH_3)_2), 4.10(d, 2H, OCH_2), 6.68(dd, 1H, furyl-4H), 7.11(d, 1H, furyl-3H), 7.89(d, 1H, furyl-5H) and 8.75(brs, 2H, NH_2); m/e 275 (M+H)+.

EXAMPLE 85

7-amino-2-(2-furyl)-5-(3-pyridyloxy)-[1,2,4]triazolo[1,5-a][1,3,5]triazine as colourless crystals (crystallised from ethanol), m.p. 287°–290° C. (decomposed); microanalysis, found C, 53.2; H, 3.0; N 33.0%; $C_{13}H_9N_7O_2$ requires: C, 52.8; H, 3.1; N, 33.2%; NMR 6.70 (dd, 1H, furyl-4H), 7.22 (d, 1H, furyl-3H), 7.52(dd, 1H, pyridyl-5H), 7.75 (d, 1H, pyridyl-4H), 7.92(s, 1H, furyl-5H), 8.52 (complex, 2H, pyridyl-2H and pyridyl-6H) and 9.03 (br s, 2H, NH_2); m/e 296 (M+H)+.

EXAMPLE 86

7-amino-2-(2-furyl)-5-(3-[1,2,5-thiadiazolyloxy][1,2,4]triazolo[1,5-a][1,3,5]triazine as a white solid from ethanol, m.p. 273°–5° C.; microanalysis, found: C, 39.8; H, 1.9; N, 36.9%; $C_{10}H_6N_8O_2S$ requires: C, 39.7; H, 2.0; N, 37.1%; NMR 6.70 (dd, 1H, furyl-4H), 7.16 (d, 1H, furyl-3H), 7.91 (d, 1H, furyl-5H), 8.85 (s, 1H, thiadiazolyl-4H) and 9.21 (br s, 2H, NH_2); m/e 303 (M+H)+.

The starting material may be prepared as described in Journal of Organic Chemistry, 32, 2828 (1967).

EXAMPLE 87

7-amino-2-(2-furyl)-5-(3-trifluoromethylphenoxy)[1,2,4]triazolo[1,5-a][1,3,5]triazine as a crystalline solid from isopropanol, m.p. 236°–238° C.; microanalysis, found C, 49.6; H, 2.3; N, 22.9%; $C_{15}H_9F_3N_6O_2$ requires: C, 49.7; H, 2.5; N, 23.2%; NMR 6.70 (dd, H, furyl-4H), 7.13 (d, 1H, furyl-3H), 7.55–7.75 (complex, 4H, phenyl-H), 7.91 (s, 1H, furyl-5H) and 9.03 (br s, 2H, NH_2); m/e 362 M+.

EXAMPLE 88

7-amino-5-(3-chlorophenoxy)-2-(2-furyl)-[1,2,4]triazolo[1,5-a][1,3,5]triazine as colourless needles from ethyl acetate, m.p. 224°–226° C.; microanalysis, found C, 50.9; H, 2.6; N, 25.6%; $C_{14}H_9ClN_6O_2$ requires: C, 51.1; H, 2.7; N, 25.6%; NMR 6.57 (dd, 1H, furyl-4H), 7.1–7.4 (complex, 5H, phenyl-H and furyl-3H), 7.70 (s, 1H, furyl-5H) and 8.25 (d, 2H, NH_2); m/e 328 M+.

EXAMPLE 89

7-amino-5-(2-ethylsulphinylethoxy)-2-(2-furyl)-[1,2,4]triazolo 1,5-a][1,3,5]triazine as a white solid from ethanol, m.p. 253°–5° C.; microanalysis; found C, 45.0; H, 4.3; N, 26.4%; $C_{12}H_{14}N_6O_3S$ requires: C, 44.7: H, 4.3: N, 26.1%; NMR 1.22 (t, 3H, CH_3), 2.7–3.3 (m, 4H, CH_2S(O)CH_2), 4.66 (m, 2H, OCH_2), 6.70 (dd, 1H, furyl-4H), 7.14 (d, 1H, furyl-3H), 7.90 (s, 1H, furyl-5H) and 8.84 (br d, 2H, NH_2); m/e 323 (M+H)+.

The starting alcohol was prepared as follows:

To a solution of 2-ethylthioethanol (10.6 g) in a methanol/water mixture (2:1 v/v) was added sodium metaperiodate [21.4 g), and the mixture was heated under reflux for 2 hours. The suspension was then cooled and filtered, and the filtrate evaporated in vacuo. The residue was distilled to give 2-ethylsulphinyl ethanol as a colourless oil, b.p. 125°–126° C. (0.5 mm Hg), NMR: 1.35 (t, 3H, CH_3), 2.7–3.0 (m, 4H, CH_2S(O)CH_2), 4.05 (m,2H, CH_2O), 4.45 (s, 1H, OH); m/e 123(M+H)+.

EXAMPLE 90

7-amino-5-(2-chlorophenoxy)-2-(2-furyl)-[1,2,4]triazolo[1,5-a][1,3,5]triazine as a white solid from ethanol, m p 271°–273° C.; microanalysis, found: C, 51.2, H, 2.7; N, 25.4%; $C_{14}H_9ClN_6O_2$ requires: C, 51.1 : H, 2.7; N, 25.6%; NMR 6.68 (dd, 1H, furyl-4H), 7.11 (d, 1H, furyl-3H), 7.3–7.7 (complex, 4H, phenyl-H), 7.89 (s, 1H, furyl-5H) and 9.05 (br s, 2H, NH_2); m/e 329 (M+H)+.

EXAMPLE 91

7-amino-2-(2-furyl)-5-(2,3,4,5,6-pentafluorophenoxy)-[1,2,4]triazolo[1,5-a][1,3,5]triazine as white crystals from ethanol, m.p. 312–314 (decomposed); microanalysis, found: C, 43.9;, H, 1.4; N, 21.9%; $C_{14}H_5F_5N_6O_2$ requires: C, 43.7; H, 1.3: N, 21.97.; NMR 6.70(dd, H, furyl-4H), 7.14 (d, 1H, furyl-3H), 7.92 (s, 1H, furyl-5H) and 9.27 (br s, 2H, NH_2); m/e 385 (M+H)+.

EXAMPLE 92

7-amino-5-(3-cyanophenoxy)-2-(2-furyl)-[1,2,4]triazolo[1,5-a][1,3,5]triazine as a white solid from ethanol, m.p.>300° C.; microanalysis, found: C, 56.6; H, 2.9; N, 30.6%; $C_{15}H_9N_7O_2$ requires: C, 56.4; H, 2.8; N, 30.7%; NMR 6.70 (dd, 1H, furyl-4$\underline{H}$), 7.13 (d, 1H, furyl-3$\underline{H}$), 7.4–7.85 (complex, 4H, phenyl-$\underline{H}$), 7.91 (s, 1H, furyl-5$\underline{H}$) and 9.06 (d, 2H, N$\underline{H}_2$); m/e 320 (M+H)+.

EXAMPLE 93

7-amino-5-(4-$\underline{N}$-dimethylaminosulphonylphenoxy)-2-(2-furyl)-[1,2,4]triazolo[1,5-a][1,3,5]triazine as colourless crystals, m.p. 272°–274° C. (decomposed); microanalysis, found: C, 47.6; H, 3.8; N, 23.3; H$_2$O 1.3%; $C_{16}H_{15}N_7O_4S$ 0.33 $C_2H_5OH$, 0.33H$_2$O requires: C, 47.4; H, 4.1; N, 23.2; H$_2$O, 1.4%; NMR 2.67 (s, 6H, N(C$\underline{H}_3$)$_2$), 6.70 (dd, 1H, furyl-4$\underline{H}$), 7.13 (d, 1H, furyl-3$\underline{H}$), centre 7.5 (A$_2$B$_2$ pattern, 4H, phenyl-$\underline{H}$), 7.91 (s, 1H, furyl-5$\underline{H}$) and 9.04 (d, 2H, N$\underline{H}_2$); m/e 402 (M+H)+.

The phenol starting material was prepared as follows:

Sodium 4-hydroxybenzenesulphonate (20 g) was heated under reflux in thionyl chloride (200 ml) for 2½ hours. The solvent was then removed in Vacuo, and the residue was azeotroped with toluene and then treated with a solution of dimethylamine in industrial methylated spirits (200 ml). Purification by chromatography on silica (eluting with dichloromethane/methane (99:1 v/v) gave N,N-dimethyl-4-hydroxybenzenesulphonamide as colourless needles (crystallised from water), m.p. 82°–84° C.; NMR: 2.55 (s, 6H, 2C$\underline{H}_3$), 6.95 (d, 2H, phenyl-$\underline{H}$), 7.55 (d, 2H, phenyl-$\underline{H}$), 10.5 (s, 1H, O$\underline{H}$); m/e 202 (M+H).

EXAMPLE 94

7-amino-2-(2-furyl)-5-(2-nitrophenoxy)-[1,2,4]triazolo[1,5-a][1,3,5]triazine as a pale yellow solid, m.p. 303°–305° C. (decomposed); microanalysis, found: C, 49.7, H, 2.6; N, 28.5%; $C_{14}H_9N_7O_4$ requires: C, 49.6, H, 2.6; N, 28.9%; NMR 6.70 (dd, 1H, furyl-4$\underline{H}$), 7.21 (d, 1H, furyl-3$\underline{H}$), 7.59 (complex, 2H, phenyl-5$\underline{H}$ and 6$\underline{H}$), 7.85 (dd, 1H, phenyl-4$\underline{H}$), 7.91 (s, 1H, furyl-5$\underline{H}$), 8.20 (dd, 1H, phenyl-3$\underline{H}$) and 9.15 (d, 2H, N$\underline{H}_2$); m/e 340 (M+H)+.

EXAMPLE 95

7-amino-5-(2-methoxycarbonylphenoxy)-2-(2-furyl)[1,2,4]triazolo[1,5-a][1,3,5]triazine as a solid from methanol, m.p. 287°–288° C.; microanalysis, found; C, 54.4; H, 3.2; N, 23.67.; $C_{16}H_{12}N_6O_4$ requires: C, 54.5; H, 3.4; N, 23.9%; NMR 3.67 (s, 3H, CO$_2$CH$_3$), 6.69 (dd, 1H, furyl-4$\underline{H}$), 7.12 (d, 1H, furyl-3$\underline{H}$), 7.3–7.8 (complex, 3H, phenyl-$\underline{H}$), 7.90 (s, 1H, furyl-5$\underline{H}$) and 9.00 (d, 2H, N$\underline{H}_2$).

EXAMPLE 96

7-amino-5-(4-methoxycarbonylphenoxy)-2-(2-furyl)-[1,2,4]triazolo[1,5-a][1,3,5]triazine as a white solid from ethanol, m.p. 293°–5° C. (decomposition); microanalysis, found: C, 54.6; H, 3.6; N, 23.5%; $C_{16}H_{12}N_6O_4$ requires: C, 54.5; H, 3.4; N, 23.9%; NMR 3.88 (s, 3H, CO$_2$CH$_3$), 6.70 (dd, 1H, furyl-4$\underline{H}$), 7.13 (d, 1H, furyl-3$\underline{H}$), 7.41 and 8.05 (A$_2$B$_2$ pattern, 4H, phenyl-$\underline{H}$), 7.90 (s, 1H, furyl-5$\underline{H}$) and 9.04 (d, 2H, N$\underline{H}_2$); m/e 353 (M+H)+.

EXAMPLE 97

7-amino-5-(3-methoxycarbonylphenoxy)-2-(2-furyl)-[1,2,4]triazolo[1,5-a][1,3,5]triazine as a white solid from ethanol, m.p. 226°–228° C.; microanalysis, found: C, 52.7; H, 3.6; N, 22.5; H$_2$O, 3.7%; $C_{16}H_{12}N_6O_4$ 0.1 $C_2H_5OH$ (0.75H$_2$O) requires: C, 52.5; H, 3.8, N, 22.7; H$_2$O, 3.6%; NMR 3.86 (s, 3H, CO$_2$CH$_3$), 6.68 (dd, 1H, furyl-4$\underline{H}$), 7.12 (d, 1H, furyl-3$\underline{H}$), 7.5–7.9 (complex, 5H, 4 phenyl-$\underline{H}$ and furyl-5$\underline{H}$) and 9.00 (d, 2H, N$\underline{H}_2$); m/e 353 (M+$\overline{H}$)+.

EXAMPLE 98

7-amino-5-(4-methoxycarbonylmethylphenoxy)-2-(2-furyl)-[1,2,4]triazolo[1,5-a][1,3,5]triazine as a white solid from ethanol, m.p. 234°–236° C.; microanalysis, found: C, 55.7; H, 4.0; N, 22.7%; $C_{17}H_{14}N_6O_4$ requires: C, 55.7; H, 3.8, N, 23.0%; NMR 3.65 (s, 3H, CO$_2$CH$_3$), 3.71 (s, 2H, CH$_2$COCH$_3$), 6.68(dd, 1H, furyl-4$\underline{H}$), 7.10 (d, 1H, furyl-3$\underline{H}$), 7.13 and 7.33 (A$_2$B$_2$ pattern, 4H, phenyl-$\underline{H}$), 7.88 (d, 1H, furyl-5$\underline{H}$) and 8.96 (d, 2H, N$\underline{H}_2$); m/e 367 (M+H)+.

The phenol starting material was prepared as follows:

A solution of 4-hydroxyphenoxyacetic acid (33.6 g) in methanol was treated with hydrogen chloride gas and left to stand at ambient temperature overnight. The solvent was removed in vacuo and the residue taken up in ethyl acetate. This solution was washed sequentially with saturated sodium hydrogen carbonate solution (2×100 ml) and brine (100 ml), then dried (MgSO$_4$) and the solvent evaporated to give methyl 4-hydroxyphenoxyacetate as a colourless crystalline mass, m.p. 112°–114° C.; NMR: 3.8 (s, 3H, CH$_3$), 4.55 (s, 2H, CH$_2$), 6.75 (s, 4H, phenyl-$\underline{H}$) 6.8–7.8 (broad s, 1H, O$\underline{H}$); m/e 200 (M+NH$_4$)+.

EXAMPLE 99

7-amino-5-(4-methoxycarbonylmethoxyphenoxy)-2-(2-furyl)-[1,2,4]triazolo[1,5-a][1,3,5]triazine as a white solid from ethanol, m.p. 265°–267° C.; microanalysis, found: C, 53.8; H, 3.7; N, 21.6% $C_{17}H_{14}N_6O_5$ requires: C, 53.4; H, 3.7; N, 22.0%; NMR 3.72 (s, 3H, CO$_2$CH$_3$), 4.81 (s, 2H, OCH$_2$), 6.69 and 7.15 (A$_2$B$_2$ pattern, 4H, phenyl-$\underline{H}$), 7.10 (d, 1H, furyl-3$\underline{H}$), 7.89 (s,1H, furyl-5$\underline{H}$) and 8.94 (d, H, N$\underline{H}_2$); m/e 383 (M+H)+.

EXAMPLE 100

7-amino-2-(2-furyl)-5-(4-[(1-propyl)aminocarbonylmethoxy]phenoxy)-[1,2,4]triazolo[1,5-a][1,3,5]triazine as a solid from ethanol, m.p. 203°–205° C.; microanalysis, found: C, 55.8; H, 4.8; N, 23.8%; $C_{19}H_{19}N_7O_4$ requires: C, 55.7; H, 4.7; N, 24.0%; NMR 0.85 (t, 3H, CH$_2$CH$_3$), 1.47 (m, 2H, CH$_2$CH$_3$), 3.11 (q, 2H, C$\underline{H}_2$N), 4.47 (s,2H, OCH$_2$), 6.67 (dd, 1H, furyl-4$\underline{H}$), 6.98 and 7.14 (A$_2$B$_2$ pattern, 4H, phenyl-$\underline{H}$), 7.10 (d, 1H, furyl-3$\underline{H}$), 7.87 (s, 1H, furyl-5$\underline{H}$), 8.03 (t, 1H, N$\underline{H}$) and 8.82 (d, 2$\overline{H}$, N$\underline{H}_2$); m/e 410 (M+H)+.

The requisite phenol starting material was prepared as follows:

A solution of 1-propylamine (4.1 ml) and methyl 4-hydroxyphenoxyacetate (3.64 g) in methanol (50 ml) was left to stand for 72 hours at ambient temperature. The solvent was evaporated in vacuo and the residue taken up in ethyl acetate. The solution was washed sequentially with 1M HCl (2×25 ml) and brine (30 ml), then dried (MgSO$_4$) and the solvent evaporated to give N-(1-propyl)-4-hydroxyphenoxyacetamide as a red oil, NMR: 0.95 (t, 3H, CH$_3$), 1.55 (m, 2H, CH$_2$) 3.3 (q 2H, $CH_2N$), 4.4 (s, 2H, $CH_2O$) 6.5–6.7 (broad s, 1H, $O\underline{H}$), 6.8 (s, 4H, phenyl-$\underline{H}$); m/e 227 $(M+NH_4)^+$, 210 $(M+H)^+$.

EXAMPLE 101

7-amino-5-[4-([N-dimethylaminoethyl-N-methyl-]aminocarbonylmethoxy)phen -oxy]-2-(2-furyl)-[1,2,4]triazolo[1,5-a][1,3,5]triazine as a solid from ethanol, m.p 192°–4° C.; microanalysis, found: C, 55.9, H, 5.7; N, 24.8%; $C_{21}H_{24}N_8O_4$ requires: C, 55.7; H, 5.3: N, 24.8%; NMR 2.2 (d, 6H, $N(CH_3)_2$), 2.47 (m, 2H, $CH_2N(CH_3)_2$), 2.86 and 3.02 (s, 3H, $NCH_3$ rotamers), 3.41 (m, 2H, $CONCH_2$), 4.83 (d, 2H, $OC\underline{H}_2$), 6.68 (dd, 1H, furyl-4$\underline{H}$), 6.95 and 7.13 ($A_2B_2$ pattern, 4H, phenyl-$\underline{H}$), 7.12 (s, 1H, furyl-3$\underline{H}$), 7.88 (m, 1H, furyl-5$\underline{H}$) and 8.95 (d, 2H, $NH_2$); m/e 453 $(M+H)^+$.

The requisite phenol starting material was prepared as follows:

A solution of methyl 4-hydroxyphenoxyacetate (3.64 g) and N,N,N'-trimethylethylenediamine (5.1 g) in methanol (50 ml) was heated under reflux for 24 hours. The solvent was then evaporated in vacuo and the residue purified by chromatography on silica (eluting with dichloromethane/methanol 9:1 v/v) to give N-(4-hydroxyphenoxyacetyl)-N,N'N'-trimethylethylenediamine as a pale brown oil, NMR: 2.3 (s, 6H, $2CH_3$), 2.5 (t, 2H, $CH_2NMe_2$), 3.0 (d, 3H, $CH_3$), 3.5 (m, 2H, $CH_2$), 4.5–4.7 (d, 2H, $CH_2O$), 6.6–6.8 (m, 4H, phenyl-$\underline{H}$); m/e 253 $(M+H)^+$.

EXAMPLE 102

A solution of 7-amino-2-(2-furyl)-5-phenoxy-[1,2,4]triazolo[1,5-a][1,3,5]triazine (950 mg) in acetic anhydride was heated under reflux for 1.5 hours. The solvent was then evaporated in vacuo and the residue was purified by chromatography on silica eluting with dichloromethane containing ethyl acetate (5% v/v). The amorphous solid thereby obtained was crystallised from toluene to give 7-acetylamino-2-(2-furyl)-5-phenoxy-[1,2,4]-triazolo[1,5-a][1,3,5]triazine as colourless prisms, m.p. 168°–170° C.; microanalysis, found; C, 60.9; H, 4.2; N, 22.6%; $C_{16}H_{12}N_6O_3$ 0.45 $C_7H_8$ requires: C, 60.9; H, 4.1; N, 22.3%; NMR 2.3 (s, 3H equivalent, toluene $CH_3$), 2.35 (s, 3H, $CH_3CO$), 6.7 (q, 1H, furyl-4$\underline{H}$), 7.1–7.6 (complex, 6H, furyl-3H + phenyl-H + toluene), 7.95(d, 1H, furyl-5H), 11.5 (broad s, 1H, N$\underline{H}$); m/e 336 $(M+)$.

EXAMPLES 103–109

Using a procedure similar to that described in Example 1, but using the appropriate alcohol instead of phenol, the following compounds of formula I were obtained:

EXAMPLE 103

7-amino-5-(4-N-cyclohexylaminocarbonylmethyl]-phenoxy)-2-(2-furyl)-[1,2,4]triazolo[1,5-a][1,3,5]triazine as a white solid from ethanol, m.p. 294°–297° C.; microanalysis, found: C,60.5; H,5.4; N,22.4; $H_2O$, 0.8%; $C_{22}H_{23}N_7O_3(0.2)H_2O$ requires C,60.5; H,5.4; N,22.4; $H_2O$, 0.8%; NMR: 1.0–1.8 (complex, 10H, —$CH_2$—), 3.40 (s,2H, $CH_2CO$), 3.52(m, 1H, C$\underline{HN}$), 6.69(dd,1H, furyl-4$\underline{H}$), 7.11(d,1H, furyl-3$\underline{H}$), 7.15 and 7.30($A_2B_2$ pattern, 4H, phenyl-$\underline{H}$), 7.90(m, 1H, furyl-5$\underline{H}$), 7.95(d, 1H, N$\underline{H}$) and 8.97(d,2H, $NH_2$); m/e 434 $(M+H)^+$.

The phenol starting material was prepared by a procedure essentially similar to that described in Example 102, using cyclohexylamine instead of 1-propylamine giving N-cyclohexyl-4-hydroxyphenylacetamide as a colourless crystalline solid, m.p. 87°–89° C., NMR: 1.0–1.5 (complex 5H, cyclohexyl-$CH_2$), 1.5–1.8 (complex, 5H, cyclohexyl-$CH_2$), 3.25(s,2$\underline{H}$, $ArCH_2$), 3.5(m, 1H, C$\underline{HN}$), 6.65(d,2H, phenyl-$\underline{H}$), 7.0(d,2H, phenyl-$\underline{H}$), 7.75(t, 1H, N$\underline{H}$), 9.15(s,1H, —O$\underline{H}$); m/e 234 $(M+H)^+$.

EXAMPLE 104

7-amino-5-[4-([N-dimethylaminoethyl-N-methylaminocarbonylmethyl)phenoxy]-2-(2-furyl-[1,2,4]triazolo[1,5-a][1,3,5]triazine as a hydrochloride salt from isopropanol. The chromatographed free base prepared by a procedure similar to that described in Example 1, was dissolved in methanol and treated with ethereal hydrogen chloride, the solvent evaporated and the residue crystallised from isopropanol); microanalysis, found: C,52.4; H,5.9; N,22.0; Cl,6.9; $H_2O$, 1.6%; $C_{21}H_{24}N_8O_3$ HCl 0.3 $C_3H_7OH$ 0.5$H_2O$ requires: C,52.6; H,5.6; N,22.4; Cl,7.1; $H_2O$ 1.8%; NMR 2.77(S,6H, $N(CH_3)_2$), 3.3(s,3H, N-$CH_3$) 3.23(t,2H, $CH_2N^+$), 3.75 (complex, 4H, $CH_2N$ and $CH_2CO$), 6.69(dd,1H, furyl-4$\underline{H}$), 7.12(d,1H, furyl-3$\underline{H}$), 7.15 and 7.31 ($A_2B_2$ pattern, 4$\underline{H}$, phenyl-$\underline{H}$), 7.90(m, 1H, furyl-5$\underline{H}$), 9.00(d,2H, $NH_2$) and 10.5(br s, 1H, $N^+\underline{H}$) m/e 437$(M+H)^+$.

The phenol starting material was prepared by a procedure essentially similar to that described in Example 102, using N,N,N'-trimethylethylenediamine instead of 1-propylamine, to give the product as a pale yellow oil, essentially pure by TLC, which was used directly.

EXAMPLE 105

7-amino-2-(2-furyl-5-(4-[methoxycarbonylethyl]-phenoxy-[1,2,4]triazolo[1,5-a][1,3,5]triazine as white crystals from ethanol, m.p. 245°–247° C.; microanalysis, found: C,56.9; H,4.4; N,22.37.; $C_{18}H_{16}N_6O_4$ requires: C,56.8; H,4.2; N,22.1%; NMR: 2.67(t,2H, $CH_2$ phenyl), 2.90(t,2H $CH_2CO$), 3.61(s,3H, $CO_2CH_3$), 6.70(dd, 1H, furyl-4$\underline{H}$), 7.11(d,1H, furyl-3$\underline{H}$), 7.15 and 7.29 ($A_2B_2$ pattern, 4H, phenyl-$\underline{H}$), 7.90(d, 1H, furyl-5$\underline{H}$) and 8.95(d,2H, $NH_2$) m/e 381 $(M+H)^+$.

EXAMPLE 106

7-amino-5[4-(3-[N-cyclopentylcarbamoyl]ethyl)-phenoxy]-2-(2-furyl)-1,2,4-triazolo[1,5-a][1,3,5]triazine as a solid from ethanol m.p. 257°–259° C.; microanalysis, found: C,60.8; H,5.3; N,22.3%. $C_{22}H_{23}N_7O_3$ requires: C,61.0; H,5.3; N,22.6%; NMR: 1.2–1.9 (complex, 8H, —$CH_2$—) 2.37(t,2H, $CH_2CO$), 2.84(t,2H, $CH_2$ phenyl), 3.99(m, 1H, C$\underline{HN}$), 6.69(dd,1H, furyl-4$\underline{H}$), 7.10(d,1H, furyl-3$\underline{H}$), 7.15 and 7.28 ($A_2B_2$ pattern, 4$\underline{H}$, phenyl-$\underline{H}$), 7.74(d,1H, N$\underline{H}$), 7.89(d, 1H, furyl-5$\underline{H}$) and 8.95(d,2$\underline{H}$, $NH_2$); m/e 434 $(M+H)^+$.

The requisite phenol starting material was prepared as follows:

A mixture of 3-(4-hydroxyphenyl)propionate (3.6 g) and cyclopentylamine (15 ml) was refluxed for 18 hours. The reaction mixture was then taken up in ethyl acetate (150 ml) and the solution washed sequentially with 2M HCl (4×75 ml), water (50 ml) and brine (50 ml), then dried ($MgSO_4$) and evaporated to give N-cyclopentyl-3-(4-hydroxyphenyl)propionate as a brown oil, NMR: 1.2–1.9 (complex, 8H, cyclopentyl-$\underline{H}$), 2.25(t,2H, $CH_2$), 2.7(t,2H, $CH_2$), 4.0(m, 1H cyclopentyl-$\underline{H}$), 6.65(d,2$\underline{H}$, phenyl-$\underline{H}$), 7.0(d,2H, phenyl-$\underline{H}$), 7.65(d, 1H, N$\underline{H}$), 9.1 (s,1H, O$\underline{H}$); m/e 251 $(M+NH_4)^+$, 234 $(M+H)^+$.

EXAMPLE 107

7-amino-2-(2-furyl)-5-(2-methylphenoxy)-[1,2,4]triazole[1,5-a][1,3,5]triazine as a powder from isopropanol, m.p. 239°–241° C.; microanalysis, found: C,58.3; H,4.9; N,24.5%; $C_{15}H_{12}N_6O_2(0.5)C_3H_7OH$ requires: C,58.5; H,4.7; N,24.8%; NMR: 2.16(s,3H, phenyl C$\underline{H}_3$), 6.69(dd, 1H, furyl-4$\underline{H}$), 7.1–7.4 (complex, 5H, phenyl-$\underline{H}$ and furyl-3$\underline{H}$); 7.89(s,1H, furyl-5$\underline{H}$) and 8.96(d,2$\overline{H}$, N$\underline{H}_2$); m/e 309 (M+H)+.

EXAMPLE 108

7-amino-2-(2-furyl)-5-(4-methylphenoxy)-[1,2,4-]triazolo[1,5-a][1,3,5]triazine as fluffy crystals from isopropanol, m.p. 248°–250° C.; microanalysis, found: C,58.3; H,5.5; N,23.5%; $C_{15}H_{12}N_6O_2(0.8)C_3H_7OH$ requires: C,58.6; H,5.2; N,23.6%; NMR: 2.32(s,3H, phenyl C$\underline{H}_3$), 6.68(dd, 1H, furyl-4$\underline{H}$), 7.11(d,1H, furyl-3$\underline{H}$), 7.0 and 7.24 ($A_2B_2$ pattern, 4$\overline{H}$, phenyl-$\underline{H}$), 7.90(s,1$\overline{H}$, furyl-5$\underline{H}$) and 8.91(s,2H, N$\underline{H}_2$) m/e 309($\overline{M}$+H)+.

EXAMPLE 109

A stirred suspension of 7-amino-2-(2-furyl)-5-methylsulphonyl-[1,2,4]triazolo[1,5-a][1,3,5]triazine (1.4 g) in 1,2-dimethoxyethane (25 ml) was treated with an aqueous solution of 1M sodium hydroxide (25 ml). After 3 hours at room temperature the reaction mixture was acidified with 1M hydrochloric acid (pH 2–3) and stirred for 2 hours. The precipitated yellow solid was collected by filtration and washed with water. Crystallisation from boiling distilled water gave 7-amino-2-(2-furyl)-5-hydroxy-1,2,4-triazolo[1,5-a][1,3,5]triazine (0.47 g) as a pale yellow solid m.p. >300° C.; microanalysis, found: C,44.3; H,2.5; N,38.7%, $C_8H_6N_6O_2$ requires: C,44.0; H,2.8; N,38.5%; NMR: 6.69(dd,1H, furyl-4$\underline{H}$), 7.10(d,1H, furyl-3$\underline{H}$), 7.90(d,1H, furyl-5$\underline{H}$), 8.36(br s, 2H, N$\underline{H}_2$) and 12.1(br s, 1H,O$\underline{H}$); m/e 219 (M+H)+.

EXAMPLES 110–112

Using a procedure similar to that described in Example 2, the following compounds of formula I were obtained starting with the appropriate thiol:

EXAMPLE 110

7-amino-5-([cyclohexylaminocarbonyl]methylthio)-2-(2-furyl)-[1,2,4]triazolo[1,5-a][1,3,5]triazine as a white solid from isopropanol, m.p. 249°–252° C.; microanalysis, found: C, 51.3; H,5.3; N,26.1%; $C_{16}H_{19}N_7O_2S$ requires: C,51.5; H,5.1; N,26.3%; NMR: 1.0–1.8 (complex, 10H, —C$\underline{H}_2$—) 3.51(m, 1H, NC$\underline{H}$), 3.85(s,2H, C$\underline{H}_2$S), 6.69(dd, 1$\overline{H}$, furyl-4$\underline{H}$), 7.14(d,1$\overline{H}$, furyl-3$\underline{H}$), 7.89(m, 1H, furyl-5$\underline{H}$), 7.95(d, 1H, N$\underline{H}$) and 8.88(d,2H, N$\underline{H}_2$); m/e 374 (M+H)+.

The thiol starting material was prepared as follows:

A solution of ethyl 2-mercaptoacetate (12 g) and cyclohexylamine (29.7 g) in ethanol (50 ml) was allowed to stand at ambient temperature for 72 hours, and was then refluxed for 6 hours. The solvent was evaporated and the residue dissolved in ethyl acetate (200 ml). The solution was washed sequentially with 2H HCl (3×50 ml), water (2×50 ml) and brine (50 ml), and the solvent removed in vacuo. The crude product was purified by chromatography on silica (eluting with dichloromethane/methanol 99:1 v/v) to give $\underline{N}$-cyclohexyl-2-mercaptoacetamide as low-melting tan crystals, NMR: 1.0–2.0 (complex, 11H, cyclohexyl-C$\underline{H}_2$ and S$\underline{H}$), 3.2(d,2H, C$\underline{H}_2$), 3.6–3.9(m, 1H, cyclohexyl —C$\underline{H}$), 6.4–6.9 (broad d,1$\overline{H}$, N$\underline{H}$); m/e 174 (M+H)+.

EXAMPLE 111

7-amino-2-(2-furyl)-5-($\underline{N}$-piperidinocarbonyl)-methylthio-[1,2,4]triazolo[1,5-a][1,3,5]triazine as a white solid from isopropanol m.p. 218°–220° C.; microanalysis, found: C,49.9; H,4.8; N,27.3%; $C_{15}H_{17}N_7O_2S$ requires: C,50.2; H,4.7; N,27.3%; NMR: 1.4–1.7 (complex, 6H, —C$\underline{H}_2$—), 3.48(m,4H, C$\underline{H}_2$NC$\underline{H}_2$), 4.19(s,2H, SC$\underline{H}_2$), 6.70(dd, 1H, furyl-4$\underline{H}$), 7.15(d, 1H, furyl-3$\underline{H}$), 7.90(m, 1H, furyl-5$\underline{H}$) 8.88(d,2H, N$\underline{H}_2$); m/e 360 (M+H)+.

The thiol starting material was prepared by a procedure similar to that described in Example 110, but using piperidine instead of cyclohexylamine. The product was distilled to give a viscous yellow oil which was used directly.

EXAMPLE 112

7-amino-5-([(l-propyl)aminocarbonyl]methylthio)-2-(2-furyl-[1,2,4]triazolo[1,5-a][1,3,5]triazine as a white solid from isopropanol, m.p. 203°–205° C.; microanalysis, found: C, 46.6; H,4.8; N,28.5% $C_{13}H_{15}N_7O_2S$ (0.15)$C_3H_7OH$ requires C,46.9; H,4.7; N,28.5%; NMR: 0.84(t,3H C$\underline{H}_3$), 1.43(m,2H, C$\underline{H}_2$CH$_3$), 3.04(q,2H, C$\underline{H}_2$N), 3.87(s, C$\underline{H}_2$S), 6.69(dd, 1H, furyl-4$\underline{H}$), 7.15(d,1H, furyl-3$\underline{H}$), 7.91(d,1H, furyl-5$\underline{H}$), 8.07(t,1$\overline{H}$, N$\underline{H}$) and 8.90(d,2$\overline{H}$, N$\underline{H}_2$); m/e 334 (M+H)+.

The thiol starting material was prepared in a manner similar to that described in Example 110, but using 1-propylamine instead of cyclohexylamine. The product was distilled to give a pale yellow viscous oil which was used directly.

EXAMPLE 113

Sodium hydride (150 mg of a 50% dispersion in oil) was added to a stirred solution of 7-amino-2-(2-furyl)-5-phenoxy[1,2,4]triazolo-[1,5-a][1,3,5]triazine (800 mg) in dimethylformamide (10 ml). The mixture was stirred until the effervescence had ceased and a clear solution had been obtained. Iodoethane (0.22 ml) was then added and the reaction mixture was stirred overnight at ambient temperature. Water (150 ml) and glacial acetic acid (1.0 ml) were then added and the resulting aqueous suspension was extracted with ethyl acetate (3×40 ml). The organic extracts were combined and washed with water (2×40 ml) and brine (40 ml), dried (MgSO$_4$) and evaporated to yield a pale brown gum (800 mg). This was purified by chromatography on silica eluting with dichloromethane containing ethyl acetate (4% v/v). The colourless foam thereby obtained was crystallised from tetrachloromethane to give 7-ethylamino-2-(2-furyl)-5-phenoxy-[1,2,4]triazolo[1,5-a][1,3,5]triazine as colourless crystals, m.p. 127°–129° C.; microanalysis, found: C,54.2, 54.1; H,4.0, 3.8; N,23.1, 23.1; Cl,10.2%; $C_{16}H_{14}N_6O_2.0.25CCl_4$ requires: C,54.1; H,3.9; N,23.3; Cl,9.8%; NMR: 1.2(t,3H, C$\underline{H}_3$), 3.54(m,2H, C$\underline{H}_2$), 6.7(q,1H, furyl-4$\underline{H}$), 7.1(dd, 1$\overline{H}$, furyl 3$\underline{H}$), 7.2–7.5 (complex, 5H, phenyl-$\underline{H}$), 7.9(q,1H, furyl-5$\underline{H}$), 9.35(t, 1H, N$\underline{H}$); m/e 322 (M+).

EXAMPLE 114

Using a procedure similar to that described in Example 113, but using iodomethane instead of iodoethane, 7-methylamino-2-(2-furyl)-5-phenoxy-[1,2,4]-triazolo[1,5-a][1,3,5]triazine was prepared as colourless fluffy crystals (crystallised from ethanol), m.p.

220°-222° C.; microanalysis, found: C,58.6; H,3.7; N,27.4%; C$_{15}$H$_{12}$N$_6$O$_2$ requires: C,58.4; H,3.9; N,27.3%; NMR: 3.0(s,3H, C$\underline{H}_3$), 6.7(q,1H, furyl-4$\underline{H}$), 7.1(d,1H, furyl-3$\underline{H}$), 7.2-7.5 (complex, 5H, phenyl-$\underline{H}$), 7.9(d,1H, furyl-5$\underline{H}$), 9.25(s,1H, N$\underline{H}$); m/e 308 (M$^+$).

EXAMPLE 115

Using a procedure similar to that described in Example 1, but using the appropriate alcohol instead of phenol, 7-amino-2-(2-furyl)-5-(4-[$\underline{N}$-(1-propyl)aminocarbonylmethyl]phenoxy)-[1,2,4]triazolo[1,5-a][1,3,5]triazine was prepared as a white solid from ethanol, m.p. 240°-242° C., microanalysis, found: C,57.7; H,4.7; N,24.8%; C$_{19}$H$_{19}$N$_7$O$_3$ requires: C,58.0; H,4.8; N,25.0%; NMR: 0.87(t,3H, CH$_2$C$\underline{H}_3$), 1.45(m,2H, C$\underline{H}_2$CH$_3$), 3.04(q,2H, NC$\underline{H}_2$), 3.42(s,2H C$\underline{H}_2$CO), 6.68(dd, 1H, furyl-4$\underline{H}$) 7.1-7.4(A$_2$B$_2$ pattern, 4$\underline{H}$, phenyl-$\underline{H}$), 7.88(m, 1$\underline{H}$, furyl-5$\underline{H}$), 8.03(t, 1H, N$\underline{H}$); 8.96(d,2H, NH$_2$); m/e 394(M+H)$^+$.

The phenol starting material was prepared as follows:

To a solution of $\underline{N}$-(1-propyl)-4-acetoxyphenylacetamide (11.4 g) in methanol (25 ml) was added a solution of sodium carbonate (2.65 g) in water (50 ml), and the mixture stirred overnight at ambient temperature. The methanol was removed in vacuo and the aqueous residue acidified to pH2. The product was extracted with ethyl acetate (3×50 ml), and the organic extracts combined and washed with brine (50 ml), dried (MgSO$_4$). The solvent was evaporated to give N-(1-propyl)-4-hydroxyphenylacetamide as a yellow oil, essentially pure by TLC, NMR: 0.85(t,3H, C$\underline{H}_3$), 1.3-1.6(m,2H, C$\underline{H}_2$CH$_3$), 3.15(t,2H, C$\underline{H}_2$N), 3.5(s,2H, C$\underline{H}_2$Ar), 5.75 (broad t,1H, N$\underline{H}$), 6.85(d,2H, phenyl-$\underline{H}$), 7.05(d,2H, phenyl-$\underline{H}$) (the spectrum also contained peaks due to ethyl acetate); m/e 194 (M+H)$^+$.

The requisite N-(1-propyl )-4-acetoxyphenylacetamide was prepared as follows:

To an ice-cold solution of 1-propylamine (9 g) in water (50 ml) was added solution of 4-acetoxyphenylacetyl chloride (10.6 g) in diethyl ether (100 ml), keeping the temperature of the mixture between 15° and 25° C. with external cooling. The ether layer was separated, washed with brine and evaporated to give $\underline{N}$-(1-propyl)-4-acetoxyphenylacetamide as a pale yellow oil, essentially pure by TLC, which was used without further purification or characterisation.

EXAMPLE 116

Using a similar procedure to that described in Example 3 but starting from 7-amino-2-(5-methyl-2-furyl)-5-methylsulphonyl-[1,2,4]triazolo[1,5-a][1,3,5]triazine obtained from the corresponding 5-methylthio compound described in Example 47, and the appropriate amine, there was preprared 7-amino-5-[2-(4-hydroxyphenylethyl)]amino2-(5-methyl-2-furyl)-[1,2,4]-triazolo[1,5-a][1,3,5]triazine as a crystalline solid from ethanol, m.p. 290°-292° C.; microanalysis, found: C,57.4; H,5.8; N,24.7%; C$_{17}$H$_{17}$N$_7$O$_2$.C$_2$H$_5$OH requires C,57.4; H,5.8; N,24.7; NMR 2.36(s,3H, C$\underline{H}_3$), 2.72(t,2H, NC$\underline{H}_2$), 3.44(m,2H, C$\underline{H}_2$-phenyl), 6.28(d,1H, furyl-4$\underline{H}$), 6.68 and 7.03 (A$_2$B$_2$ pattern, 4H, phenyl-$\underline{H}$), 6.93(d,1$\underline{H}$, furyl-3$\underline{H}$ ), 7.88(t,1H, N$\underline{H}$), 8.08(br s, 2$\underline{H}$, N$\underline{H}_2$) and 9.12(s,1$\underline{H}$, O$\underline{H}$); m/e 352 (M+H)$^+$.

EXAMPLE 117

A solution of 5,7-diphenoxy-2-(5-isoxazolyl)-[1,2,4-]triazolo[1,5-a][1,3,5]triazine (3.5 g) in ethanolic ammonia (200 ml) was allowed to stand at ambient temperature for 1 hour. The solvent was then evaporated and the residue was purified by chromatography on silica-gel eluting sequentially with dichloromethane-ethyl acetate mixtures 9:1 v/v to give a pale yellow solid (1.61 g). This was crystallised from ethanol to give 7-amino-2-(5-isoxazolyl)-5-phenoxy-[1,2,4]triazolo[1,5-a][1,3,5]triazine as colourless crystals, m.p. 255°-257° C. (decomposition); microanalysis, found: C,53.0; H,4.2; N,29.3%; C$_{13}$H$_9$N$_7$O$_2$(0.75)C$_2$H$_5$OH requires C,52.8; H,4.1; N,29.7%; NMR: 7.12(d,1H, isoxazolyl-3$\underline{H}$), 7.2-7.6 (complex 5H, phenyl-$\underline{H}$), 8.79(d, 1H; isoxazolyl-4$\underline{H}$) and 9.13 (s,2H, N$\underline{H}_2$); m/e 296 (M+H)$^+$.

The starting material was prepared as follows:

(a) A solution of 5-isoxazolylcarbonyl chloride (6.6 g) in dichloromethane was added to a stirred solution of 2,4-diphenoxy-6-hydrazino-[1,3,5]triazine (15 g) in dichloromethane at 0° C. After stirring for 2 hours at ambient temperature, the organic solution was washed with water (×2), brine (×1), dried and evaporated to yield a yellow foam (18.0 g). The residue was crystallised from toluene to give pale yellow crystals (11.0 g) which were used directly.

(b) A suspension of phosphorus pentoxide (20 g) and the product of step (a) (8.0 g) in toluene (250 ml) was heated under reflux for 18 hours. The solvent was evaporated and the residue partitioned between water and dichloromethane. The organic solution was washed with water, saturated sodium bicarbonate solution, water and brine, dried and evaporated to give as a brown solid 5,7-diphenoxy-2-(5-isoxazoly)-[1,2,4-]triazolo[1,5-a][1,3,5-]triazine (3.6 g).

EXAMPLE 118

A solution of 7-amino-2-(2-furyl)-5-phenoxy-[1,2,4]triazolo[1,5-a][1,3,5]triazine (1.01 g) and tyramine (1.43 g) in dimethylformamide (40 ml) was stirred at 100° C. until tlc analysis indicated that most of the phenoxy starting material had disappeared (2-3 hours). The solvent was removed in vacuo and the residue purified by chromatogrphy on silica (100 g) eluting with ethyl acetate. The solid (1.3 g) obtained was crystallised from ethyl acetate to give 7-amino-2-(2-furyl)-5-[2-(4-hydroxyphenylethyl]-amino[1,2,4]triazolo[1,5-a][1,3,5]triazine as colourless prisms m.p. 222°-225° C.; microanalysis, found: C,56.6; H,5.1; N,26.4%; C$_{16}$H$_{15}$N$_7$O$_2$.0.33 C$_4$H$_8$O$_2$ requires: C,56.8; H,4.8; N,26.7%; NMR: 2.75(t,2H, C$\underline{H}_2$ Ar), 3.4(t, 2H, C$\underline{H}_2$N) 6.7 (complex 3H furyl-4$\underline{H}$+phenyl-$\underline{H}$), 7.05 (complex, 3H, furyl-3$\underline{H}$+phenyl-$\underline{H}$), 7.4-7.6(dt,1H, N$\underline{H}$), 7.85(d,1H, furyl-5$\underline{H}$), 8.0-8.5(broad d,2H, N$\underline{H}_2$), 9.15(s,1H, O$\underline{H}$), the spectrum also contained signals due to ethyl acetate (0.33 mole); m/e 338 (M+H)$^+$.

The requisite 5-phenoxy starting material was prepared in a manner similar to that described in Example 117, but starting with 5,7-diphenoxy-2-(2-furyl)-[1,2,4]-triazolo[1,5-a][1,3,5]triazine, m.p. 246°-248° C. (crystallised from ethyl acetate); microanalysis, found: C,64.8; H,3.3; N,19.2%; C$_{20}$H$_{13}$N$_5$O$_3$ requires: C,64.7; H,3.5; N,18.9%; NMR: 6.7(dd, 1H, 3-furyl $\underline{H}$); 7.2-7.7 (complex, 11H, 4-furyl $\underline{H}$ and phenyl $\underline{H}$), 8.0(d, 1H, 5-furyl $\underline{H}$); m/e 372 (M+$\underline{H}$)$^+$.

The requisite 5,7-diphenoxy starting material was prepared in a manner similar to that described in Example 117(b) but starting with $\underline{N}$-2-(4,6-diphenoxy)-[1,3,5]-triazinyl-$\underline{N}$'-(2-furoyl)-hydrazine, m.p. 182°-184° C. (crystallised from 2-propanol, microanalysis, found: C,61.4; H,3.8; N,17.7%; C$_{20}$H$_{15}$N$_5$O$_4$ requires: C,61.7; H,3.9; N,18.0%; NMR: 6.65(dd,1H, 3-furyl $\underline{H}$); 7.0-7.6

(complex, 11H, 4-furyl-H, phenyl-H); 7.9(d,1H, 5-furyl-H); 9.95(broad s,1H, NH); 10.35(broad s,1H, NH); m/e 390 (M+H)+.

The requisite hydrazine starting material was prepared in a manner similar to that described in Example 117(a) using 2-furoyl chloride instead of isoxazole-5-carbonyl chloride.

EXAMPLE 119

Phenol (4.7 g) was added to a suspension of 7-amino-2-(2-furyl)-5-methylsulphonyl-pyrazolo[2,3-a][1,3,5]triazine (4.6 g) in 1,2-dimethoxyethane (120 ml) and 1,8-diazabicyclo[5.4.0]undec-7-ene (DBU, 2.8 ml). The mixture was heated under reflux for 1 hour. The solvent was removed in vacuo and the residue was purified by chromatography on silica (250 g) eluting with dichloromethane containing ethyl acetate (4% v/v) to give a colourless amorphous solid (1.25 g). This was crystallised from ethanol to give 7-amino-2-(2-furyl)-5-phenoxy-pyrazolo[2,3-a][1,3,5]triazine (0.9 g) as colourless needles, m.p. 275–277C; microanalysis, found: C,61.8; H,3.7; N,24.1%; $C_{15}H_{11}N_5O_2$ requires: C,61.4; H,3.8; N,23.9%; NMR: 6.4 (s,1H, =CH—), 6.65(q,1H, furyl-4H), 7.0(q,1H, furyl-3H ), 7.2(m,3H, phenyl-H), 7.4(m,2H, phenyl-H), 7.8(q,1H, furyl-5H), 8.4–8.8(d,2H, NH2); m/e 294 (M+H+).

The necessary methylsulphonyl starting material was prepared as follows:

To a cooled suspension of 7-amino-2-(2-furyl)-5-methylthiopyrazolo[2,3-a]-1,3,5-triazine (4.3 g) in dichloromethane (50 ml) was added a solution of 3-chloroperoxybenzoic acid (15 g, 50% w/w) in dichloromethane (100 ml), discarding the aqueous layer. The reaction mixture was allowed to warm to ambient temperature and stirred for 16 hours. The solvent was removed in vacuo and the residue was triturated with ethanol. The solid formed was collected by filtration, washed with ethanol and dried to give an off-white solid (19.4 g). This material was crystallised from ethanol to give 7-amino-2-(2-furyl)-5-methylsulphonyl-pyrazolo[2,3-a][1,3,5]triazine as a crystalline solid, m.p. 215°–219° C.; microanalysis, found: C,42.9; H,3.4; N,24.7%; $C_{10}H_9N_5O_3S$ requires: C,43.0; H,3.2; N,25.0%; NMR, 3.3(s,3H, CH3SO2—), 6.6 (d, 1H, furyl-4H), 6.8(s,1H, pyrazole-3H), 7.1(d, 1H, furyl-3H), 7.7(d,1H, furyl-5H); m/e 280 (M+H+).

The starting methylthio compound was itself prepared as follows:

An intimate mixture of 3-amino-5-(2-furyl)pyrazole (3.0 g; obtainable from the Maybridge Chemical Company Ltd., Tintagel, Cornwall) and dimethyl N-cyanodithioiminocarbonate (3.2 g) was heated at 180° C. for 5 minutes. The reaction mixture was cooled and the solid which formed was crystallised from ethanol to give 7-amino-2-(2-furyl)-5-methylthio-pyrazolo[2,3-a][1,3,5]triazine as a colourless crystalline solid, m.p. 234°–236° C.; microanalysis, found: C,48.9; H,3.7; N,28.0%; $C_{10}H_9N_5OS$ requires: C,48.6; H,3.6; N,28.3%; NMR: 2.5(s,3H, CH3S), 6.5(s,1H, pyrazole-CH), 6.7(q, 1H, furyl-4H), 7.0(q,1H, furyl-3H), 7.8(q,1H, furyl-5H), 8.2–8.7(br d, 2H, NH2); m/e 247 (M+).

EXAMPLE 120

Propylamine (6.0 ml) was added to a suspension of 7-amino-2-(2-furyl)-5-(methylsulphonyl)pyrazolo[1,5-a][1,3,5]triazine (2.0 g) in 1,2-dimethoxyethane (50 ml) (6.0 ml) and the mixture was heated under reflux for 2 hours. The solvent was removed in vacuo and the residue was purified by chromatography on silica (100 g) eluting with an increasing concentration of ethyl acetate in dichloromethane to give a white solid (0.76 g). This was crystallised from ethanol to give 7-amino-2-(2-furyl)-5-(propylamino)pyrazolo[2,3-a][1,3,5]triazine, as a solid, m.p 221°–223° C.; microanalysis, found: C, 55 6; H, 5.3; N, 32.5%; $C_{12}H_{14}N_6O$ requires C, 55.8; H, 5.5; N, 32.5%; NMR: 0.89(t, 3H, CH3), 1.53(m, 2H, CH2), 3.20(m, 2H, CH2N), 6.05(s, 1H, pyrazole-3H), 6.62(dd, 1H, furyl-4H), 6.90(d, 1H, furyl-3H), 6.95(br s, 1H, NH), 7.78(d 1H, furyl-5H) and 7.8(br, 2H, NH2); m/e 258 (M+).

EXAMPLES 121–133

Using a similar procedure to that described in Example 119, but using the appropriate phenol or hydroxy compound, the following compounds of formula I were obtained:

EXAMPLE 121

7-amino-5-(4-chlorophenoxy)-2-(2-furyl)-pyrazolo[2,3-a][1,3,5]triazine, as a solid, m.p. >300° C. (from ethanol); microanalysis, found: C, 54.4; H, 3.2; N, 20.9; H2O, 0.1%; $C_{15}H_{10}N_5ClO_2$. 0.05H2O requires: C, 54.8; H, 3.1; N, 21.3; H2O, 0.3%; NMR: 6.4(s, 1H, pyrazole-3H), 6.6(dd, 1H, furyl-4H), 7.0(d, 1H, furyl-3H), 7.2–7.3(m, 2H, phenyl-H), 7.4–7.5(m, 2H, phenyl-H), 7.8(d, 1H, furyl-5H), 8.3–8.9(d, 2H, NH2); m/e 327 (M+);

EXAMPLE 122

7-amino-5-ethoxy-2-(2-furyl)pyrazolo[2,3-a][1,3,5]triazine, as a colourless solid, (using ethanol as reaction solvent), m.p. 206°–208° C. recrystallised from ethanol); microanalysis, found: C, 54.1; H, 4.5; N, 28.3%; $C_{11}H_{11}N_5O_2$ requires: C, 53.9; H, 4.5; N, 28.6%; NMR: 1.3(t, 3H, CH3CH2O), 4.3(q, 2H, CH3CH2O), 6.4(s, 1H, pyrazole-3H), 6.65(dd, 1H, furyl-4H), 7.0(d, 1H, furyl-3H), 7.0(d, 1H, furyl-5H), 8.0–8.6(br d, 2H, —NH2); m/e 245 (M+);

EXAMPLE 123

7-amino-5-(3-chlorophenoxy)-2-(2-furyl)-pyrazolo[2,3-a][1,3,5]triazole, as a solid, m.p. 252°–254° C., (recrystallised from toluene); microanalysis, found: C, 55.4; H, 3.0; N, 21.2%; $C_{15}H_{10}N_5ClO_2$ requires: C, 55.0; H, 3.1; N, 21.4%; NMR: 6.45(s, 1H, pyrazole-3H), 6.65(dd, 1H, furyl-4H), 7.0(d, 1H, furyl-3H), 7.1–7.5(m, 4H, phenyl-H), 7.8(d, 1H, furyl-5H), 8.3–9.0(br d, 2H, —NH2); m/e 328 (M+H)+;

EXAMPLE 124

7-amino-2-(2-furyl)-5-(3-methoxyphenoxy)-pyrazolo[2,3-a][1,3,5]triazine, as a solid, m.p. 227°–229° C. (recrystallised from toluene); microanalysis, found: C, 59.8; H, 3.9; N, 21.6%; $C_{16}H_{13}N_5O_3$ requires: C, 59.4; H, 4.1; N, 21.7%; NMR: 3.8(s, 3H, CH3O), 6.4(s, 1H, pyrazole-3H), 6.65(dd, 1H, furyl-4H), 6.8(m, 3H, phenyl-H), 7.0(d, 1H, furyl-3H), 7.3(m, 1H, phenyl-H), 7.8(d, 1H, furyl-5H), 8.3–8.9(br d, 2H, —NH2); m/e 324 (M+H)+;

EXAMPLE 125

7-amino-5-(1-butoxy)-2-(2-furyl)pyrazolo[2,3-a][1,3,5]triazine, (using butanol as reaction solvent), as a solid, m.p. 171°–173° C. (recrystallised from toluene); microanalysis, found: C, 57.4; H, 5.4; N, 25.3%; $C_{13}H_{15}N_5O_2$ requires: C, 57.1; H, 5.5; N, 25.6%; NMR:

1.0(t, 3H, C$\underline{H}_3$), 1.3–1.5(m, 2H, C$\underline{H}_3$CH$_2$), 1.6–1.8(m, 2H, CH$_3$CH$_2$C$\underline{H}_2$), 4.2(t, 2H, C$\underline{H}_2$O—), 6.4(s, 1H, pyrazole-3$\underline{H}$), 6.65(dd, 1H, furyl-4$\underline{H}$), 7.0(d, 1H, furyl-3$\underline{H}$), 7.8(d, 1H, furyl-5$\underline{H}$), 8.1–8.7(br d, 2H, N$\underline{H}_2$); m/e 274 (M+H)$^+$;

EXAMPLE 126

7-amino-5-(4-cyanophenoxy)-2-(2-furyl)pyrazolo[2,3-a][1,3,5]triazine, as a solid, m.p. 307°–309° C., (recrystallised from ethanol), microanalysis, found: C, 60.2; H, 3.0; N, 26.2%; C$_{16}$H$_{10}$N$_6$O$_2$ requires: C, 60.4; H, 3.2; N, 26.4%; NMR: 6.45(s, 1H, pyrazole-3$\underline{H}$), 6.65(dd, 1H, furyl-4$\underline{H}$), 7.0(d, 1H, 3-furyl $\underline{H}$), 7.4–7.5(d, 2H, phenyl-$\underline{H}$), 7.85(d, 1H, furyl-5$\underline{H}$), 7.9–8.0(d, 2H, phenyl-$\underline{H}$), 8.4–9.0(br d, 2H, N$\underline{H}_2$); m/e 319 (M+H)$^+$;

EXAMPLE 127

7-amino-2-(2-furyl)-5-(2-furylmethoxy)pyrazolo[2,3-a][1,3,5]triazine, as a solid, m.p. 205°–207° C. (recrystallised from ethyl acetate); microanalysis, found: C, 56.7; H, 3.8; N, 23.3%; C$_{14}$H$_{11}$N$_5$O$_3$ requires: C, 56.6; H, 3.7; N, 23.6%; NMR: 5.3(s, 2H, C$\underline{H}_2$O—), 6.45(s, H, pyrazole-3$\underline{H}$), 6.5(dd, 1H, furyl-4$\underline{H}$), 6.6(d, 1H, furyl-3$\underline{H}$), 6.65(dd, 1H, furyl-4$\underline{H}$), 7.0(d, 1H, furyl-3$\underline{H}$), 7.7(d, 1H, furyl-5$\underline{H}$), 7.85(d, 1H, 5-furyl $\underline{H}$), 8.1–8.8(br d, 2H, N$\underline{H}_2$); m/e 298 (M+H)$^+$;

EXAMPLE 128

7-amino-5-(3-cyanophenoxy)-2-(2-furyl)pyrazolo[2,3-a][1,3,5]triazine, as a solid, m.p. 261°–263° C., (recrystallised from ethanol); microanalysis, found: C, 60.0; H, 3.2; N, 26.2%; C$_{16}$H$_{10}$N$_6$O$_2$ requires: C, 60.4; H, 3.2; N, 26.4%; NMR: 6.45(s, 1H, pyrazole-3$\underline{H}$), 6.65(dd, 1H, furyl-4$\underline{H}$), 7.0(d, 1H, furyl-3$\underline{H}$), 7.5–7.9(m, 5H, phenyl-$\underline{H}$+furyl-5$\underline{H}$), 8.4–9.0(br d, 2H, N$\underline{H}_2$); m/e 319 (M+H)$^+$;

EXAMPLE 129

7-amino-5-(2-[ethylsulphinyl]ethoxy)-2-(2-furyl)-pyrazolo[2,3-a[1,3,5]triazine, as a solid, m.p. 182°–184° C., (recrystallised from ethanol); microanalysis, found: C, 48.9; H, 4.8; N, 21.9%; C$_{13}$H$_{15}$N$_5$SO$_3$ requires: C, 48.6; H, 4.7; N, 21.8%; NMR: 1.2(t, 3H, C$\underline{H}_3$), 2.6–3.3(m, 4H, C$\underline{H}_2$.SO.C$\underline{H}_2$), 4.5–4.8(m, 2H, C$\underline{H}_2$O), 6.45(s, 1H, pyrazole-3$\underline{H}$), 6.65(dd, 1H, furyl-4$\underline{H}$), 7.0(d, 1H, furyl-3$\underline{H}$), 7.85(d, 1H, furyl-5$\underline{H}$), 8.1–8.8(br d, 2H, N$\underline{H}_2$); m/e 322 (M+H)$^+$;

EXAMPLE 130

7-amino-5-(2-fluorophenoxy)-2-(2-furyl)pyrazolo[2,3-a][1,3,5]triazine, as a solid, m.p. 253°–255° C., (recrystallised from ethanol); microanalysis, found: C, 57.6; H, 3.1; N, 22.5%; C$_{15}$H$_{10}$N$_5$FO$_2$ requires: C, 57.8; H, 3.2; N, 22.5%; NMR: 6.45(s, 1H, pyrazole-3$\underline{H}$), 6.65(dd, 1H, furyl-4$\underline{H}$), 7.0(d, 1H, furyl-3$\underline{H}$), 7.3–7.5(m, 4H, phenyl-$\underline{H}$), 7.8(d, 1H, furyl-5$\underline{H}$), 8.4–9.0(br d, 2H, N$\underline{H}_2$); m/e 312 (M+H)$^+$;

EXAMPLE 131

7-amino-2-(2-furyl)-5-(3-isoxazolyloxy)pyrazolo[2,3-a][1,3,5]triazine, as a solid, m.p. 235°–237° C. (recrystallised from 2-propanol); microanalysis, found: C, 50.81 H, 2.9; N, 28.9%; C$_{12}$H$_8$N$_6$O$_3$. 0.1C$_3$H$_7$OH requires: C, 50.8; H, 3.1; N, 28.9%; NMR: 6.45(s, 1H, pyrazole-3$\underline{H}$), 6.65(dd, 1H, furyl-4$\underline{H}$), 6.75(d, 1H, isoxazole-4$\underline{H}$), 7.05(d, 1H, furyl-3$\underline{H}$), 7.85(d, 1H, furyl-5$\underline{H}$), 8.9(d, 1H, isoxazole-5$\underline{H}$), 8.5–9.2(br d, 2H, N$\underline{H}_2$)[spectrum also contains signals for 2-propanol (0.1 mole)]; m/e 284 (M$^+$);

EXAMPLE 132

7-amino-2-(2-furyl)-5-[3-(1,2,5-thiadiazolyl)oxy]-pyrazolo[2,3-a][1,3,5]triazine, as a solid, m.p. 246°–248° C. (recrystallised from ethanol); microanalysis, found: C, 43.9; H, 2.0; N, 32.7%; C$_{11}$H$_7$N$_7$SO$_2$ requires: C, 43.8; H, 2.3; N, 32.6%; NMR: 6.55(s, 1H, pyrazole-3$\underline{H}$), 6.65(dd, 1H, furyl-4$\underline{H}$), 7.05(d, 1H, furyl-3$\underline{H}$), 7.85(d, 1H, furyl-5$\underline{H}$), 8.9(s, 1H, 4-thiadiazole $\underline{H}$), 8.6–9.2(br d, 2H, N$\underline{H}_2$); m/e 301 (M$^+$); and

EXAMPLE 133

7-amino-2-(2-furyl)-5-(3-pyridyloxy)pyrazolo[2,3-a][1,3,5]triazine, as a solid, m.p. 278°–280° C. (recrystallised from ethanol); microanalysis, found: C, 57.2; H, 3.1; N, 28.2%; C$_{14}$H$_{10}$N$_6$O$_2$ requires: C, 57.1; H, 3.4; N, 28.6%; NMR: 6.45(s, 1H, pyrazole-3$\underline{H}$), 6.65(dd, 1H, furyl-4$\underline{H}$), 7.0(d, 1H, furyl-3$\underline{H}$), 7.5(dd, 1H, pyridyl-5$\underline{H}$), 7.7(m, 1H, pyridyl-4$\underline{H}$), 7.8(d, 1H, furyl-5$\underline{H}$), 8.45(dd, 1H, pyridyl-6$\underline{H}$), 8.55(d, 1H, pyridyl-2$\underline{H}$), 8.4–9.0(br d, 2H, N$\underline{H}_2$); m/e 294 (M$^+$).

EXAMPLE 134–141

Using a similar procedure to that described in Example 120, but using the appropriate amino compound, the following compounds of formula I were prepared:

EXAMPLE 134

7-amino-2-(2-furyl)-5-(piperidino)pyrazolo[2,3-a][1,3,5]triazine, as a solid, m.p 274°–276° C.; (recrystallised from ethanol) microanalysis, found: C, 58.8; H, 5.7; N, 29.3%; C$_{14}$H$_{10}$N$_6$O requires: C, 59.1; H, 5.7; N, 29.6%; NMR: 1.68(m, 6H, C$\underline{H}_2$), 3.88(t, 4H, C$\underline{H}_2$N C$\underline{H}_2$), 6.22(s, 1H, pyrazole-3$\underline{H}$), 6.78(dd, 1H, furyl-4$\underline{H}$), 7.08(d, 1H, furyl-3$\underline{H}$), 7.96(s, 1H, furyl-5$\underline{H}$) and 8.05(br s,2H, N$\underline{H}_2$); m/e 284 (M$^+$);

EXAMPLE 135

7-amino-2-(2-furyl)-5-(exo-norbornylamino)-pyrazolo[2,3-a][1,3,5]triazine, as a solid, m.p. 247°–249° C., (recrystallised from ethanol); microanalysis, found: C, 61.7; H, 5.8; N, 26.9%; C$_{16}$H$_{18}$N$_6$O requires: C, 61.9; H, 5.8; N, 27.1%; NMR: 1.0–1.7(complex, 8H, C$\underline{H}_2$), 2.19(s, 2H, CHC$\underline{H}_2$), 3.67(br, 1H, C$\underline{H}$NH), 6.03(s, 1H, pyrazole-3$\underline{H}$), 6.60(dd, 1H, furyl-4$\underline{H}$), 6.74(d, 1H, NHC$\underline{H}$), 6.67(d, 1H, furyl-3$\underline{H}$), 7.67(br s, 2H, N$\underline{H}_2$) and 7.75(d, 1H, furyl-5$\underline{H}$); m/e 310 (M$^+$);

EXAMPLE 136

7-amino-5-cyclohexylamino-2-(2-furyl)pyrazolo[2,3-a][1,3,5]triazine, as a solid, m.p. 218°–220° C., (recrystallised from ethanol); microanalysis, found: C, 60.4; H, 5.9; N, 28.0%; C$_{15}$H$_{18}$N$_6$O requires: C, 60.4; H, 6.0; N, 28.2%; NMR: 1.0–2.0(complex, 10H, C$\underline{H}_2$), 3.69(br s, 1H, N$\underline{H}$), 6.02(s, 1H, pyrazole-3$\underline{H}$), 6.61(dd, 1H, furyl-4$\underline{H}$), 6.70(d, 1H, N$\underline{H}$), 6.88(d, 1H, furyl-3$\underline{H}$), 7.71(br, 2$\underline{H}$, N$\underline{H}_2$) and 7.76(dd, 1H, furyl-5$\underline{H}$); m/e 298 (M$^+$);

EXAMPLE 137

7-amino-2-(2-furyl)-5-anilinopyrazolo[2,3-a][1,3,5]triazine, as a solid, m.p. 284°–286° C., (recrystallised from ethanol); microanalysis, found: C, 61.7; H, 4.1; N, 28.1%; C$_{15}$H$_{12}$N$_6$O 0.05C$_2$H$_5$OH requires: C, 61.6; H, 4.2; N, 28.5%; NMR: 6.25(s, 1H, pyrazole-3$\underline{H}$); 6.66(dd, 1H, furyl-4$\underline{H}$), 6.98(complex, 2H, furyl-3$\underline{H}$+p-phenyl-$\underline{H}$), 7.28(t, 2$\underline{H}$, m-phenyl-$\underline{H}$), 7.81(complex, 3$\underline{H}$, furyl-5H+o-phenyl-H), 8.08(br s, 2H, NH$_2$) and 9.27(br s, 1H, NH); m/e 292 (M+);

EXAMPLE 138

7-amino-5-(2-dimethylaminoethyl)amino-2-(2-furyl)-pyrazolo[2,3-a][1,3,5]triazine, as a solid, m.p. 169°–171° C. (recrystallised from ethanol); microanalysis, found: C, 54.5; H, 6.0; N, 34.4.%; C$_{13}$H$_{17}$N$_7$O requires: C, 54.4; H, 5.9; N, 34.2%; NMR: 2.73(s, 6H, NCH$_3$), 3.16(t, 2H, CH$_2$N), 3.56(t, 2H, CH$_2$N), 6.08(s, 1H, pyrazole-3H), 6.59(dd, 1H, furyl-4H), 6.89(d, 1H, furyl-3H) and 7.72(s, 1H, furyl-5H); m/e 288;

EXAMPLE 139

7-amino-2-(2-furyl)-5-(2-furylmethylamino)pyrazolo-[2,3-a][1,3,5]triazine, as a solid, m.p. 213°–215° C., (recrystallised from ethanol); microanalysis, found: C, 57.0; H, 3.9; N, 28.2%; C$_{14}$H$_{12}$N$_6$O$_2$ requires: C, 56.7; H, 4.05; N, 28.4%; NMR: 4.45(d, 2H, CH$_2$NH), 6.07(s, 1H, pyrazole-3H), 6.23(d, 1H, furylmethylamino-3H), 6.35(dd, 1H, furylmethylamino-4H), 6.60(dd, 1H, furyl-4H), 6.90(d, 1H, furyl-3H), 7.27(t, 1H, NH), 7.52(d, 1H, furylmethylamino-5H), 7.76(d, 1H, furyl-5H) and 7,85(br s 2H NH$_2$); m/e 296 (M)+;

EXAMPLE 140

(S)-7-amino-2-(2-furyl)-5-[α-methylbenzylamino ]pyrazolo[2,3-a][1,3,5]triazine, as a solid, m.p. 115°–118° C. (with decomposition), (recrystallised from methanol); microanalysis, found: C, 63.0; H, 5.4; N, 25.6%; C$_{17}$H$_{16}$N$_6$O 0.25 CH$_3$OH requires: C, 63.1; H, 5.2; N, 25.6%; NMR: 1.42(d, 3H, CH$_3$), 5.15(m, 1H, CHN), 6.00(s, 1H, pyrazole-3H), 6.60(dd, 1H, furyl-4H), 6.88(d, 1H, furyl-3H), 7.1–7.5(complex, 6H, NH+phenyl H) and 7.75(br d, 3H, NH$_2$+furyl-5H); m/e 320 (M)+; and

EXAMPLE 141

7-amino-2-(2-furyl)-5-(3-pyridylmethylamino)-pyrazolo[2,3-a][1,3,5]triazine, as a solid, m.p. 215°–217° C., (recrystallised from ethanol); microanalysis, found: C, 59.0; H, 4.1; N, 32.0%; C$_{15}$H$_{13}$N$_7$O requires: C, 58.7; H, 4.2; N, 31.9%; NMR: 4.5(d, 2H, NCH$_2$), 6.07(s, 1H, pyrazole-3H), 6.62(dd, 1H, furyl-4H), 6.8(d, 1H, furyl-3H), 7.32(dd, 1H, pyridyl-5H), 7.48(t, 1H, NH), 7.75(complex, 2H, furyl-5H+pyridyl-4H), 7.85(br, 2H, NH$_2$), 8.42(dd, 1H, pyridyl-6H) and 8.55(d, 1H, pyridyl-2H); m/e 307 (M)+.

EXAMPLE 142

Using a similar procedure to that described in Example 119, but using thiophenol instead of phenol, there was obtained 7-amino-2-(2-furyl)-5-[phenylthio)-pyrazolo[2,3-a][1,3,5]triazine, as a solid, m.p. >300° C. (with decomposition, (recrystallised from ethanol); microanalysis, found: C, 58.2; H, 3.5; N, 22.3%; C$_{15}$H$_{11}$N$_5$OS requires: C, 58.2; H, 3.6; N, 22.6%; NMR: 6.44(s, 1H, pyrazole-3H), 6.62(dd, 1H, furyl-4H), 6.99(d, 1H, furyl-3H), 7.49(complex, 3H, phenyl-m-+p-H), 7.61(complex, 2H, phenyl-o-H), 7.81(d, 1H, furyl-5H) and 8.51(br d, 2H, NH$_2$); m/e 310 (M+H)+.

EXAMPLE 143

4-(2-aminoethyl)phenol (1.37 g) was added to a stirred suspension of 7-amino-2-(2-furyl)-5-(methylsulphonyl)pyrazolo[2,3-a][1,3,5]triazine (1.4 g) in acetonitrile (150 ml) and the mixture was heated under reflux for 6 hours. The solvent was removed in vacuo and the residue was purified by chromatography on silica (100 g) eluting with dichloromethane containing methanol (5.0% v/v). The solid obtained was crystallised from ethanol to give 7-amino-2-(2-furyl)-5-[2-(4-hydroxyphenylethyl)]aminopyrazolo[2,3-a][1,3,5]triazine as a crystalline solid (0.36 g), m.p. 213°–215° C.; microanalysis, found: C,60.0; H 5.3; N 24.0%; C$_{17}$H$_{16}$N$_6$O$_2$ 0.3C$_2$H$_5$OH requires C,60.2; H,5.2; N,24.0%; NMR: 1.05(t, CH$_3$CH$_2$OH), 2.70(t, 2H, CH$_2$Ar), 3.4 (complex, NCH$_2$ and CH$_3$CH$_2$OH), 4.31(t, CH$_3$CH$_2$OH), 6.08(s, 1H, pyrazole-3H), 6.62(dd, 1H, furyl-4H), 6.7 and 7.05 (A$_2$B$_2$ pattern, 4H, phenyl-H), 6.86(t,1H, NH), 6.92(dd, 1H, furyl-3H), 7.8(br s, 2H, NH$_2$) and 9.12 (s, 1H, OH); m/e 337 (M+H)+.

EXAMPLES 144–148

Using a procedure similar to that described in Example 1, but using the appropriate phenol or hydroxy compound, the following compounds of formula I were obtained:

EXAMPLE 144

7-amino-5-(2-cyanophenoxy)-2-(2-furyl)pyrazolo[2-,3a][1,3,5]triazine as colourless prisms from ethanol, m.p. 296°–298° C. (decomposed); microanalysis, found: C, 60.0; H, 3.0; N, 26.1%; C$_{16}$H$_{10}$N$_6$O$_2$ requires; C, 60.4; H, 3.1; N, 26.4%; NMR: 6.5(s, 1H, pyrazole-3H), 6.65(q, 1H, furyl-4H), 7.0(q, 1H, furyl-3H), 7.4–7.6(m, 2H, phenyl-H), 7.7–8.0(m, 3H, phenyl-H and furyl-5H), 8.5–9.1(broad d, 2H, NH$_2$ ); m/e 319 (M+H)+.

EXAMPLE 145

7-amino-2-(2-furyl)-5-(2,3,4,5,6-pentafluorophenoxy)-pyrazolo[2,3-a][1,3,5]triazine as colourless crystals from ethanol, m.p. 285°–288° C.; microanalysis, found: C, 47.2; H, 1.7; N, C$_{15}$H$_6$F$_5$N$_5$O$_2$ requires: C, 47.0; H, 1.6; N, 18.3%; NMR: 6.50(s, 1H, pyrazole-3H), 6.65(dd, 1H, furyl-4H), 7.02(d, 1H, furyl-3H), 7.85(d, 1H, furyl-5H), 8.75–9.10(br d, 2H, NH$_2$); m/e 384 (M+H)+.

EXAMPLE 146

7-amino-2-(2-furyl)-5-(2-methoxycarbonylphenoxy) pyrazolo[2,3-a][1,3,5]triazine as colourless prisms from methanol, m.p. 249°–251° C.; microanalysis, found: C, 57.7; H, 3.6; N, 19.8%; C$_{17}$H$_{13}$N$_5$O$_4$ requires: C, 58.1; H, 3.7; N, 19.9%; NMR: 3.65(s, 3H, CH$_3$), 6.4(s, 1H, pyrazole-3H), 6.65(q, 1H, furyl-4H), 6.95(q, 1H, furyl-3H), 7.3–7.5(complex, 2H, phenyl-H), 7.7(t of d, 1H, phenyl-5H), 7.8(d, 1H, furyl-5H), 7.9(dd, 1H, phenyl-3H), 8.3–8.9(broad d, 2H, NH$_2$); m/e 325 (M+H)+.

EXAMPLE 147

7-amino-2-(2-furyl)-5-(4-N-(1-propyl)aminocarbonyl methoxy)phenoxypyrazolo[2,3-a][1,3,5]triazine as colourless crystals from ethanol, m.p. 224°–226° C.; microanalysis, found: C, 58.6; H, 4.7; N, 20.2%; C$_{20}$H$_{20}$N$_6$O$_4$ requires: C, 58.8; H, 4.9; N, 20.6%; NMR: 0.86(t, H, CH$_3$), 1.48(m, 2H, —CH$_2$—), 3.12(q, 2H, —CH$_2$N), 4.50(s, 2H, OCH$_2$CO), 6.40(s, 1H, pyrazole-3H), 6.65(dd, 1H, furyl-4H), 6.95–7.05 (complex, 3H, phenyl-H and furyl-3H), 7.10–7.20 (complex, 2H, phenyl-H), 7.83(d, 1H, furyl-5H), 8.10(t, 1H, CONH), 8.4–8.8(br d, 2H, NH$_2$); m/e 409 (M+H)+.

The phenol starting material was prepared as follows:

A solution of 1-propylamine (4.1 ml) and methyl 4-hydroxyphenoxyacetate (3.64 g) in methanol (50 ml) was left to stand for 72 hours at ambient temperature. The solvent was evaporated in vacuo and the residue taken up in ethyl acetate. The solution was washed sequentially with 1M HCl (2×25 ml) and brine (30 ml), dried (MgSO$_4$) and the solvent evaporated to give N-(1-propyl)-4hydroxyphenoxyacetamide as a red oil, NMR: 0.95(t, 3H, CH$_3$), 1.55(m, 2H, CH$_2$), 3.3(q, 2H, CH$_2$N), 4.4(s, 2H, CH$_2$O), 6.5–6.7(broad s, 1H, OH), 6 8(s, 4H, phenyl-H); m/e 227 (M+NH$_4$)$^+$, 210(M+H)$^+$.

EXAMPLE 148

7-amino-5-(3-methoxycarbonylphenoxy)-2-(2-furyl)-pyrazolo[2,3-a][1,3,5]triazine as a solid from ethanol, m.p. 244°–247° C.; microanalysis, found: C, 57.7; H, 3.8; N, 19.8%; C$_{17}$H$_{13}$N$_5$O$_4$ requires: C, 58.1; H, 3.7; N, 19.9%; NMR: 3.89(s, 3H, CO$_2$CH$_3$), 6.42(s, 1H, pyrazole-3H), 6.65(dd, 1H, furyl-4H), 6.99(dd, 1H, furyl-3H), 7.5–7.9(complex, 5H, furyl-5H and phenyl-H) and 8.64(d, 2H, NH$_2$); m/e 352 (M+H)$^+$.

EXAMPLES 149–152

Using a procedure similar to that described in Example 120, but using the appropriate amino compound, the following compounds of formula I was obtained:

EXAMPLE 149

7-amino-2-(2-furyl)-5-(2-phenylethylamino)-pyrazolo[2,3-a][1,3,5]triazine as off-white crystals from ethanol, m.p. 225°–227° C.; microanalysis, found: C, 63.3; H, 4.9; N, 26.1%; C$_{17}$H$_{16}$N$_6$O requires: C, 63.7; H, 5.0; N, 26.2%; NMR: 2.74(t, 2H, CH$_2$), 3.97(q, 2H, CH$_2$N), 6.05(s, 1H, pyrazole-3H), 6.62(dd, 1H, furyl-4H), 6.90(complex, 2H, furyl-3H and NH), 7.14–7.36-(complex, 5H, phenyl-H), 7.78(d, 1H, furyl-5H), 7.80(br, 2H, NH$_2$); m/e 321 (M+H)$^+$.

EXAMPLE 150

7-amino-5-cyclopropylmethylamino-2-(2furyl)-pyrazolo[2,3-a][1,3,5]-triazine as off-white crystals from toluene, m.p. 200°–202° ; microanalysis, found: C, 58.0; H, 5.4; N, 30.8%; C$_{13}$H$_{14}$N$_6$O requires: C, 57.8; H, 5.2; N, 31.1%; NMR: 0.17–0.29(complex, 2H, cyclopropyl-CH$_2$), 0.31–0.45(complex 2H, cyclopropyl CH$_2$), 0.95–1.18(complex, 1H, cyclopropyl CH), 3.13(t, 2H, CH$_2$N), 6.03(s, 1H, pyrazole-3H), 6.62(dd, 1H, furyl-4H), 6.88(d, 1H, furyl-3H), 6.93(br s, 1H, NH), 7.76(d, 1H, furyl-5H) and 7.77(br, 2H, NH$_2$); m/e 270 (M+).

EXAMPLE 151

7-amino-5-[2-(4-aminosulphonylphenyl)ethyl]amino-2-(2-furyl)pyrazolo[2,3-a][1,3,5]triazine as off-white crystals from ethanol, m.p. 245°–248° C.; microanalysis, found: C, 50.6; H, 4.7; N, 23.2; H$_2$O, 2.2%; C$_{17}$H$_{17}$N$_7$O$_3$S. 0.3C$_2$H$_5$OH. 0.5H$_2$O requires: C, 50.3; H, 4.7; H, 23.2; H$_2$O, 2.2%; NMR: 2.93(t, 2H, CH$_2$), 3.43–3.55(complex, 2H, CH$_2$N), 6.08(s, 1H, pyrazole-3H), 6.62(dd, 1H, furyl-4H), 6.90(d, 1H, furyl-3H), 6.96(br t, 1H, NH), 7.25(s, 2H, SO$_2$NH$_2$), 7.41–7.46(d, 2H, phenyl-H), 7.73–7.77(brd, 5H, furyl-5H, phenyl-H and NH$_2$); m/e 399 (M+).

EXAMPLE 152

7-amino-2-(2-furyl)-5-[2-(4-pivaloyloxyphenyl)ethyl]aminopyrazolo [2,3-a][1,3,5]triazine as pale yellow prisms from 2-propanol, m.p. 211°–213° C.; microanalysis, found: C, 62.4; H, 6.1; N, 19.8%; C$_{22}$H$_{24}$N$_6$O$_3$ requires: C, 62.8; H, 5.8; N, 20.0%; NMR: 1.3(s, 9H, (CH$_3$)$_3$), 2.85(t, 3H, CH$_2$ Ar), 3.5(m, 2H, CH$_2$N), 6.05(s, 1H, pyrazole-3H), 6.6(q, 1H, furyl-4H), 6.9(q, 1H, furyl-3H), 7.0(d, 2H, phenyl-H), 7.75(d, 2H, phenyl-H), 7.5–8.0(complex, 4H, NH$_2$, NH and furyl-5H); m/e 421 (M+H)$^+$.

The requisite amine starting material was prepared as follows:

A solution of pivaloyl chloride (10.0 ml) was added dropwise to a stirred solution of tyramine (10.2 g) in a dichloromethane/trifluoroacetic acid mixture (1:1 v/v). The reaction mixture was stirred for 4 hours and the solvents then removed in vacuo. The syrupy residue was triturated with an ethyl acetate/diethyl ether mixture (3:1 v/v) to give 2-(4-pivaloyloxyphenyl)ethylamine as a colourless trifluoroacetate salt, m.p. 255°–257° C.; NMR: 1.3(s, 9H, pivaloyl-H), 2.85(m, 2H, CH$_2$Ph), 3.05(m, 2H, CH$_2$N), 7.05(d, 2H, phenyl-H), 7.3(d, 2H, phenyl-H), 8.0(broad s, 3H, NH$_3$); m/e 222 (M+H)$^+$.

EXAMPLES 153–157

Using a procedure similar to that described in Example 119, but using an appropriate thiol compound instead of phenol, the following compounds of formula I were obtained:

EXAMPLE 153

7-amino-2-(2-furyl)-5-(2-furylmethylthio)-pyrazolo[2,3-a][1,3,5]triazine as colourless crystals from ethanol, m.p. 207°–209° C.; microanalysis, found: C, 53.8; H, 3.4; N, 22.3%; C$_{14}$H$_{11}$N$_5$O$_2$S requires: C, 53.7; H, 3.5; N, 22.4%; NMR: 4.45(s, 2H, CH$_2$S), 6.40(complex, 2H, furyl 3'H and 4'H), 6.55(s, 1H, pyrazole-3H), 6.67(dd, 1H, furyl-4H), 7.03(d, 1H, furyl-3H), 7.58(s, 1H, furyl-5H), 7.84(d, 1H, furyl-5H), 8.40–8.70(br d, 2H, NH$_2$); m/e 314 (M+H)$^+$.

EXAMPLE 154

7-amino-5-cyclopentylthio-2-(2-furyl)pyrazolo[2,3a][1,3,5]triazine as colourless plates from ethanol, m.p. 226°–228° C.; microanalysis, found: C, 56.2; H, 5.4; N, 23.2%; C$_{14}$H$_{15}$N$_5$SO requires: C, 55.8; H, 5.0; N, 23.2%; NMR: 1.4–1.8(complex, 6H, cyclopentyl-H), 2.1–2.3-(complex, 2H, cyclopentyl-H), 3.8–4.0(complex, 1H, cyclopentyl-1H), 6.5(s, 1H, pyrazole-3H, 6.65(q, 1H, furyl-4H), 7.0(d, 1H, furyl-3H), 7.8(d, 1H, furyl-5H), 8.1–8.7(broad d, 2H, NH$_2$); m/e 301 (M)$^+$.

EXAMPLE 155

7-amino-2-(2-furyl)-(N-(1-propyl)aminocarbonyl methylthio)pyrazolo[2,3-a][1,3,5]triazine as yellow crystals from ethanol; m.p. 250°–253° C.; microanalysis, found: C, 50.5; H, 4.7; N, 25.0%; C$_{14}$H$_{16}$N$_6$O$_2$S requires: C, 50.6; H, 4.8; N, 25.3%; NMR: 0.75(t, 3H, CH$_3$), 1.42(m, 2H, CH$_2$), 3.05(q, 2H, CH$_2$N), 3.82(s, 2H, SCH$_2$CO), 6.48(s, 1H, pyrazole-3H), 6.68(dd, 1H, furyl-4H), 7.05(d, 1H, furyl-3H), 7.85(d, 1H, furyl-5H), 8.05(t, 1H, NH); 8.40–8.70(br d, 2H, NH$_2$); m/e 333 (M+H)$^+$.

The starting material was prepared in a manner essentially similar to that described in Example 156, but using 1-propylamine instead of cyclohexylamine. The product was distilled to give a pale yellow viscous oil which was used directly.

EXAMPLE 156

7-amino-5-(cyclohexylaminocarbonylmethylthio)-2-(2-furyl pyrazolo [2,3-a][1,3,5]triazine as yellow crystals from isopropanol; m p. 253°–256° C.; microanalysis, found: C, 55.1; H, 5.5; N, 2.7%; C$_{17}$H$_{20}$N$_6$O$_2$S requires: C, 54.8; H, 5.4; N, 22.6%; NMR: 1.00–1.40(complex, 5H, cyclohexyl-H), 1.45–1.85(complex, 5H, cyclohexyl-H), 3.51(br, 1H, CH-N), 3.79(s, 2H, CH$_2$S), 6.46(s, 1H, pyrazole-3H̲), 6.66(dd, 1H, furyl-4H̲), 7.02(d, 1H, furyl-3H̲), 7.83(d, 1H, furyl-5H̲), 7.94(d, 1H, CONH̲), 8.2–8.8(br d, 2H, NH̲$_2$); m/e 373 (M+H)$^+$.

The thiol starting material was prepared as follows:

A solution of ethyl 2-mercaptoacetate (12 g) and cyclohexylamine (29.7 g) in ethanol (50 ml) was allowed to stand at ambient temperature for 72 hours, and was then refluxed for 6 hours. The solvent was evaporated and the residue dissolved in ethyl acetate (200 ml). The solution was washed sequentially with 2M HCl (3×50 ml), water (2×50 ml) and brine (50 ml) and the solvent removed in vacuo. The crude product was purified by chromatography on silica (eluting with dichloromethane/methanol 99:1 v/v) to give N-cyclohexyl-2-mercaptoacetamide as low-melting tan crystals; NMR: 1.0–2.0(complex, 11H, cyclohexyl-CH̲$_2$ and SH̲), 3.2(d, 2H, CH̲$_2$), 3.6–3.9(m, 1H, cyclohexyl-CH̲), 6.4–6.9(broad d, 1H̲, NH̲); m/e 174 (M+H)$^+$.

EXAMPLE 157

7-amino-2-(2-furyl)-5-(piperidinocarbonylmethylthio) pyrazolo[2,3-a][1,3,5]triazine as colourless crystals from isopropanol; m.p. 198°–200° C.; microanalysis, found, C, 53.8, H, 5.3; N, 23.5%; $C_{16}H_{18}N_6O_2S$ requires: C, 53.6; H, 5.0; N, 23.5%; NMR: 1.45–1.59(complex 6H, piperidine CH̲), 3.44–3.52(complex, 4H, NCH̲$_2$), 4.12(s, 2H, CH̲$_2$S), 6.48(s, 1H,pyrazole-3H̲), 6.64(dd, 1H, furyl-4H̲), 7.02(dd, 1H, furyl-3H̲), 7.82(d, 1H, furyl-5H̲), 8.2–8.8(br d, 2H, NH̲$_2$); m/e 359 (M+H$^+$).

The starting material was prepared by a procedure essentially similar to that described in Example 156, but using piperidine instead of cyclohexylamine. The product was distilled to give a viscous yellow oil which was used directly.

EXAMPLE 158

Using a procedure similar to that described in Example 118 there was prepared 2-(2-furyl)-5-[2-(4-hydroxyphenyl)ethyl]amino-7-methylamino-[1,2,4-]-triazolo[1,5-a][1,3,5]triazine, m.p. 248°–250° C.; microanalysis, found: C,58.0; H,4.9; N,28.0%; $C_{17}H_{17}N_7O_2$ requires: C,58.1; H,4.8; N,27.9%, NMR: 2.74(t,2H, CH̲$_2$Ar), 2.92 and 2.99 (d,3H, NHCH̲$_3$ rotamers), 3.45(m,2H, NHCH̲$_2$), 6.69 (complex, 3H̲, 2 phenyl-H̲ and furyl-4H̲), 7.04 (complex, 3H, 2 phenyl-H̲ and furyl-3H̲), 7.63(t,1H, —NH—CH$_2$), 7.86(d, 1H, furyl-5H̲), 8.48 and 8.63 (q,1H, NHCH$_3$ rotamers) 9.17(s,1H, OH̲); m/e 352 (M+H)$^+$.

EXAMPLE 159

Using a procedure similar to that described in Example 117 but starting from 5,7-diphenoxy-2-[5-(3-methylisoxazolyl)]-[1,2,4]triazolo[1,5-a][1,3,5]triazine, there was prepared 7-amino-2-[5-(3methylisoxazolyl)]-5-phenoxy-[1,2,4]-triazolo[1,5-a][1,3,5]triazine as colourless needles from ethanol m.p. 279°–281° C.; microanalysis, found: C,54.2; H,4.5; N,29.0%; $C_{14}H_{11}N_7O_2$ (0.6) $C_2H_5OH$ requires: C,54.2; H,4.3; N,29.1%; NMR: 2.33(s,3H, CH̲$_3$), 7.0(s,1H, isoxazolyl-4H̲) 7.2–7.6 (complex, 5H, phenyl-H̲) and 9.12(s,2H, NH̲$_2$); m/e 310 (M+H)$^+$.

The starting material was prepared as follows:

(a) A solution of 5-(3-methylisoxazolyl)carbonyl chloride (4.36 g) in dichloromethane was added to a stirred solution of 2,4-diphenoxy-6-hydrazino-[1,3,5]triazine (8.9 g) and triethylamine (3.03 g) in dichloromethane at 0° C. After stirring for 4 hours at ambient temperature, the organic solution was washed with water (×2), brine (×1), dried and evaporated to yield a foam (13.5 g). Chromatography on silica-gel and elution with dichloromethane methanol (1% v/v) gave the desired product (6.7 g). Crystallisation of an aliquot from ethanol gave a solid m.p. 195°–8° C.; NMR: 2.32(s,3H, CH$_3$); 6.93(s,1H, isoxazolyl-4H̲), 7.1–7.4 (complex, 10H, phenyl-H), 10.18 (s, 1H, NH̲) and 10.87 (s,1H CONH̲); m/e 405 (M+H)$^+$.

(b) A solution of the acylated hydrazine (2.02 g) and p-toluene sulphonyl chloride (1.90 g) in pyridine (50 ml) was heated at 100° C. for 2 hours. The pyridine was removed on a rotary evaporator, the residue dissolved in dichloromethane and solution washed with 2N HCl (2×50 ml), water (50 ml) and brine (50 ml). The organic solution was dried ($MgSO_4$), filtered, evaporated and used directly.

EXAMPLE 160

Using a procedure similar to that described in Example 118 but starting from 7-amino-2-[5-(3-methylisoxazolyl)]-5-phenoxy[1,2,4]-triazolo[1,5-a]triazine, there was obtained 7-amino-5-[2-(4hydroxyphenyl)ethyl]amino-2-[5(3-methylisoxazolyl)]-[1,2,4]-triazolo[1,5-a]triazine, m.p. 233°–235° C.; microanalysis, found: C,54.7; H,4.8; N,31.1%; $C_{16}H_{16}N_8O_2$ (0.1) $C_2H_5OH$ requires: C,54.6; H,4.8; N,31.4%; NMR: 2.32(s,3H, CH̲$_3$), 2.71(t,2H, NCH̲$_2$); 3.42(m,2H, CH̲$_2$-phenyl), 6.68 and 7.03 ($A_2B_2$ patterns, 4H, phenyl-H̲), 6.90(s,1H, isoxazolyl-4H̲), 7.56 and 7.66 (t, 1H, CH$_2$NH̲), 8.27(brs, 2H, NH$_2$) and 9.15(s,1H, OH̲); m/e 353 (M+H)$^+$.

EXAMPLE 161

Using a procedure similar to that described in Example 3 there was obtained 7-amino-2-(2-furyl)-5-[2-(4-methoxyphenyl)ethylamino-[1,2,4]-triazolo[1,5-a][1,3,5]triazine, m.p. 211°–213° C. microanalysis, found: C,58.2; H,4.7; N,27.8%; $C_{17}H_{17}N_7O_2$ requires: C,58.1; H,4.9; N,27.9%; NMR: 2.80(t,2H, CH̲$_2$-phenyl); 3.44(m,2H, CH̲$_2$N); 3.72(s,3H, CH̲$_3$O), 6.66(d of d, 1H, furyl-4H̲), 6.65 and 7.14 ($A_2B_2$ pattern, 4.11, 4-phenyl-H̲); 7.05(d,1H, furyl-3H̲), 7.45(t,1H, NH̲); 7.86(d, 1H, furyl-5H̲) and 8.04(brs, 2H, NH̲$_2$); m/e 352 (M+H)$^+$.

EXAMPLE 162

Using a procedure similar to that described in Example 3 there was obtained 7-amino-5-[2-(2-benzyloxyphenyl)ethyl]amino-2-(2-furyl)-[1,2,4]-triazolo[1,5-a][1,3,5]triazine; m.p. 151°–153° C. microanalysis, found: C,64.4; H,4.8; N,23.0%; $C_{23}H_{21}N_7O_2$ requires: C,64.6; H,4.95; N,22.9%; NMR: 2.90(t,2H, phenyl CH̲$_2$); 3.53(m,2H, CH̲$_2$N); 5.13(s,2H, CH̲$_2$O); 6.68(d of d, 1H, furyl-4H̲), 7.04(d,1H, furyl-3H̲), 6.8–7.6 (complex, 9H, phenyl-H̲); 7.88(s,1H, furyl-5H̲) and 8.11 (brs, 2H, NH̲$_2$); m/e 428 (M+H)$^+$.

EXAMPLE 163

Using a procedure similar to that described in Example 3 there was obtained 7-amino-5-[(3-benzyloxy-4-methoxyphenyl)methyl]amino-2-(2-furyl)-[1,2,4]-triazolo[1,5-a][1,3,5]triazine, m.p. 173°–175° C. microanalysis, found: C,62.3; H,4.6; N,22.1%; $C_{23}H_{21}N_7O_3$ requires: C,62.3; H,4.8; N,22.1%; NMR 3.76(s,3H, CH̲$_3$O), 4.44(d,2H, CH̲$_2$N); 5.04(s,2H, CH̲$_2$O) 6.66(d of d, 1H, furyl-4H̲), 6.75–7.75 (complex, 8H, phenyl-H̲), 7.03(d,1H, furyl 3H̲), 7.5(s,1H, furyl-5H̲), 7.66(m, 1H, NH̲) and 8.18(brs, 2H, NH̲$_2$); m/e 444 (M+H)$^+$.

EXAMPLE 164

Using a procedure similar to that described in Example 3 there was obtained 7-amino-2-(2-furyl)-5-[2-(3-methoxyphenyl)ethyl]amino-[1,2,4]-triazolo[1,5-a][1,3,5]triazine, m.p. 172°–174° C. microanalysis, found: C,57.6; H,4.7; N,28.0; H$_2$O, 0.4%; C$_{17}$H$_{17}$N$_7$O$_2$(0.1)H$_2$O requires: C,57.7; H,4.9; N,27.8; H$_2$O, 0.5%; NMR: 2.83(t,2H, phenyl-CH$_2$); 3.50(m,2H, CH$_2$N), 3.74(s,3H, CH$_3$O); 6.65 (d of d, 1H, furyl-4H); 6.7–7.3 (complex, 4H, phenyl-H); 7.04(d, 1H, furyl-3H), 7.40(t,1H, NH), 7.83(m,1H, furyl-5H), 8.07(brs, 2H, NH$_2$); m/e 352 (M+H)+.

EXAMPLE 165

Using a procedure similar to that described in Example 3 there was obtained 7-amino-2-(2-furyl)-5-[(2-methoxphenyl )methyl ]amino-[1,2,4]-triazolo[1,5-a][1,3,5]triazine, m.p. 249°–251° C. microanalysis, found: C,56.9; H,4.4; N,29.2%; C$_{16}$H$_{15}$N$_7$O$_2$ requires: C,57.0; H,4.5; N,29.1%; NMR: 3.83(s,3H, CH$_3$O), 4.49(d,2H, CH$_2$N), 6.65(d of d, 1H, furyl-4H), 6.8–7.3 (complex, 4H, phenyl-H); 7.03(s,1H, furyl-3H), 7.69(t, 1H, NH), 7.84(d,1H, furyl-5H) and 8.15(brs, 2H, NH$_2$); m/e 338 (M+H)+.

EXAMPLE 166

Using a procedure similar to that described in Example 3 there was obtained 7-amino-2-(2-furyl)-5-[(4-methoxyphenyl)methyl]amino-[1,2,4]-triazolo[1,5-a][1,3,5]triazine, m.p. 237.5°–239° C. microanalysis, found: C,56.7; H,4.5; N,28.8%; C$_{16}$H$_{15}$N$_7$O$_2$ requires: C,57.0; H,4.5; N,29.1%; NMR: 3.72(s,3H, CH$_3$O), 4.42(d,2H, CH$_2$N); 6.66(d of d, 1H, furyl-4H), 6.86 and 7.28 (A$_2$B$_2$ pattern, 4H, 9 phenyl-H), 7.04(d,1H, furyl-3H), 7.86(m, 1H, furyl-5H), 7.91 (complex, 1H, NH) and 8.16(brs, 2H, NH$_2$); m/e 338 (M+H)+.

EXAMPLE 167

A solution of the product of Example 161 (0.9 g) in methanol (150 ml) was hydrogenated at room-temperature and pressure using 10% palladium on carbon (0.9 g) catalyst. After the uptake of hydrogen was complete, the catalyst was filtered off and the solvent evaporated. The residue was crystallised from ethanol, and gave 7-amino-2-(2-furyl)-5-[2-(hydroxyphenyl)ethyl]amino-[1,2,4]triazolo[1,5-a][1,3,5]triazine, m.p. 260°–263° C. microanalysis, found: C,57.2; H,4.8; N,28.6%; C$_{16}$H$_{15}$N$_7$O$_2$ (0.15) C$_2$H$_5$OH requires: C,57.0; H,4.7; N,28.5%; NMR: 2.81(t,2H, phenyl-H), 3.49(m,2H, CH$_2$N); 6.71(d of d, 1H, furyl-4H), 7.03(d, 1H, furyl-3H), 6.7–7.15 (complex, 4H, phenyl-H); 7.85(m, 1H NH); 7.84(s,1H, furyl-5H); 8.09(brs, 2H, NH$_2$) and 9.31(s,1H, OH); m/e 338 (M+H)+.

EXAMPLE 168

Using a procedure similar to that described in Example 2 there was obtained 7-amino-2-(2-furyl)-5-(2-phenylethylthio)[1,2,4]triazolo[1,5-a][1,3,5]triazine, as white needles from ethanol m.p. 219°–221° C. microanalysis, found: C 57.2; H,4.1; N,24.6%; C$_{16}$H$_{14}$N$_6$OS requires: C,56.8; H,4.2; N,24.8%; NMR: 3.01(m,2H, phenyl-CH$_2$), 3.36(m,2H, CH$_2$S), 6.71(d of d, 1H, furyl-4H), 7.18(d, 1H, furyl-4H), 7.2–7.4 (complex, 5H, phenyl-H); 7.91(m, 1H, furyl-5H) and 8.88 (dbr, 2H, NH$_2$), m/e 339 (M+H)+.

EXAMPLE 169

Using a procedure similar to that described in Example 119 but using 2-phenylethanethiol instead of phenol, there was obtained 7-amino-2-(2-furyl)-5-(2-phenylethylthio)-pyrazolo[2,3-a][1,3,5]triazine as a white solid from ethanol m.p. 233°–235° C. microanalysis, found: C,60.9; H,4.4; N,20.8%; C$_{17}$H$_{15}$N$_5$OS requires: C,60.5; H,4.5; N,20.8%; NMR: 3.00(t,2H, phenyl-CH$_2$), 3.31(t,2H, CH$_2$S), 6.54(s,1H, pyrazole-3H), 6.66(d of d, 1H, furyl-4H), 7.03(d of d, 1H, furyl-3H), 7.2–7.4 (complex, 4H, phenyl-H), 7.63(m, 1H, furyl-5H) and 8.5(brd, 2H, NH$_2$); m/e 338 (M+H)+.

EXAMPLE 170

Using a procedure similar to that described in Example 3 there was obtained 7-amino-5-(3,4-dimethoxyphenyl)-2-(2-furyl)-[1,2,4]-triazolo[1,5-a][1,3,5]triazine as a crystalline solid from ethanol, m.p. 205°–208° C.; microanalysis, found: C,56.5; H,5.0; N,25.7%; C$_{18}$H$_{19}$N$_7$O$_3$ requires: C,56.7; H,5.0; N,25.7%; NMR: 2.79(t,2H, phenyl-CH$_2$), 3.45(m,2H, CH$_2$N), 3.71(s,3H, CH$_3$O), 3.75(s,3H, CH$_3$O); 6.66(d of d, 1H, furyl-4H); 6.7–6.9 (complex, 3H, phenyl-H), 7.04 (d, 1H, furyl-3H), 7.40(t, 1H, NH), 7.84(m, 1H, furyl-5H) and 8.09(brs, 2H, NH$_2$); m/e 382 (M+H)+.

EXAMPLE 171

Using a procedure similar to that described in Example 3 there was obtained 7-amino-(2-furyl)-5-[[2-(4-hydroxyphenoxy)ethyl]amino-]-[1,2,4]-triazolo[1,5-a][1,3,5]triazine, m.p. 266°–268° C.; microanalysis, found: C,54.0, H,4.0, N,27.5%; C$_{16}$H$_{15}$N$_7$O$_3$ requires: C,54.4; H,4.3; N,27.7%; NMR: 3.60(brd, 2H, CH$_2$N), 4.0(m,2H, OCH$_2$), 6.66 (complex, 1H, furyl-4H), 6.66 and 6.76 (A$_2$B$_2$ pattern, 4H, phenyl-H), 7.04(d, 1H, furyl-3H), 7.48 (complex, 1H, NH), 7.83(d, 1H, furyl-5H), 8.13(brs, 2H, NH$_2$) and 8.83(s,1H, OH): m/e 354 (M+H)+.

EXAMPLE 172

Using a procedure similar to that described in Example 16 there was obtained 7-amino-2-(2-furyl)-5-[2-(3-hydroxyphenyl)ethyl]amino-[1,2,4]-triazolo[1,5-a][1,3,5]triazine, m.p. 190°–193° C.; microanalysis, found C,57.3; H,4.4; N,29.2%; C$_{16}$H$_{15}$N$_7$O$_2$ requires: C,57.0; H,4.4; N,29.1%; NMR: 2.76(t,2H, phenyl-CH$_2$); 3.46(m,2H, CH$_2$N), 6.65(m, 1H, furyl-4H), 6.5–7.2 (complex, 4H, phenyl-H), 7.04(d, 1H, furyl-3H), 7.43(t, 1H, NH), 7.85(d,1H, furyl-5H), 8.1(brs,2H, NH$_2$) and 9.24(s,1H, OH); m/e 338 (M+H)+.

EXAMPLE 173

Using a procedure similar to that described in Example 1 there was obtained 7-amino-5-(3,5-dimethylphenoxy)-2-(2-furyl)-[1,2,4-]triazolo[1,5-a][1,3,5]triazine as a crystalline solid from ethanol m.p. 234°–236° C.; microanalysis, found: C,59.2; H,4.1; N,25.8%; C$_{16}$H$_{14}$N$_6$O$_2$ requires: C,59.6; H,4.4; N,26.1%; NMR: 2.28(s,6H, CH$_3$), 6.67(d of d, 1H, furyl-4H), 6.82(s,2H, phenyl-2H and phenyl-6H), 6.88(s,1H, phenyl-4H), 7.10(d of d, 1H, furyl-3H), 7.90(s,1H, furyl-5H) and 8.95(brs, 2H, NH$_2$); m/e 323 (M+H)+.

EXAMPLE 174

Using a procedure similar to that described in Example 3 there was obtained 7-amino-2-(2-furyl)-5-[(3,4,5-trimethoxyphenyl)methyl]amino-[1,2,4]-triazolo[1,5- a][1,3,5]triazine m.p 221°–224° C.; microanalysis, found: C,54.5; H,4.9; N,24.8%; $C_{18}H_{19}N_7O_4$ requires: C,54.4; H,4.8; N,24.7%; NMR: 3.63(s,3H, C$\underline{H}_3$O), 3.75(s,6H, 2×C$\underline{H}_3$O—), 4.45(d,2H, C$\underline{H}_2$N), 6.66(m,3H, furyl-4$\underline{H}$ and 2 phenyl-$\underline{H}$), 7.03(d,1H, furyl-3$\underline{H}$), 7.84(d of d, 1$\underline{H}$, furyl-5$\underline{H}$), 7.87(brt, 1H, N$\underline{H}$) and 8.15(brs, 2H, N$\underline{H}_2$), m/e 398 (M+H)+.

EXAMPLE 175

Using a procedure similar to that described in Example 3 there was obtained 7-amino-2-(2-furyl)-5-[(2-ethoxyphenyl )methyl]amino-[1,2,4]-triazolo[1,5-a][1,3,5]triazine, m.p. 243°–246° C.; microanalysis, found: C,58.3; H,4.9; N,28.0%; $C_{17}H_{17}N_7O_2$ requires: C,58.1; H,4.8; N,27.9%. NMR: 1.37(t,3H, C$\underline{H}_3$), 4.07(q,2H, C$\underline{H}_2$O), 4.49(d,2H, C$\underline{H}_2$N), 6.65(d of d, 1H, furyl-4$\underline{H}$), 6.81–7.01(m,3H, furyl-3$\underline{H}$ and 2 phenyl-$\underline{H}$), 7.15–7.22(m,2H, 2-phenyl-1$\underline{H}$), 7.67(brt, 1H, N$\underline{H}$), 7.84(d, 1H, furyl-5$\underline{H}$), 8.15(brs,2H, N$\underline{H}_2$); m/e 352 (M+H)+.

EXAMPLE 176

Using a procedure similar to that described in Example 1 there was obtained 7-amino-2-(2-furyl)-5-[(3,5-dimethoxy)phenoxy][1,2,4]-triazolo[1,5-a][1,3,5]triazine, m.p. 248°–250° C.; microanalysis, found: C,54.4; H,4.0; N,24.0%; $C_{16}H_{14}N_6O_4$ requires: C,54.2; H,4.0; N,23.7%. NMR: 3.74(s,6H, C$\underline{H}_3$O), 6.42(m,3H, 3 phenyl-$\underline{H}$); 6.68(d of d, 1H, furyl-4$\underline{H}$), 7.11(d of d, 1H, furyl-3$\underline{H}$), 7.89(d of d, 1H, furyl-5$\underline{H}$), 8.82–9.09(brd, 2H, N$\underline{H}_2$); m/e 355 (M+H)+.

EXAMPLE 177

Using a procedure similar to that described in Example 1 there was obtained 7-amino-2-(2-furyl)-5-[(3,5-difluoro)phenoxy][1,2,4]triazolo[1,5-a][1,3,5]triazine, m.p. >300° C.; microanalysis, found: C, 50.6; H, 2.5; N, 25.3%; $C_{14}H_8F_2N_6O_2$ requires: C, 50.9; H 2.4; N, 25.4%; NMR: 6.69 (d of d, 1H, furyl-4$\underline{H}$); 7.11–7.16 (m, 4H, furyl-3H and 3 phenyl-$\underline{H}$); 7.90 (d of d, 1H, furyl-5$\underline{H}$); 8.80–9.30 (br d, 2H, N$\underline{H}_2$); m/e 331 (M+H)+.

EXAMPLE 178

Using a procedure similar to that described in Example 1 there was obtained 7-amino-2-(2-furyl)-5-[(2,6-dichloro)phenoxy][1,2,4]triazolo[1,5-a][1,3,5]triazine, m.p. 270°–272° C.; microanalysis, found: C, 46.7; H 2.9; N, 21.7%; $C_{14}H_8Cl_2N_6O_2.(0.4)C_2H_5OH$ requires: C, 46.6; H, 2.7; N, 22.0%; NMR: 6.69–6.72 (d of d, 1H, furyl-4$\underline{H}$); 7.13–7.16 (d of d, 1H, furyl-3$\underline{H}$); 7.35–7.44 (d of d, 1H, phenyl-$\underline{H}$); 7.62–7.67 (d, 2H, 2 phenyl-$\underline{H}$); 7.92–7.93 (d of d, 1H, furyl-5$\underline{H}$); 9.11–9.32, (br.d, 2H, N$\underline{H}_2$); m/e 362 (M)+.

EXAMPLE 179

Using a procedure similar to that described in Example 3 there was obtained 7-amino-2-[2-furyl)-5-[(3-fluorophenyl)methyl]amino[1,2,4]triazolo[1,5-a][1,3,5]triazine, m.p. 216°–218° C.; microanalysis, found: C, 55.7; H, 3.8; N, 30.4; F, 5.5%; $C_{15}H_{12}FN_7O$ requires: C, 55.4; H, 3.7; N, 30.1; F, 5.8%; NMR 4.50, (d, 2H, CH2N), 6.66 (d of d, 1H, furyl-4$\underline{H}$); 7.03 (d, 1H, furyl-3$\underline{H}$); 7.1–7.5 (complex, 5H, phenyl-$\underline{H}$), 7.84 (d, 1H, furyl-5$\underline{H}$); 7.97 (t, 1H, N$\underline{H}$) and 8.19 (br s, 2H, N$\underline{H}_2$); m/e 326 (M+H)+.

EXAMPLE 180

N-(2-Aminoethyl)morpholine (2.60 g) was added to a stirred suspension of 7-amino-2-(2-furyl)-5-methylsulphonyl-[1,2,4]triazolo[1,5-a][1,3,5]triazine (3.36 g) in acetonitrile 200 ml and stirring was continued for 2 hours. The solvent was evaporated and the residue was purified by chromatography on silica (200 g) eluting with dichloromethane containing methanol (10% v/v). The solid (4.0 g) obtained was crystallised from ethanol to give 7-amino-2-(2-furyl)-5-[2-(morpholino)ethylamino][1,2,4]triazolo[1,5-a][1,3,5]triazine (3.03 g), m.p. 242°–4° C.; microanalysis, found: C,50.7; H,5.40; N,33.7%; $C_{14}H_{18}N_8O_2$ requires C 50.9 H 5.5 N 33.9% NMR: 2.47 (broad, 6H, C$\underline{H}_2$N(C$\underline{H}_2$)$_2$), 3.43 (q,2H, CH$_2$NH), 3.61(m,4H,C$\underline{H}_2$OC$\underline{H}_2$), 6.68 (d of d, 1H, furyl-4$\underline{H}$, 7.06(d, 1H, furyl-3$\underline{H}$), 7.27(br, 1H, N$\underline{H}$), 7.86(d,1H, furyl-5$\underline{H}$) and 8.15 (br, 2H, N$\underline{H}_2$); m/e 331(M+H)+.

EXAMPLE 181

A mixture of 7-amino-2-(2-furyl)-5-phenoxy-[1,2,4]triazolo[1,5-a][1,3,5]triazine (1.47 g) and N-(2-aminoethyl)-morpholine (0.78 g) in propanol (75 ml) was heated under reflux for 48 hours, until thin layer chromatography indicated that the reaction was essentially complete. The solvent was removed and the residue purified by chromatography on silica eluting with methylene chloride methanol 10% v/v. The solid (1.1 g) obtained was crystallised from ethanol to give 7-amino-2-(2-furyl)-5-[2-(morpholino)ethylamino][1,2,4]-triazolo[1,5-a][1,3,5]-triazine (0.69 g) m.p. 243°–6° C. identical in all respects to the product obtained in Example 180.

The necessary starting material may be prepared as follows:

Hexamethyldisiloxane (3.0 mole) is charged to a slurry of phosphorus pentoxide (1.5 mole, measured as $P_4O_{10}$) in xylene. The mixture is then heated to 90° C. over 1.5 hours and then stirred for 1 hour at 90° C. during which time all of the solid dissolves. N-2-(4,6-diphenoxy)-[1,3,5]triazinyl]-N'-(2-furoyl)hydrazine (1.0 mole) is then charged to the solution and the temperature is increased to reflux. The solid dissolves, but during the course of the cyclisation a second solid is precipitated. The cyclisation is normally complete in 2.5 hours at which point the mixture is cooled to 25° C., and can for convenience be held overnight. Acetonitrile is then added and the temperature reduced to 15° C. Water is then added. The mixture is then cooled back to 15° C. and 0.91 ammonia solution is added, keeping the temperature below 25° C. Once the addition is complete the temperature is increased to 40° C. for 1 hour. The reaction mixture is then cooled to 25° C., the solid filtered off and washed with a large volume of water. The yield is approximately 85%.

The requisite N-2-(4,6-diphenoxy)-[1,3,5]triazinyl-N'-(2furoyl)hydrazine was prepared as follows:

A solution of 2,4,6-triphenoxy-1,3,5-triazine (7.2 g) and 2-furoic acid hydrazide (2.5 g) in xylene (60 ml) was heated under reflux for 3 hours. The solvent was then removed by evaporation and the residue was purified by chromatography on silica gel (400 g), eluting with methylene chloride/methanol (2–3% v/v). A solid was obtained, and this was crystallised from isopropanol to give N-2-(4,6-diphenoxy)-[1,3,5]triazinyl-N'-(2-furoyl)-hydrazine as colourless prisms; m.p. 182°–4 ° C.; microanalysis; found C, 61.4; H, 3.8; N, 17.7%; $C_{20}H_{15}N_5O_4$ requires C, 61.7; H, 3.9; N, 18.0%; NMR 6.63 (d of d, 1H, 4-furyl H), 7.05-7.5 (complex, 1H, 3-furyl H and phenyl H), 7.87 (s, H, 5-furyl H), 9.96 (s, 1H, NH) and 10.34 (s, 1H, NH); m/e 390 (M+H)+.

EXAMPLE 182

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (b) Capsule | mg/capsule |
| Compound X | 10 |
| Lactose Ph. Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

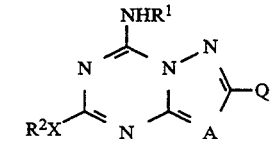   I

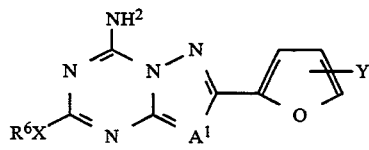   II

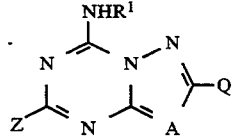   III

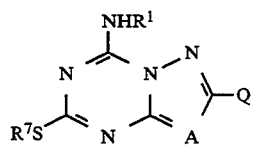   IV

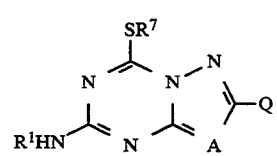   IVa

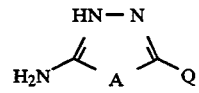   V

-continued
CHEMICAL FORMULAE

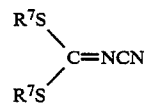   VI

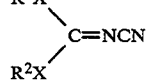   VII

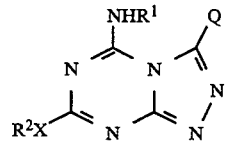   VIII

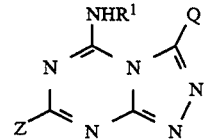   IX

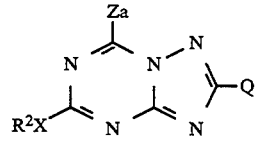   X

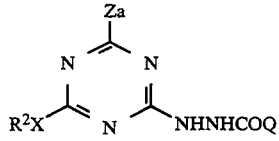   XI

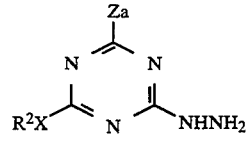   XII

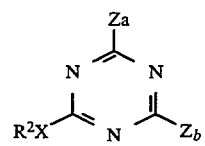   XIII

What is claimed is:
1. A compound of the formula I:

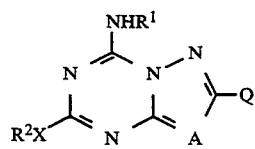   (I)

wherein:
Q is furyl or thienyl, optionally bearing 1 or 2 substituents independently selected from (1-4C) alkyl and halogeno;
$R^1$ is hydrogen, (1-6C)alkyl, or (1-4C)alkanoyl;
$R^2$ is a group of the formula $R^5.Xa.CH_2.CH_2$— in which the group $R^5.Xa$— is morpholino; and
X is oxy, thio or an imino group of formula —NRa— in which Ra is hydrogen or (1-6C) alkyl; and A is N; or
a pharmaceutically acceptable salt thereof.

2. The compound of claim 1, in which Q is 2-furyl.

3. A compound of the formula I:

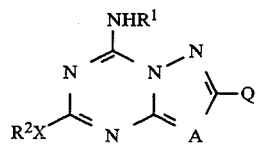

wherein:
Q is 2-furyl;
$R^1$ is hydrogen;
$R^2$ is a group of the formula $R^5.Xa.CH_2.CH_2-$ in which the group $R^5.Xa-$ is morpholino; and
X is an imino group of formula $-NRa-$ in which Ra is hydrogen; and
A is N; or
a pharmaceutically acceptable salt thereof.

4. The compound as claimed in claim 1, wherein $R^1$ is hydrogen, methyl, ethyl, propyl, butyl, formyl, acetyl, or propionyl.

5. A pharmaceutical composition, which comprises a compound of formula I, or a pharmaceutically acceptable salt thereof, as claimed in claim 1 in admixture or together with a pharmaceutically acceptable diluent or carrier.

6. A method of antagonizing one or more of the actions of adenosine in a warm-blooded animal requiring such treatment by administering an effective amount of a compound of formula I as defined in claim 1, or a pharmaceutically acceptable salt thereof.

7. A pharmaceutical composition, which comprises a compound of formula I, or a pharmaceutically acceptable salt thereof as claimed in claim 3.

8. A method of antagonizing one or more of the vasodilatory actions of adenosine in a warm-blooded mammal requiring such treatment by administering an effective amount of a compound of formula I as defined in claim 3, or a pharmaceutically acceptable salt thereof.

* * * * *

UNITED STATES PATENT AND TRADEMARK OFFICE
CERTIFICATE OF CORRECTION

PATENT NO.    :    5,356,894

DATED         :    Oct. 18, 1994

INVENTOR(S)   :    RODNEY et al.

It is certified that error appears in the above-identified patent and that said Letters Patent is hereby corrected as shown below:

On the title page, item [76]:
by "Inventors:", delete "Peter W. Rodney" and replace it with --Peter W. R. Caulkett--.

In the heading (under "United States Patent [19]", delete "Rodney et al." and replace it with --Caulkett et al.--.

In the left hand column, insert field --[73] Assignee: Zeneca Limited--.

Signed and Sealed this

Ninth Day of May, 1995

BRUCE LEHMAN

Attest:

Attesting Officer

Commissioner of Patents and Trademarks